(12) United States Patent
Winnicki et al.

(10) Patent No.: US 9,879,292 B2
(45) Date of Patent: *Jan. 30, 2018

(54) APPARATUS AND METHODS FOR BIOSYNTHETIC PRODUCTION OF CANNABINOIDS

(71) Applicant: FULL SPECTRUM LABORATORIES LIMITED, Dublin (IE)

(72) Inventors: Robert Winnicki, Cambridge, MA (US); Marc Donsky, Denver, CO (US); Mingyang Sun, Dublin (IE); Richard Peet, Washington, DC (US)

(73) Assignee: Teewinot Technologies, Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/433,270

(22) Filed: Feb. 15, 2017

(65) Prior Publication Data

US 2017/0233778 A1 Aug. 17, 2017

Related U.S. Application Data

(63) Continuation of application No. 15/232,405, filed on Aug. 9, 2016, now Pat. No. 9,587,212, which is a
(Continued)

(51) Int. Cl.
*C12M 1/00* (2006.01)
*C12M 3/00* (2006.01)
(Continued)

(52) U.S. Cl.
CPC .............. *C12P 17/06* (2013.01); *C07C 29/80* (2013.01); *C07C 37/01* (2013.01); *C07C 37/74* (2013.01);
(Continued)

(58) Field of Classification Search
CPC ...... C12M 41/00; C12M 41/30; C12M 41/32; C12M 41/38; C12M 41/46
See application file for complete search history.

(56) References Cited

U.S. PATENT DOCUMENTS 5,086,646 A 2/1992 Jamison et al.
5,290,701 A 3/1994 Wilkins
(Continued)

FOREIGN PATENT DOCUMENTS

JP 2000-078979 A 3/2000
JP 2001-029082 A 2/2001
(Continued)

OTHER PUBLICATIONS

De Meijer; "The Inheritance of Chemical Phenotype in *Cannabis sativa* L."; Genetics, 163:335-346 (Jan. 2003).
(Continued)

*Primary Examiner* — Nathan A Bowers
(74) *Attorney, Agent, or Firm* — Foley & Lardner LLP

(57) ABSTRACT

The present invention provides an apparatus and methods for producing tetrahydrocannabinolic acid (THCA), cannabichromenic acid (CBCA) and cannabichromenic acid (CBCA) in different ratios. The apparatus comprises: (i) a bioreactor comprising (a) an automated supply system configured to deliver a first automated supply of cannabigerolic acid (CBGA), a cannabinoid acid synthase, and a reaction mixture; and (b) a second automated system to cease the reaction; (ii) a controller configured to modify a property of the reaction mixture to produce the desired products; and (iii) an extractor configured to recover the tetrahydrocannabinolic acid (THCA), cannabichromenic acid (CBCA) or cannabidiolic acid (CBDA) and cannabichromenic acid.

12 Claims, 17 Drawing Sheets

Related U.S. Application Data continuation of application No. 15/158,565, filed on May 18, 2016, now Pat. No. 9,512,391, which is a continuation of application No. 14/835,444, filed on Aug. 25, 2015, now Pat. No. 9,394,510.

(60) Provisional application No. 62/041,521, filed on Aug. 25, 2014.

(51) Int. Cl.
| | |
|---|---|
| C12P 17/00 | (2006.01) |
| C12P 17/06 | (2006.01) |
| C12M 1/40 | (2006.01) |
| C12M 1/34 | (2006.01) |
| C12M 1/36 | (2006.01) |
| C12N 9/02 | (2006.01) |
| C07C 29/80 | (2006.01) |
| C07C 37/01 | (2006.01) |
| C07C 37/74 | (2006.01) |

(52) U.S. Cl.
CPC ............ *C12M 21/18* (2013.01); *C12M 29/04* (2013.01); *C12M 41/12* (2013.01); *C12M 41/26* (2013.01); *C12M 41/32* (2013.01); *C12M 41/40* (2013.01); *C12M 41/48* (2013.01); *C12M 47/10* (2013.01); *C12N 9/0004* (2013.01); *C12Y 121/03007* (2015.07); *C12Y 121/03008* (2015.07)

(56) References Cited

U.S. PATENT DOCUMENTS

| | | |
|---|---|---|
| 5,434,062 A | 7/1995 | Groldeau et al. |
| 6,113,940 A | 9/2000 | Brooke et al. |
| 6,403,126 B1 | 6/2002 | Webster et al. |
| 6,949,582 B1 | 9/2005 | Wallace |
| 8,426,411 B2 | 4/2013 | Wishart et al. |
| 9,359,625 B2 | 6/2016 | Winnicki et al. |
| 9,394,510 B2 | 7/2016 | Peet et al. |
| 9,512,391 B2 | 12/2016 | Peet et al. |
| 9,526,715 B1 | 12/2016 | Winnicki et al. |
| 2002/0136752 A1 | 9/2002 | Whittle et al. |
| 2004/0034108 A1 | 2/2004 | Whittle |
| 2004/0053386 A1 | 3/2004 | Chappell et al. |
| 2005/0266108 A1 | 12/2005 | Flockhart et al. |
| 2006/0172417 A1 | 8/2006 | Rathenow et al. |
| 2006/0183211 A1 | 8/2006 | Kuzuyama et al. |
| 2008/0262099 A1 | 10/2008 | Whittle et al. |
| 2010/0170142 A1 | 7/2010 | Posselt et al. |
| 2010/0239693 A1 | 9/2010 | Guy et al. |
| 2010/0298579 A1 | 11/2010 | Steup et al. |
| 2011/0003703 A1 | 1/2011 | Ma et al. |
| 2011/0060463 A1 | 3/2011 | Selker et al. |
| 2011/0086915 A1 | 4/2011 | Gierskcky et al. |
| 2011/0091930 A1 | 4/2011 | Vacanti et al. |
| 2011/0098348 A1 | 4/2011 | De Meijer |
| 2011/0182934 A1 | 7/2011 | Nutricia |
| 2012/0117686 A1 | 5/2012 | Scheller et al. |
| 2012/0144523 A1 | 6/2012 | Page et al. |
| 2012/0322114 A1 | 12/2012 | Liu et al. |
| 2013/0059018 A1 | 3/2013 | Parolaro et al. |
| 2013/0067619 A1 | 3/2013 | Page et al. |
| 2014/0057251 A1 | 2/2014 | McKernan |
| 2014/0141476 A1 | 5/2014 | Page et al. |
| 2014/0221469 A1 | 8/2014 | Ross et al. |
| 2014/0243405 A1 | 8/2014 | Whalley et al. |
| 2014/0287068 A1 | 9/2014 | Lewis et al. |
| 2014/0343136 A1 | 11/2014 | Izzo et al. |
| 2015/0057270 A1 | 2/2015 | Boger |
| 2015/0057341 A1 | 2/2015 | Perry |
| 2015/0126754 A1 | 5/2015 | Fernandez Cid et al. |
| 2015/0265636 A1 | 9/2015 | Kane et al. |
| 2015/0361469 A1 | 12/2015 | Winnicki et al. |
| 2016/0053220 A1 | 2/2016 | Peet et al. |
| 2016/0120874 A1 | 5/2016 | Perez et al. |
| 2016/0145563 A1 | 5/2016 | Berteau et al. |
| 2016/0340629 A1 | 11/2016 | Winnicki et al. |
| 2016/0355854 A1 | 12/2016 | Winnicki et al. |

FOREIGN PATENT DOCUMENTS

| | | |
|---|---|---|
| WO | WO-2004/016254 A2 | 2/2004 |
| WO | WO-2011/127589 A1 | 10/2011 |
| WO | WO-2014/134281 A1 | 9/2014 |
| WO | WO-2016/030828 | 3/2016 |

OTHER PUBLICATIONS

Russo; "Taming THC: potential cannabis synergy and phytocannabinoid-terpenoid entourage effects"; British Journal of Pharmacology, 163:1344-1364 (Jul. 2011).

U.S. Non-Final Office Action issued in U.S. Appl. No. 15/430,122 dated Mar. 13, 2017.

U.S. Non-Final Office Action issued in U.S. Appl. No. 15/441,109 dated Mar. 24, 2017.

CLIB (2010); "Production of cannabinoids in a microbial host"; p. 1.

F. Taura et al., "Purification and Characterization of Cannabidiolic-acid Synthase from *Cannabis sativa* L.: Biochemical Analysis of a Novel Enzyme That Catalyzes the Oxidocyclization of Cannabigerolic Acid to Cannabidiolic Acid", Journal of Biological Chemistry, Jul. 19, 1996, pp. 17411-17416, vol. 271, No. 29.

Flemming, T., et al.; Chemistry and Biological Activity of Tetra-hydrocannabinol and its Derivatives; Top Heterocycl Chem (2007) 10: 1-42; Springer-Verlag Berlin Heidelbert, Aug. 14, 2007; pp. 1-42.

Futoshi Taura et al., "First Direct Evidence for the Mechanism of Δ1-Tetra hydrocannabinolic Acid Biosynthesis", J. Am. Chem. Soc. J. Am. Chem, Jan. 1, 1995, pp. 9766-9767, Retrieved from the Internet: URL:http://pubs.acs.org/doi/pdf/10.1021/ja00143a024.

Kerstin Lange et al., "Enrichment and identification of Δ9-Tetrahydrocannabinolic acid synthase from *Pichia pastoris* supernatants", Data in Brief, Sep. 2015, pp. 641-649, vol. 4.

Kerstin Lange et al., "Δ9-Tetrahydrocannabinolic acid synthase production in *Pichia pastoris* enables chemical synthesis of cannabinoids", Journal of Biotechnology, Oct. 1, 2015, pp. 68-76, vol. 211, NL.

Morimoto, Satoshi, et al.; "Enzymological Evidence for Cannabichromenic Acid Biosynthesis"; Journal of Natural Products; Aug. 1997; vol. 60, No. 8; pp. 854-857.

PCT International Search Report and Written Opinion on application PCT/IB2015/056445 dated Dec. 10, 2015; 18 pages.

PCT International Search report on application PCT/US14/18944 dated Jun. 9, 2014; 2 pages.

Sanchez, Isvett Josefina Flores; "Polyketide synthases in *Cannabis sativa* L"; Phytochem Rev (2008); pp. 1-169.

Sanja Martens et al., "Fully automated production of potential Malaria vaccines with *Pichia pastoris* in integrated processing", Engineering in Life Sciences, Aug. 1, 2011, pp. 429-435, vol. 11, No. 4, DE.

Taura et al., "Cannabidiolic-acid synthase, the chemotype-determining enzyme in the fiber-type *Cannabis sativa*", Febs Letters, Jun. 14, 2007, pp. 2929-2934, vol. 581, No. 16, Elsevier B.V., Amsterdam, NL.

Taura et al., "Production of Δ1-tetrahydrocannabinolic acid by the biosynthetic enzyme secreted from transgenic *Pichia pastoris*"; Biochemical and Biophysical Research Communications; 361(3): 675-680 (Sep. 2007); Elsevier Inc.

Taura, Futoshi; "Studies on tetrahydrocannabinolic acid synthase that produces the acidic precursor of tetrahydrocannabinol, the pharmacologically active cannabinoid in marijuana"; Drug Discoveries & Therapeutics, Jun. 2009; vol. 3, No. 3; pp. 83-87.

Thakur, Ganesh A., et al.; "Natural cannabinoids: Templates for drug discovery"; Life Sciences 78 (2005); pp. 454-466.

U.S. Non-final Office Action issued in U.S. Appl. No. 15/242,189 dated Jan. 26, 2017.

(56) References Cited

OTHER PUBLICATIONS

USPTO Final Office Action issued in U.S. Appl. No. 15/232,405 dated Jan. 3, 2017.
USPTO Non-final Office Action issued in U.S. Appl. No. 14/835,444 dated Feb. 25, 2016; 8 pages.
USPTO Non-final Office Action issued in U.S. Appl. No. 14/836,339 dated Feb. 4, 2016; 11 pages.
USPTO Non-final Office Action issued in U.S. Appl. No. 15/158,565 dated Jul. 19, 2016.
USPTO Non-final Office Action issued in U.S. Appl. No. 15/232,405 dated Sep. 2, 2016.
USPTO Notice of Allowance issued in U.S. Appl. No. 14/835,444 dated Jun. 13, 2016; 15 pages.
USPTO Notice of Allowance issued in U.S. Appl. No. 14/836,339 dated May 4, 2016; 12 pages.
USPTO Notice of Allowance issued in U.S. Appl. No. 15/158,565 dated Sep. 6, 2016.
USPTO Notice of Allowance issued in U.S. Appl. No. 15/171,517 dated Sep. 21, 2016.
USPTO Notice of Allowance issued in U.S. Appl. No. 15/232,405 dated Jan. 13, 2017.
Zirpel Bastian et al., "Production of Δ9-terahydrocannabinolic acid from cannabigerolic acid by whole cells of Pichia (Komagataella) pastoris expressing Δ9-tetrahydrocannabinolic acid synthase from *Cannabis sativa*", Biotechnology Letters, May 21, 2015, pp. 1869-1875, vol. 37, No. 9, Springer Netherlands, NL.
Andre et al. (2016) *Cannabis sativa*: The Plant of the Thousand and One Molecules, Front. Plant Sci., vol. 7, pp. 1-17.
AZMMC (2017, updated) List of Major Cannabinoids in Cannabis and Their Effects, https://arizonamedical marijuanaclinic.com/list-of-major-cannabinoids-in-cannabis-and-their-effects/, pp. 1-12.
Mandolino et al. (2004) Potential of marker-assisted selection in hemp genetic improvement, Euphytica, vol. 140, pp. 107-120.
Shoyama et al., "Structure and Function of Δ1-Tetrahydrocannabinolic Acid (THCA) Synthase, the Enzyme Controlling the Psychoactivity of *Cannabis sativa*," Journal of Molecular Biology, vol. 423, 2012, pp. 96-105.
Shoyama, Yukihiro, "Cannabis Plant and Marihuana", Journal of Forensic Toxicology, vol. 12, No. 2, 1994, pp. 88-91 with English Summary.
Shoyama, Yukihiro, "Pharmacognosical Study during 40 Years," Review, vol. 127, No. 10, 2007, pp. 1593-1620 with English abstract.
Shoyama, Yukihiro, "Pharmacognosical Study on Secondary Metabolites," vol. 120, No. 9, 2000, pp. 749-765 with English abstract.
Sirikantaramas et al. (2005) Tetrahydrocannabinolic Acid Synthase, the Enzyme Controlling Marijuana Psychoactivity, is Secreted into the Storage Cavity of the Glandular Trichomes, Paint Cell Physiol., vol. 46, No. 9, pp. 1578-1582.
Sirikantaramas et al., "Cloning of THCA Synthase Gene and Its Distribution," National Library of Medicine, vol. 47, 2005, p. 23.
Taura et al. (2007) Phytocannabinoids in *Cannabis sativa*: Recent Studies on Biosynthetic Enzymes, Chem. Biochem., vol. 4, pp. 1649-1663).
Taura et al., "Biosynthetic Study on THCA, the Psychoactive Component of Marijuana," Seibutsu Butsuri [Biophysics], vol. 45, No. 4, 2005, pp. 178-184 with English translation.
Taura, Futoshi, "Studies on Enzymes Involved in Cannabinoid Biosynthesis," 1 page.
Pertwee et al., "O-1057, a potent water-soluble cannabinoid receptor agonist with antinociceptive properties," British Journal of Pharmacology, vol. 129, 2000, pp. 1577-1584.
Yu et al., "Dimethyl Sulphoxide: A Review of Its Application in Cell Biology," Bioscience Reports, vol. 14, No. 6, 1994, pp. 259-281.

APPARATUS AND METHODS FOR BIOSYNTHETIC PRODUCTION OF CANNABINOIDS

CROSS-REFERENCE TO RELATED APPLICATIONS

This application is a Continuation of U.S. application Ser. No. 15/232,405 filed Aug. 9, 2016, incorporated herein by reference in its entirety, which is a Continuation of U.S. application Ser. No. 15/158,565, filed May 18, 2016, now U.S. Pat. No. 9,512,391 issued Dec. 6, 2016, incorporated herein by reference in its entirety, which is a Continuation of U.S. application Ser. No. 14/835,444, filed Aug. 25, 2015, now U.S. Pat. No. 9,394,510 issued Jul. 19, 2016, incorporated herein by reference in its entirety, which claims priority from Provisional U.S. Application 62/041,521, filed Aug. 25, 2014, incorporated herein by reference in its entirety.

FIELD OF THE INVENTION

The present invention relates to the biosynthesis of cannabinoids. Specifically, the present invention relates to the production and manipulation of enzymes involved in the synthesis of cannabinoids, and to the simultaneous synthesis of various cannabinoids in different ratios.

BACKGROUND OF THE INVENTION

Cannabinoids are terpenophenolic compounds found in *Cannabis sativa*, an annual plant belonging to the Cannabaceae family. The plant contains more than 400 chemicals and approximately 70 cannabinoids. The latter accumulate mainly in the glandular trichomes. The most active of the naturally occurring cannabinoids is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. THC is also effective in the treatment of allergies, inflammation, infection, epilepsy, depression, migraine, bipolar disorders, anxiety disorder, drug dependency and drug withdrawal syndromes.

Additional active cannabinoids include cannabidiol (CBD), an isomer of THC, which is a potent antioxidant and anti-inflammatory compound known to provide protection against acute and chronic neuro-degeneration; cannabigerol (CBG), found in high concentrations in hemp, which acts as a high affinity $\alpha_2$-adrenergic receptor agonist, moderate affinity 5-$HT_{1A}$ receptor antagonist and low affinity CB1 receptor antagonist, and possibly has anti-depressant activity; and cannabichromene (CBC), which possesses anti-inflammatory, anti-fungal and anti-viral properties. Many phytocannabinoids have therapeutic potential in a variety of diseases and may play a relevant role in plant defense as well as in pharmacology. Accordingly, biotechnological production of cannabinoids and cannabinoid-like compounds with therapeutic properties is of uttermost importance. Thus, cannabinoids are considered to be promising agents for their beneficial effects in the treatment of various diseases.

Despite their known beneficial effects, therapeutic use of cannabinoids is hampered by the high costs associated with the growing and maintenance of the plants in large scale and the difficulty in obtaining high yields of cannabinoids. Extraction, isolation and purification of cannabinoids from plant tissue is particularly challenging as cannabinoids oxidize easily and are sensitive to light and heat. In addition, although it has been hypothesized that CBCA is predominantly synthesized from CBGA by the enzyme CBCA synthase, the enzyme has not been isolated or cloned. There is therefore a need for developing methodologies that allow large-scale production of cannabinoids for therapeutic use. The present invention addresses this need.

SUMMARY OF THE INVENTION

It is therefore an object of the invention to provide solutions to the aforementioned deficiencies in the art. To this end the invention provides a method of producing one or more cannabinoids or cannabinoid analogs comprising the steps of: (a) selecting a compound according to Formula I:

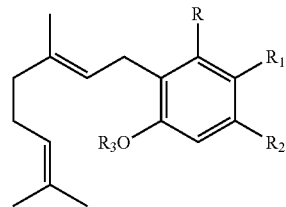

Formula I (b) selecting a cannabinoid acid synthase as a catalyst for transforming the compound according to Formula I into one or more cannabinoids or cannabinoid analogs; (c) reacting the compound of Formula I with the cannabinoid acid synthase in a reaction mixture comprising a solvent and an amphiphilic compound; (d) isolating from the reaction mixture one or more cannabinoid acids or cannabinoid analogs produced in step (c); and (e) optionally decarboxylating the cannabinoid acids or cannabinoid analogs isolated in step (c); wherein R is selected from —OH, halogen, —SH, or a —$NR_aR_b$ group; $R_1$ and $R_2$ are each independently selected from the group consisting of —H, —C(O)$R_a$, —O$R_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene, or $R_1$ and $R_2$ together with the carbon atoms to which they are bonded form a $C_5$-$C_{10}$ cyclic ring; $R_3$ is selected from the group consisting of H, —C(O)$R_a$ and $C_1$-$C_{10}$ linear or branched alkyl; and $R_a$ and $R_b$ are each independently —H, —OH, —SH, —$NH_2$, ($C_1$-$C_{10}$) linear or branched alkyl, or a $C_3$-$C_{10}$ cycloalkyl.

Preferably, the cannabinoid acid synthase is cannabidiolic acid (CBDA) synthase or tetrahydrocannabinolic acid (THCA) synthase. In a preferred aspect of the invention, the $C_5$-$C_{10}$ cyclic ring comprises one or more heteroatoms selected from oxygen, sulfur or nitrogen. In another preferred aspect of the invention, $R_2$ is a linear alkylene selected from the group consisting of $CH_3$, $C_2H_5$, $C_3H_7$, $C_4H_9$, $C_5H_{11}$, $C_6H_{13}$, $C_7H_{15}$ and $C_8H_{17}$. Preferably, $R_2$ is a $C_2$-$C_{10}$ alkenylene selected from the group consisting of

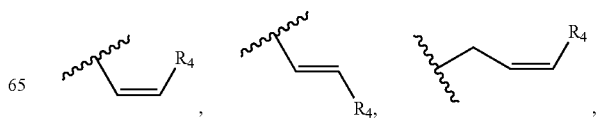

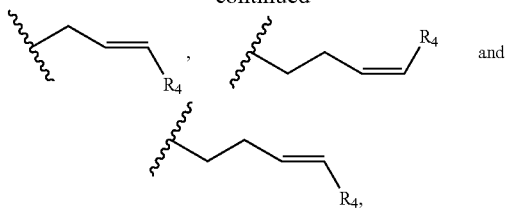

and $R_4$ is a linear alkylene selected from the group consisting of $CH_3$, $C_2H_5$, $C_3H_7$, $C_4H_9$, $C_5H_{11}$, $C_6H_{13}$, $C_7H_{15}$ and $C_8H_{17}$. In another preferred aspect, $R_2$ is a $C_2$-$C_{10}$ linear or branched alkynylene selected from the group consisting of

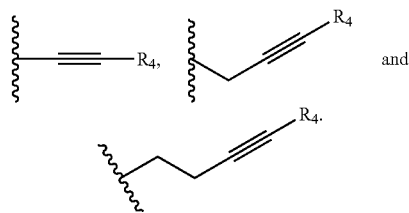

In an additional preferred embodiment, $R_2$ is

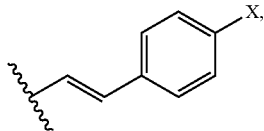

wherein X is —OH, —SH, or —$NR_aR_b$, and wherein $R_a$ and $R_b$ are each independently —H, —OH, —SH, —$NH_2$, ($C_1$-$C_{10}$) linear or branched alkyl, or a $C_3$-$C_{10}$ cycloalkyl. Most preferably, R is —OH, $R_1$ is —COOH, $R_2$ is $C_5H_{11}$ and $R_3$ is —H.

In one embodiment, the cannabinoid acid synthase is a recombinant cannabinoid acid synthase obtained by generating one or more copies of a cannabinoid acid synthase gene and overexpressing a protein encoded by the cannabinoid acid synthase gene. In a preferred aspect of the invention, one or more copies of a cannabinoid acid synthase gene are generated in vivo and the method comprises step (i) of integrating one or more copies of the cannabinoid acid synthase gene into the genome of an eukaryotic host to scale up protein expression. Preferably, the eukaryotic host is *Pichia pastoris* and the cannabinoid acid synthase gene is codon optimized with an alpha secretion sequence to target protein secretion and tagged with six tandem histidine residues (SEQ ID NO: 9). Step (i) may comprise linearizing the cannabinoid acid synthase gene by digestion with one or more restriction enzymes; extracting the cannabinoid acid synthase gene by gel extraction; ligating the cannabinoid acid synthase gene into a *Pichia pastoris* plasmid; and electroporating the plasmid into bacterial cells to generate one or more cannabinoid acid synthase gene copy colonies.

In a preferred aspect of the invention, the solvent is DMSO, and the concentration of DMSO in the reaction mixture is 20% (w/v). In an additional preferred aspect, the amphiphilic compound is a surfactant or a cyclodextrin. In a preferred embodiment, the cyclodextrin is α-cyclodextrin, β-cyclodextrin or γ-cyclodextrin. Even more preferably, the cyclodextrin is sulfobuthylether β-cyclodextrin sodium salt or randomly methylated β-cyclodextrin, and the concentration of cyclodextrin in the reaction mixture is between 2 and 28 mg/ml. In a most preferred embodiment, the concentration of cyclodextrin in the reaction mixture is 8 mg/ml.

In one embodiment, the cannabinoids or cannabinoid analogs are single enantiomers with an enantiomeric purity of at least 95%, and preferably of at least 99%.

In a preferred embodiment, the cannabinoid acid synthase is THCA synthase and the one or more cannabinoids or cannabinoid analogs are tetrahydrocannabinol (THCA), cannabichromene (CBCA), THCA and CBCA, or analogs thereof. In a preferred aspect, the amphiphilic compound is cyclodextrin and the mass:mass ratio of cyclodextrin to the compound of Formula I is 28:1 or the molar ratio of cyclodextrin to the compound of Formula I is 7.3:1. Preferably, step (c) of the reaction is performed at a pH in a range between 3.8 and 7.2, and the method produces THCA, CBCA, or THCA and CBCA in a ratio as shown in the following table at each specified pH:

| pH | THCA | CBCA |
| --- | --- | --- |
| 4 | 1 | 0 |
| 5 | 2.33 | 1 |
| 6 | 1 | 5.67 |
| 7 | 0 | 1 |
| 8 | 0 | 0 |

Preferably, 98% of the compound of Formula I is converted into one or more cannabinoids or cannabinoid analogs within two hours.

In a different embodiment, the cannabinoid acid synthase is CBDA synthase and the method produces cannabidiol (CBDA), cannabichromene acid (CBCA), CBDA and CBCA, or analogs thereof. Preferably, the amphiphilic compound is cyclodextrin and the mass:mass ratio of cyclodextrin to the compound of Formula I is 11:1 or the molar ratio of cyclodextrin to the compound of Formula I is 4:1. Preferably, step (c) is performed at a pH in a range between 3.8 and 7.2. In a preferred embodiment, the method produces CBDA, CBCA, or CBDA and CBCA in a ratio as shown in the following table at each specified pH:

| pH | CBDA | CBCA |
| --- | --- | --- |
| 4.2 | 2.5 | 1 |
| 5 | 1.13 | 1 |
| 5.2 | 1 | 1.17 |
| 5.4 | 1 | 2.45 |
| 5.8 | 1 | 6.14 |
| 6.2 | 1 | 28.13 |
| 6.8 | 0 | 0 |

Most preferably, 98% of the compound of Formula I is converted into one or more cannabinoids or cannabinoid analogs within two hours.

In a different embodiment, the invention provides a method of producing one or more cannabinoids or cannabinoid analogs according to Formula II

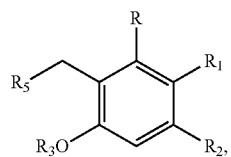

wherein the method comprises the steps of: (a) reacting a compound according to Formula III with a compound according to Formula IV;

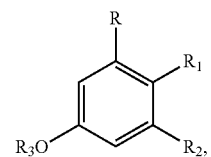

III

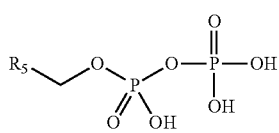

IV in the presence of an enzyme that catalyzes the reaction of the Formula III and Formula IV compounds to form a Formula II compound; (b) reacting the Formula II compound with a cannabinoid acid synthase in a reaction mixture comprising a solvent and an amphiphilic compound to produce one or more cannabinoids or cannabinoid analogs; (c) isolating from the reaction mixture one or more cannabinoids or cannabinoid analogs produced in step (b); and (e) optionally decarboxylating the one or more cannabinoids or cannabinoid analogs isolated in step (c); wherein R is selected from —OH, halogen, —SH, or a —$NR_aR_b$ group; $R_1$ and $R_2$ are each independently selected from the group consisting of —H, —C(O)$R_a$, —O$R_a$, an optionally substituted linear or branched ($C_1$-$C_{10}$)alkylene, an optionally substituted linear or branched ($C_2$-$C_{10}$)alkenylene, an optionally substituted linear or branched ($C_2$-$C_{10}$)alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene, or $R_1$ and $R_2$ together with the carbon atoms to which they are bonded form a $C_5$-$C_{10}$ cyclic ring; $R_3$ is selected from the group consisting of H, —C(O)$R_a$ and $C_1$-$C_{10}$ linear or branched alkyl; $R_5$ is selected from the group consisting of a linear or branched ($C_1$-$C_{10}$)alkylene, a linear or branched ($C_2$-$C_{10}$)alkenylene, a linear or branched ($C_2$-$C_{10}$)alkynylene, —C(O)—($C_1$-$C_{10}$)alkylene, —C(O)—($C_2$-$C_{10}$)alkenylene and —C(O)—($C_2$-$C_{10}$)alkynylene; wherein any alkylene, alkenylene, alkynylene, aryl, arylalkylene, or cycloalkyl group is further substituted with one or more groups selected from the group consisting of —OH, halogen, —$NR_bR_c$, —C(O)$R_a$, —C(O)$NR_bR_c$, ($C_1$-$C_{10}$) alkyl, —CN, ($C_1$-$C_4$)alkoxy, ($C_1$-$C_4$)haloalkyl, and ($C_1$-$C_4$) hydroxyalkyl; and $R_a$, $R_b$ and $R_c$ are each independently —H, —OH, —SH, —$NH_2$, ($C_1$-$C_{10}$) linear or branched alkyl, or a $C_3$-$C_{10}$ cycloalkyl.

In one embodiment, $R_5$ is a ($C_2$-$C_{10}$)alkenylene selected from the group consisting of

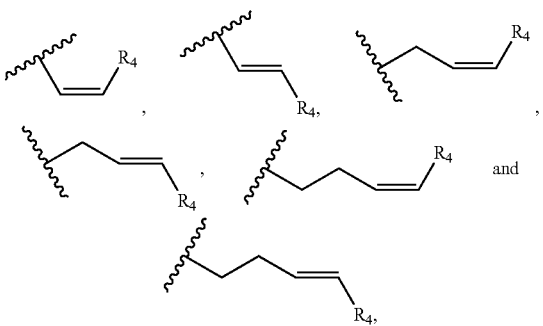

and $R_4$ is a linear alkylene selected from the group consisting of $CH_3$, $C_2H_5$, $C_3H_7$, $C_4H_9$, $C_5H_{11}$, $C_6H_{13}$, $C_7H_{15}$ and $C_8H_{17}$. In a preferred aspect of the invention, $R_5$ is

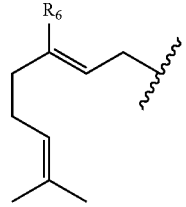

and $R_6$ is selected from ($C_1$-$C_{10}$)alkylene, ($C_2$-$C_{10}$)alkenylene, —OH, —SH, $NO_2$, F, Cl, Br, —$NH_2$, or —$NHR_a$.

In another preferred embodiment, the cannabinoid acid synthase is a recombinant cannabinoid acid synthase obtained by generating one or more copies of a cannabinoid acid synthase gene and by overexpressing a protein encoded by the cannabinoid acid synthase gene. Preferably, one or more copies of a cannabinoid acid synthase gene are generated in vivo and the method comprises step (i) of integrating one or more copies of the cannabinoid acid synthase gene into the genome of a eukaryotic host to scale up protein expression. Preferably, the eukaryotic host is *Pichia pastoris* and the cannabinoid acid synthase gene is codon optimized with an alpha secretion sequence to target protein secretion and tagged with six tandem histidine residues (SEQ ID NO: 9). Step (i) may comprise linearizing the cannabinoid acid synthase gene by digestion with one or more restriction enzymes; extracting the cannabinoid acid synthase gene by gel extraction; ligating the cannabinoid acid synthase gene into a *Pichia pastoris* plasmid; and electroporating the plasmid into bacterial cells to generate one or more cannabinoid acid synthase gene copy colonies.

In a preferred aspect of the invention, the solvent is DMSO, and the concentration of DMSO in the reaction mixture is 20% (w/v). In an additional preferred aspect, the amphiphilic compound is a surfactant or a cyclodextrin. In a preferred embodiment, the cyclodextrin is α-cyclodextrin, β-cyclodextrin or γ-cyclodextrin. Even more preferably, the cyclodextrin is sulfobuthylether β-cyclodextrin sodium salt or randomly methylated β-cyclodextrin, and the concentration of cyclodextrin in the reaction mixture is between 2 and 28 mg/ml. In a most preferred embodiment, the concentration of cyclodextrin in the reaction mixture is 8 mg/ml.

In one embodiment, the cannabinoids or cannabinoid analogs are single enantiomers with an enantiomeric purity of at least 95%, and preferably of at least 99%.

In a preferred embodiment, the cannabinoid acid synthase is THCA synthase and the one or more cannabinoids or cannabinoid analogs are tetrahydrocannabinol (THCA), cannabichromene (CBCA), THCA and CBCA, or analogs thereof. In a preferred aspect, the amphiphilic compound is cyclodextrin and the mass:mass ratio of cyclodextrin to the compound of Formula I is 28:1 or the molar ratio of cyclodextrin to the compound of Formula I is 7.3:1. Preferably, step (c) of the reaction is performed at a pH in a range between 3.8 and 7.2, and the method produces THCA, CBCA, or THCA and CBCA in different ratios as described above. Preferably, 98% of the compound of Formula I is converted into one or more cannabinoids or cannabinoid analogs within two hours.

In a different embodiment, the cannabinoid acid synthase is CBDA synthase and the method produces cannabidiol (CBDA), cannabichromene acid (CBCA), CBDA and CBCA, or analogs thereof. Preferably, the amphiphilic compound is cyclodextrin and the mass:mass ratio of cyclodextrin to the compound of Formula I is 11:1 or the molar ratio of cyclodextrin to the compound of Formula I is 4:1. Preferably, step (c) is performed at a pH in a range between 3.8 and 7.2, and the method produces CBDA, CBCA, or CBDA and CBCA in different ratios as described above. Most preferably, 70% of the compound of Formula I is converted into one or more cannabinoids or cannabinoid analogs within two hours.

In yet another embodiment, the invention provides a method for producing a tetrahydrocannabinol, cannabichromene, or both tetrahydrocannabinol and cannabichromene, or their analogs, wherein the method comprises the steps of: (a) selecting a compound according to Formula I;

Formula I

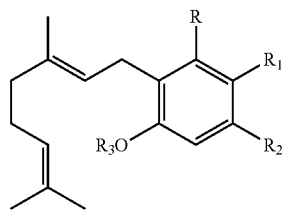

(b) reacting the compound of Formula I with a tetrahydrocannabinolic acid (THCA) synthase in a reaction mixture comprising a solvent and an amphiphilic compound; (c) modifying at least one property of the reaction mixture to obtain a tetrahydrocannabinol, a cannabichromene, or both tetrahydrocannabinol and cannabichromene, or their analogs as products; (d) isolating tetrahydrocannabinol, cannabichromene, or both tetrahydrocannabinol and cannabichromene, or their analogs from the reaction mixture; and (e) decarboxylating the tetrahydrocannabinolic acid, cannabichromenic acid, or both tetrahydrocannabinolic acid and cannabichromenic acid, or their analogs; wherein R is selected from —OH, halogen, —SH, or a —$NR_aR_b$ group; $R_1$ and $R_2$ are each independently selected from the group consisting of —H, —$C(O)R_a$, —$OR_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene, or $R_1$ and $R_2$ together with the carbon atoms to which they are bonded form a $C_5$-$C_{10}$ cyclic ring; $R_3$ is selected from the group consisting of —H, —$C(O)R_a$ and $C_1$-$C_{10}$ linear or branched alkyl; and $R_a$ and $R_b$ are each independently —H, —OH, —SH, —$NH_2$, ($C_1$-$C_{10}$) linear or branched alkyl, or a $C_3$-$C_{10}$ cycloalkyl.

In a preferred embodiment, the THCA synthase is a recombinant THCA synthase obtained by generating one or more copies of a THCA synthase gene and by overexpressing a protein encoded by the THCA synthase gene. Preferably, one or more copies of the THCA synthase gene are generated in vivo and the method comprises step (i) of integrating one or more copies of the cannabinoid acid synthase gene into the genome of a eukaryotic host to scale up protein expression. Preferably, the eukaryotic host is *Pichia pastoris* and the THCA synthase gene is codon optimized with an alpha secretion sequence to target protein secretion and tagged with six tandem histidine residues (SEQ ID NO: 9). Step (i) may comprise linearizing the cannabinoid acid synthase gene by digestion with one or more restriction enzymes; extracting the cannabinoid acid synthase gene by gel extraction; ligating the cannabinoid acid synthase gene into a *Pichia pastoris* plasmid; and electroporating the plasmid into bacterial cells to generate one or more cannabinoid acid synthase gene copy colonies.

In a preferred aspect of the invention, the solvent is DMSO, and the concentration of DMSO in the reaction mixture is 20% (w/v). In an additional preferred aspect, the amphiphilic compound is a surfactant or a cyclodextrin. In a preferred embodiment, the cyclodextrin is α-cyclodextrin, β-cyclodextrin or γ-cyclodextrin. Even more preferably, the cyclodextrin is sulfobuthylether β-cyclodextrin sodium salt or randomly methylated β-cyclodextrin, and the concentration of cyclodextrin in the reaction mixture is between 2 and 28 mg/ml. In a most preferred embodiment, the concentration of cyclodextrin in the reaction mixture is 8 mg/ml.

In a preferred aspect of the invention, the amphiphilic compound is cyclodextrin and the mass:mass ratio of cyclodextrin to the compound of Formula I is 28:1 or the molar ratio of cyclodextrin to the compound of Formula I is 7.3:1. Preferably, step (c) of modifying at least one property of the reaction mixture comprises modifying the pH of the reaction mixture in a range between 3.8 and 7.2, and the method produces THCA, CBCA, or THCA and CBCA in different ratios as described above. Preferably, 98% of the compound of Formula I is converted into one or more cannabinoids or cannabinoid analogs within two hours.

In a different embodiment, the invention provides a method for producing a cannabidiol, cannabichromene, or both cannabidiol and cannabichromene, or their analogs comprising the steps of: (a) selecting a compound according to Formula I;

Formula I

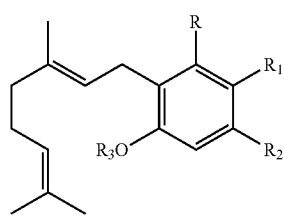

(b) reacting the compound of Formula I with a cannabinodiolic acid (CBDA) synthase in a reaction mixture comprising a solvent and an amphiphilic compound; (c) modifying at least one property of the reaction mixture to obtain a cannabidiol, a cannabichromene, or both cannabidiol and cannabichromene, or their analogs as products; (d) isolating cannabidiol, cannabichromene, or both cannabidiol and cannabichromene, or their analogs from the reaction mixture; and (e) decarboxylating the cannabidiol, cannabichromene, or both cannabidiol and cannabichromene, or their analogs; wherein R is selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$ and C$_1$-C$_{10}$ linear or branched alkyl; and R$_a$ and R$_b$ are each independently —H, —OH, —SH, —NH$_2$, (C$_1$-C$_{10}$) linear or branched alkyl, or a C$_3$-C$_{10}$ cycloalkyl.

Preferably, the CBDA synthase is a recombinant CBDA synthase obtained by generating one or more copies of a CBDA synthase gene and by overexpressing a protein encoded by the CBDA synthase gene. In a preferred aspect of the invention, one or more copies of a CBDA synthase gene are generated in vivo and the method comprises step (i) of integrating one or more copies of the CBDA synthase gene into the genome of a eukaryotic host to scale up protein expression. Preferably, the eukaryotic host is *Pichia pastoris* and the CBDA synthase gene is codon optimized with an alpha secretion sequence to target protein secretion and tagged with six tandem histidine residues (SEQ ID NO: 9). Step (i) may comprise linearizing the CBDA synthase gene by digestion with one or more restriction enzymes; extracting the CBDA synthase gene by gel extraction; ligating the CBDA synthase gene into a *Pichia pastoris* plasmid; and electroporating the plasmid into bacterial cells to generate one or more cannabinoid acid synthase gene copy colonies.

In a preferred aspect of the invention, the solvent is DMSO, and the concentration of DMSO in the reaction mixture is 20% (w/v). In an additional preferred aspect, the amphiphilic compound is a surfactant or a cyclodextrin. In a preferred embodiment, the cyclodextrin is α-cyclodextrin, β-cyclodextrin or γ-cyclodextrin. Even more preferably, the cyclodextrin is sulfobuthylether β-cyclodextrin sodium salt or randomly methylated β-cyclodextrin, and the concentration of cyclodextrin in the reaction mixture is between 2 and 28 mg/ml. In a most preferred embodiment, the concentration of cyclodextrin in the reaction mixture is 8 mg/ml.

In a preferred aspect of the invention, the amphiphilic compound is cyclodextrin and the mass:mass ratio of cyclodextrin to the compound of Formula I is 28:1(w/w) or the molar ratio of cyclodextrin to the compound of Formula I is 7.3:1. Preferably, step (c) of modifying at least one property of the reaction mixture comprises modifying the pH of the reaction mixture in a range between 3.8 and 7.2, and the method produces CBDA, CBCA, or CBDA and CBCA in different ratios as described above. In a preferred embodiment, 98% of the compound of Formula I is converted into one or more cannabinoids or cannabinoid analogs within two hours.

In a different embodiment, the invention provides a system for producing one or more cannabinoids or cannabinoid analogs, comprising: a fermentor holding a medium and a plurality of cells, wherein the cells are configured to produce and secrete a cannabinoid synthase; a bioreactor containing a reactant in a reaction mixture comprising a solvent and an amphiphilic compound, the reactant configured to interact with cannabinoid acid synthase to form a first cannabinoid and a second cannabinoid; and a control mechanism configured to control a condition of the bioreactor, wherein the condition of the bioreactor influences a quantity formed of the first cannabinoid relative to a quantity formed of a second cannabinoid, and wherein the first and second cannabinoids are each one a cannabinoid or a cannabinoid analog.

In a preferred embodiment, the bioreactor is a column bioreactor containing nickel, and the cannabinoid acid synthase includes a tag configured to bond to nickel. In some embodiments, the bioreactor is a column bioreactor containing both nickel and another metal.

In one embodiment, the reactant in the system is a compound according to Formula I;

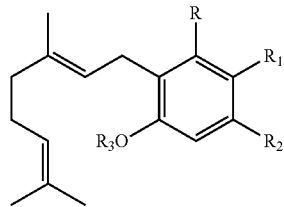

Formula I

Wherein R is selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$ and C$_1$-C$_{10}$ linear or branched alkyl; and R$_a$ and R$_b$ are each independently —H, —OH, —SH, —NH$_2$, (C$_1$-C$_{10}$) linear or branched alkyl, or a C$_3$-C$_{10}$ cycloalkyl.

In one preferred embodiment, the cannabinoid acid synthase is cannabidiolic acid (CBDA) synthase and the first and the second cannabinoids are one or both of cannabidiolic acid and cannabichromenic acid or their analogs.

In another preferred embodiment, the cannabinoid acid synthase is tetrahydrocannabinolic acid (THCA) synthase and the first and the second cannabinoids are one or both of tetrahydrocannabinolic acid and cannabichromenic acid, or their analogs.

Preferably, the cannabinoid acid synthase interacts with the reactant in the bioreactor to form both the first cannabinoid and the second cannabinoid, and the condition of the bioreactor is a function of at least one of pH, solvent, temperature, pressure, and flow rate.

In a preferred embodiment, a change in the condition of the bioreactor is configured to cause a shift from: 1) formation of the first cannabinoid in greater quantities relative to the second cannabinoid to 2) formation of the second cannabinoid in greater quantities relative to the first cannabinoid.

Preferably the solvent in the system is DMSO, and the concentration of DMSO in the reaction mixture is 20% (w/v).

In yet another preferred embodiment, the amphiphilic compound in the system is a surfactant or a cyclodextrin. Preferably, the cyclodextrin is α-cyclodextrin, β-cyclodextrin or γ-cyclodextrin. Even more preferably, the cyclodextrin is sulfobuthylether β-cyclodextrin sodium salt or randomly methylated β-cyclodextrin, and the concentration of cyclodextrin in the reaction mixture is between 2 and 28 mg/ml. Most preferably, the concentration of cyclodextrin in the reaction mixture is 8 mg/ml.

In one aspect of the invention, the amphiphilic compound is cyclodextrin and the mass:mass ratio of cyclodextrin to the compound of Formula I is 28:1 (w/w), or the molar ratio of cyclodextrin to the compound of Formula I is 7.3:1. In a preferred embodiment, 98% of the compound of Formula I in the system is converted into one or more cannabinoids or cannabinoid analogs within two hours.

In a preferred aspect of the invention, the cannabinoid acid synthase in the system is CBDA synthase and the change in the condition of the bioreactor comprises modifying the pH of the reaction mixture in a range between 3.8 and 7.2. Preferably, the method produces CBDA, CBCA, or CBDA and CBCA in different ratios as described above.

In another preferred embodiment, the cannabinoid acid synthase is THCA synthase and the change in the condition of the bioreactor comprises modifying the pH of the reaction mixture in a range between 3.8 and 7.2. Preferably, the method produces THCA, CBCA, or THCA and CBCA in different ratios as described above.

In yet another embodiment, the invention provides a method for producing at least one cannabinoid or cannabinoid analog, that includes the steps of: providing cannabigerol, a cannabinoid acid synthase, and a reaction mixture comprising a solvent and an amphiphilic compound via an automated delivery system; reacting the cannabigerol with the cannabinoid acid synthase in the reaction mixture; adding a solvent via the automated delivery system to cease the reaction; removing the solvent; and recovering the at least one cannabinoid or cannabinoid analog produced by the reaction. Preferably, the reaction mixture comprises DMSO and the cannabinoid acid synthase is CBDA synthase or THCA synthase. Even more preferably, the step of reacting the cannabigerol with the cannabinoid acid synthase comprises controlling the pH of the reaction mixture via a controller. Thus, in a preferred aspect of the invention, the method further comprises controlling the pH of the reaction mixture to produce a predetermined quantity of at least a first cannabinoid or first cannabinoid analog and controlling the pH of the reaction mixture to produce the predetermined quantity of the first cannabinoid or first cannabinoid analog and a predetermined quantity of a second cannabinoid or second cannabinoid analog. In a preferred embodiment, the first cannabinoid or first cannabinoid analog is THCA or CBDA and the second cannabinoid or second cannabinoid analog is CBCA. In another preferred embodiment, the first cannabinoid or first cannabinoid analog is THCA or CBDA and the second cannabinoid or second cannabinoid analog is CBCA.

In another embodiment, the invention provides a method for producing at least one cannabinoid or cannabinoid analog, that comprises: reacting cannabigerol with cannabinoid acid synthase in a reaction mixture comprising a solvent and an amphiphilic compound; adding a solvent to cease the reaction; removing the solvent; and recovering the cannabinoid or cannabinoid analog produced by the reaction. In a preferred aspect of the invention, the step of reacting the cannabigerol with the cannabinoid acid synthase comprises controlling the pH of the reaction mixture. Preferably, the pH of the reaction mixture is controlled by adjusting the pH of the reaction mixture to achieve a predetermined ratio of a first cannabinoid or first cannabinoid analog to a second cannabinoid or second cannabinoid analog. Even more preferably, the reaction mixture comprises DMSO and the cannabinoid acid synthase is CBDA synthase or THCA synthase. In one embodiment, the first cannabinoid or first cannabinoid analog is THCA or CBDA and the second cannabinoid or second cannabinoid analog is CBCA.

In an additional embodiment, the invention provides an apparatus that comprises an automated supply system configured to deliver a first automated supply of cannabigerol, a cannabinoid acid synthase, and a reaction mixture comprising a solvent and an amphiphilic compound; a bioreactor configured to receive the first supply and permit reaction of the cannabigerol and cannabinoid acid synthase in the reaction mixture, and a second automated supply of a solvent so as to cease the reaction; and an extractor configured to remove the solvent and recover at least a first cannabinoid or cannabinoid analog. The apparatus may further comprise a controller configured to adjust at least one property of the reaction mixture so as to produce the first cannabinoid or first cannabinoid analog and a second cannabinoid or second cannabinoid in a predetermined ratio. The controller may be also configured to determine a first quantity of the first cannabinoid or first cannabinoid analog and a second quantity of a second cannabinoid or second cannabinoid analog, and adjust at least one property of the reaction mixture so as to produce the first quantity of the first cannabinoid or first cannabinoid analog and the second quantity of a second cannabinoid or second cannabinoid. Preferably, the reaction mixture comprises DMSO and the cannabinoid acid synthase is CBDA synthase or THCA synthase. In a preferred aspect of the invention, the first cannabinoid or first cannabinoid analog is THCA or CBDA and the second cannabinoid or second cannabinoid analog is CBCA.

In yet another embodiment, the invention provides an apparatus for producing tetrahydrocannabinolic acid (THCA) and cannabichromenic acid (CBCA) or cannabidiolic acid (CBDA) and cannabichromenic acid (CBCA) in different ratios comprising: a bioreactor comprising an automated supply system configured to deliver (a) a first automated supply of cannabigerol, a cannabinoid acid synthase, and a reaction mixture comprising a solvent and an amphiphilic compound, wherein the solvent is one or more of dimethyl sulfoxide (DMSO), dimethyl formamide (DMF) and iso-propoyl alcohol and the concentration of the solvent in the reaction mixture is between 5% and 30% (w/v), and wherein the amphiphilic compound is a surfactant or a cyclodextrin and the concentration of the amphiphilic compound in the reaction mixture is between 2 and 28 mg/ml; and (b) a second automated supply of solvent to cease the reaction; an extractor configured to remove the solvent and recover tetrahydrocannabinolic acid (THCA) and cannabichromenic acid (CBCA) or cannabidiolic acid (CBDA) and cannabichromenic acid (CBCA) from the reaction mixture; and a controller configured to modify the pH of the reaction mixture to produce tetrahydrocannabinolic acid (THCA) and cannabichromenic acid (CBCA) or cannabidiolic acid (CBDA) and cannabichromenic acid (CBCA) in different ratios, and adjust the concentration of the amphiphilic compound in the reaction mixture to affect the conversion rate of cannabigerolic acid (CBGA) into tetrahydrocannabinolic acid (THCA) and cannabichromenic acid (CBCA) or into cannabidiolic acid (CBDA) and cannabichromenic acid (CBCA) in different ratios. In a preferred embodiment, the cannabinoid acid synthase is tetrahydrocannabinolic acid synthase (THCA synthase) or cannabidiolic acid synthase (CBDA synthase). In one aspect of the invention, the cannabinoid synthase is immobilized on a solid support. In another aspect of the invention, the cannabinoid synthase is a recombinant cannabinoid synthase, and the apparatus further comprises a system to produce the recombinant cannabinoid synthase in large scale. Preferably, the pH is in the range from about 3.8 to about 8.0.

In a preferred aspect of the invention, the solvent is one or more of dimethyl sulfoxide (DMSO), dimethyl formamide (DMF) and iso-propyl alcohol, and the concentration of the solvent in the reaction mixture is between 5% and 30% (w/v). In another preferred aspect of the invention, the amphiphilic compound is a surfactant or a cyclodextrin. The cyclodextrin can be α-cyclodextrin, β-cyclodextrin or γ-cyclodextrin. In one aspect of the invention, the cyclodextrin is sulfobuthylether β-cyclodextrin sodium salt or randomly methylated β-cyclodextrin, and the concentration of cyclodextrin in the reaction mixture is between 2 and 28 mg/ml. Preferably, the concentration of cyclodextrin in the reaction mixture is 8 mg/ml.

In one embodiment, the tetrahydrocannabinolic acid (THCA) and cannabichromenic acid (CBCA) or cannabidiolic acid (CBDA) and cannabichromenic acid (CBCA) are single enantiomers with an enantiomeric purity of at least 95%.

In one aspect of the invention, the cannabinoid synthase is THCA synthase and the amphiphilic compound is cyclodextrin. Preferably, the mass:mass ratio of cyclodextrin to cannabigerolic acid (CBGA) is 28:1 or the molar ratio of cyclodextrin to cannabigerolic acid (CBGA) is 7.3:1. In a preferred aspect of the invention, the apparatus produces tetrahydrocannabinolic acid (THCA) and cannabichromenic acid (CBCA) in the following ratios:

| pH | THCA | CBCA |
|---|---|---|
| 4 | 1 | 0 |
| 5 | 2.33 | 1 |
| 6 | 1 | 5.67 |
| 7 | 0 | 1 |

Preferably, 98% of the cannabigerolic acid CBGA is converted into tetrahydrocannabinolic acid (THCA) and cannabichromenic acid (CBCA) within two hours.

In a different aspect of the invention, the cannabinoid acid synthase is CBDA synthase and the amphiphilic compound is cyclodextrin. Preferably, the mass:mass ratio of cyclodextrin to the cannabigerolic acid (CBGA) is 11:1 or the molar ratio of cyclodextrin to the cannabigerolic acid (CBGA) is 4:1. In a preferred aspect of the invention, the apparatus produces cannabidiolic acid (CBDA) and cannabichromenic acid (CBCA) in the following ratios:

| pH | CBDA | CBCA |
|---|---|---|
| 4.2 | 2.5 | 1 |
| 5 | 1.13 | 1 |
| 5.2 | 1 | 1.17 |
| 5.4 | 1 | 2.45 |
| 5.8 | 1 | 6.14 |
| 6.2 | 1 | 28.13 |
| 6.8 | 0 | 0 |

Preferably, 98% of the cannabigerolic acid (CBGA) is converted into cannabidiolic acid (CBDA) and cannabichromenic acid (CBCA) within two hours.

The foregoing general description and the detailed description are exemplary and explanatory and are intended to provide further explanation of the invention as claimed. For detailed understanding of the invention, reference is made to the following detailed description of the preferred embodiments, taken in conjunction with the accompanying drawing. Other objects, advantages and novel features will be readily apparent to those skilled in the art from the following detailed description of the invention.

DETAILED DESCRIPTION OF THE INVENTION

Figure 1:
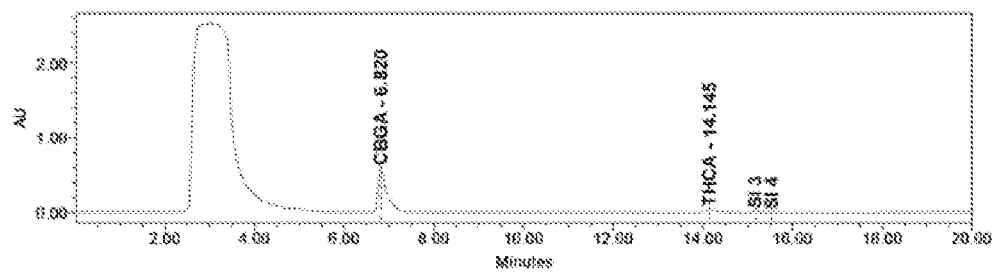
FIG. 1 illustrates the effect of 10% DMSO and no cyclodextrin on THCA synthase activity. 100 µl THCA synthase in crude fermentation supernatant (10× concentrated) were reacted with 50 µl 2 mg/ml CBGA in 350 µl citrate buffer at pH 4.85. Peaks (from left to right): #1 CBGA (86.51%), #2 THCA (10.4%), #3 CBCA (3.09%).
Figure 2:
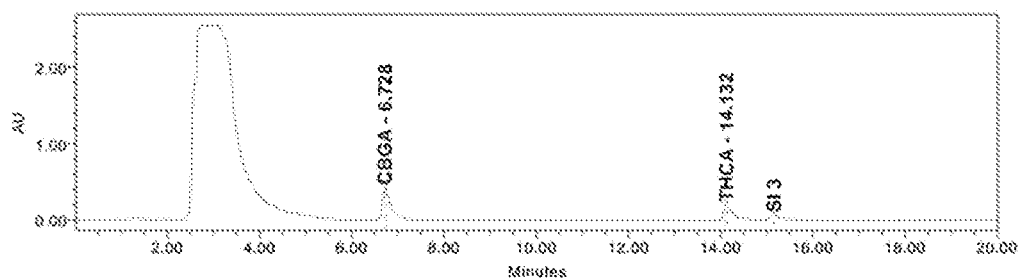
FIG. 2 illustrates the effect of 20% DMSO and no cyclodextrin on THCA synthase activity. 100 µl THCA synthase in crude fermentation supernatant (10× concentrated) were reacted with 50 µl 2 mg/ml CBGA in 300 µl citrate buffer at pH 4.85 in the presence of 50 µl DMSO. Peaks (from left to right): #1 CBGA (54.18%), #2 THCA (32.39%), #3 CBCA (13.43%).

The present invention provides a system and methods for large scale simultaneous enzymatic production of different cannabinoids or cannabinoid analogs, as well as methods for cloning, expressing and purifying enzymes that catalyze large scale simultaneous synthesis of THCA, CBDA, CBCA or analogs thereof under various pH, temperature and aqueous/lipophilic conditions.

Definitions

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "alkyl" refers to a straight or branched chain, saturated hydrocarbon having the indicated number of carbon atoms. For example, ($C_1$-$C_{10}$) alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkenyl" refers to a straight or branched chain unsaturated hydrocarbon having the indicated number of carbon atoms and at least one double bond. Examples of a ($C_2$-$C_{10}$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" refers to a straight or branched chain unsaturated hydrocarbon having the indicated number of carbon atoms and at least one triple bond. Examples of a ($C_2$-$C_{10}$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 3- to 14-member monocyclic, bicyclic, tricyclic, or polycyclic aromatic hydrocarbon ring system. Examples of an aryl group include naphthyl, pyrenyl, and anthracyl. An aryl group can be unsubstituted or optionally substituted with one or more substituents as described herein below.

The terms "alkylene," "alkenylene," and "arylene," alone or as part of another substituent, means a divalent radical derived from an alkyl, cycloalkyl, alkenyl, aryl, or heteroaryl group, respectively, as exemplified by —CH$_2$CH$_2$CH$_2$CH$_2$—. For alkylene, alkenyl, or aryl linking groups, no orientation of the linking group is implied.

The term "halogen" and "halo" refers to —F, —Cl, —Br or —I.

The term "heteroatom" is meant to include oxygen (O), nitrogen (N), and sulfur (S).

A "hydroxyl" or "hydroxy" refers to an —OH group.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "cycloalkyl" refer to monocyclic, bicyclic, tricyclic, or polycyclic, 3- to 14-membered ring systems, which are either saturated, unsaturated or aromatic. The heterocycle may be attached via any heteroatom or carbon atom. Cycloalkyl include aryls and hetroaryls as defined above. Representative examples of cycloalky include, but are not limited to, cycloethyl, cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term 'nitrile or cyano" can be used interchangeably and refer to a —CN group which is bound to a carbon atom of a heteroaryl ring, aryl ring and a heterocycloalkyl ring.

The term "amine or amino" refers to an —NR$_c$R$_d$ group wherein R$_c$ and R$_d$ each independently refer to a hydrogen, ($C_1$-$C_5$)alkyl, aryl, heteroaryl, heterocycloalkyl, ($C_1$-$C_5$)haloalkyl, and ($C_1$-$C_6$)hydroxyalkyl group.

The term "alkylaryl" refers to $C_1$-$C_8$ alkyl group in which at least one hydrogen atom of the $C_1$-$C_8$ alkyl chain is replaced by an aryl atom, which may be optionally substituted with one or more substituents as described herein below. Examples of alkylaryl groups include, but are not limited to, methylphenyl, ethylnaphthyl, propylphenyl, and butylphenyl groups.

"Arylalkylene" refers to a divalent alkylene wherein one or more hydrogen atoms in the $C_1$-$C_{10}$ alkylene group is replaced by a ($C_3$-$C_{14}$)aryl group. Examples of ($C_3$-$C_{14}$)aryl-($C_1$-$C_{10}$)alkylene groups include without limitation 1-phenylbutylene, phenyl-2-butylene, 1-phenyl-2-methylpropylene, phenylmethylene, phenylpropylene, and naphthylethylene.

"Arylalkenylene" refers to a divalent alkenylene wherein one or more hydrogen atoms in the $C_2$-$C_{10}$ alkenylene group is replaced by a ($C_3$-$C_{14}$)aryl group.

The term "arylalkynylene" refers to a divalent alkynylene wherein one or more hydrogen atoms in the $C_2$-$C_{10}$ alkynylene group is replaced by a ($C_3$-$C_{14}$)aryl group.

The terms "carboxyl" and "carboxylate" include such moieties as may be represented by the general formulas:

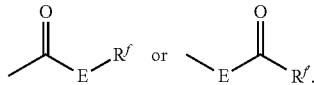

E in the formula is a bond or O and R$^f$ individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

The present invention provides methods for the enzymatic synthesis of cannabinoids or cannabinoid analogs in a cell-free environment. Also described is an apparatus for the ex vivo manufacture of cannabinoids and analogs of cannabinoids. The term "analog" refers to a compound that is structurally related to naturally occurring cannabinoids, but whose chemical and biological properties may differ from naturally occurring cannabinoids. In the present context, analog or analogs refer compounds that may not exhibit one or more unwanted side effects of a naturally occurring cannabinoid. Analog also refers to a compound that is derived from a naturally occurring cannabinoid by chemical, biological or a semi-synthetic transformation of the naturally occurring cannabinoid.

Cannabinoid compounds include, but are not limited to, cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide and nabilone, as well as natural or synthetic molecules that have a basic cannabinoid structure and are modified synthetically to provide a cannabinoid analog.

The present invention also provides methods for the large scale cloning and expression of the enzymes that play a role in the biosynthesis of cannabinoids and for the use of an eukaryotic expression system for the production of biosynthetic enzymes that can be used for the manufacture of cannabinoids and cannabinoid analogs. Yeast as well as eukaryotic and prokaryotic cells are suitable for the cloning and expression of the cannabinoid acid synthase enzymes and include without limitation E. coli, yeast and baculovirus hosts. Thus, the present invention discloses a method for the large-scale production of several cannabinoid acid synthase enzymes including, but not limited to, tetrahydrocannabinolic acid (THCA) synthase and cannabidiolic acid (CBDA) synthase, using the pink Pichia yeast expression system. Accordingly, large scale production of these enzymes can be carried out by transforming yeast with a DNA construct that comprises a gene for a cannabinoid synthase, generating one or more copies of the cannabinoid acid synthase gene and overexpressing a protein encoded by the cannabinoid acid synthase gene.

The nucleic acid sequence of the THCA synthase gene is represented by SEQ ID NO: 1 and encodes a polypeptide sequence set forth in SEQ ID NO: 2. The codon optimized nucleic acid sequence of the THCA synthase gene for Pichia pastoris expression is represented by SEQ ID NO: 3 and encodes a polypeptide sequence set forth in SEQ ID NO: 4, which is the THCA synthase amino acid sequence comprising the alpha secretion sequence of Pichia pastoris. "THCA synthase expression" refers to the biosynthesis of a gene product encoded by SEQ ID NO: 1 or by SEQ ID NO: 3, or a variant, fragment or portion of SEQ ID NO: 1 or SEQ ID NO: 3. "THCA synthase expression" also refers to the biosynthesis of a polypeptide comprising SEQ ID NO: 2 or SEQ ID NO: 4, or a variant, fragment or portion of a polypeptide comprising SEQ ID NO: 2 or SEQ ID NO: 4. "THCA synthase overexpression" denotes an increase in THCA synthase expression. THCA overexpression affects an increase in THCA or CBCA content for a plant or cell in which the overexpression occurs. THCA overexpression refers to upregulated biosynthesis of a gene product encoded by SEQ ID NO: 1 or by SEQ ID NO: 3, or any variant, fragment or portion of SEQ ID NO: 1 or SEQ ID NO: 3.

The nucleic acid sequence of the CBDA synthase gene (codon optimized for *Pichia pastoris* expression) is represented by SEQ ID NO: 5 and encodes a polypeptide sequence set forth in SEQ ID NO: 6. The codon optimized nucleic acid sequence of the CBDA synthase gene for *Pichia pastoris* expression is represented by SEQ ID NO: 7 and encodes a polypeptide sequence set forth in SEQ ID NO: 8, which is the CBDA synthase amino acid sequence comprising the alpha secretion sequence of *Pichia pastoris*. "CBDA synthase expression" refers to the biosynthesis of a gene product encoded by SEQ ID NO: 5 or by SEQ ID NO: 7, or a variant, fragment or portion of SEQ ID NO: 5 or SEQ ID NO: 7. "CBDA synthase expression" also refers to the biosynthesis of a polypeptide comprising SEQ ID NO: 6 or SEQ ID NO: 8, or a variant, fragment or portion of a polypeptide comprising SEQ ID NO: 6 or SEQ ID NO: 8. "CBDA synthase overexpression" denotes an increase in CBDA synthase expression. CBDA overexpression affects an increase in CBDA or CBCA content for a plant or cell in which the overexpression occurs. CBDA overexpression refers to upregulated biosynthesis of a gene product encoded by SEQ ID NO: 5 or by SEQ ID NO: 7, or any variant, fragment or portion of SEQ ID NO: 5 or SEQ ID NO: 7.

The present invention encompasses any nucleic acid, gene, polynucleotide, DNA, RNA, mRNA, or cDNA molecule that is isolated from the genome of a plant species, or produced synthetically, that increases biosynthesis of cannabinoids or cannabinoid analogs. Additionally, expression of such cannabinoid acid synthase sequence produces cannabinoids or cannabinoid analogs in a non-cannabinoid producing cell, including yeast, prokariotic cells and eukariotic cells, such as a non-cannabinoid producing plant cell, a bacteria cell, an insect cell, or an yeast cell. The DNA or RNA may be double-stranded or single-stranded. Single-stranded DNA may be the coding strand, also known as the sense strand, or it may be the non-coding strand, also called the anti-sense strand.

It is understood that THCA synthase and CBDA synthase include the sequences set forth in SEQ ID NOs: 1, 3, 5 and 7, respectively, as well as nucleic acid molecules comprising variants, fragments or portions of SEQ ID NOs: 1, 3, 5 and 7, with one or more bases deleted, substituted, inserted, or added, wherein a variant of anyone of SEQ ID Nos: 1, 3, 5 and 7 codes for a polypeptide with cannabinoid or cannabinoid analog biosynthesis activity. Accordingly, sequences having "base sequences with one or more bases deleted, substituted, inserted, or added" retain physiological activity even when the encoded amino acid sequence has one or more amino acids substituted, deleted, inserted, or added. Physiological activity of the encoded amino acid sequences may be tested using conventional enzymatic assays known in the art. Additionally, multiple forms of THCA synthase and CBDA synthase may exist, which may be due to post-translational modification of a gene product, or to multiple forms of the respective THCA synthase and CBDA synthase. Nucleotide sequences that have such modifications and that code for cannabinoid or cannabinoid analog biosynthesis enzymes are included within the scope of the present invention.

For example, the poly A tail or 5'- or 3'-end, nontranslation regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of cannabinoid acid or cannabinoid acid analog biosynthesis enzyme activity. A modified DNA in this context can be obtained by modifying the DNA base sequences of the invention so that amino acids at specific sites are substituted, deleted, inserted, or added by site-specific mutagenesis, for example, and that still retain cannabinoid acid or cannabinoid acid analog biosynthesis enzyme activity. Cannabinoid acid or cannabinoid acid analog biosynthesis enzyme activity of the encoded amino acid sequences may be assayed as described above.

A cannabinoid or cannabinoid analog biosynthesis sequence can be synthesized ab initio from the appropriate bases, for example, by using an appropriate protein sequence disclosed herein as a guide to create a DNA molecule that, though different from the native DNA sequence, results in the production of a protein with the same or similar amino acid sequence. This type of synthetic DNA molecule is useful when introducing a DNA sequence into a non-plant cell, coding for a heterologous protein, that reflects different (non-plant) codon usage frequencies and, if used unmodified, can result in inefficient translation by the host cell.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

"Exogenous nucleic acid" refers to a nucleic acid, DNA or RNA, which has been artificially introduced into a cell. Such exogenous nucleic acid may be a copy of a sequence which is naturally found in the cell into which it was introduced, or fragments thereof.

In contrast, "endogenous nucleic acid" refers to a nucleic acid, gene, polynucleotide, DNA, RNA, mRNA, or cDNA molecule that is present in the genome of a plant or organism that is to be genetically engineered. An endogenous sequence is "native" to, i.e., indigenous to, the plant or organism that is to be genetically engineered.

"Heterologous nucleic acid" refers to a nucleic acid, DNA or RNA, which has been introduced into a cell which is not a copy of a sequence naturally found in the cell into which it is introduced. Such heterologous nucleic acid may comprise segments that are a copy of a sequence which is naturally found in the cell into which it has been introduced, or fragments thereof.

A "chimeric nucleic acid" comprises a coding sequence or fragment thereof linked to a transcription initiation region that is different from the transcription initiation region with which it is associated in cells in which the coding sequence occurs naturally.

The present application is directed to such nucleic acid molecules which are at least 60%, 65%, 70%, 75%, 80%, 85%, 90%, 95%, 96%, 97%, 98%, 99% or 100% identical to a nucleic acid sequence described in any of SEQ ID NO: 1, 3, 5 and 7. Preferred are nucleic acid molecules which are at least 95%, 96%, 97%, 98%, 99% or 100% identical to the nucleic acid sequence shown in any of SEQ ID NO: 1, 3, 5 and 7. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art and can be determined conventionally using publicly available computer programs such as the BLAST algorithm.

The present invention further provides nucleic acid molecules comprising the nucleotide sequence of SEQ ID NOs: 1, 3, 5 and 7, respectively, which encode an active cannabinoid or cannabinoid analog biosynthesis enzyme, wherein the enzyme has an amino acid sequence that corresponds to SEQ ID NOs: 2, 4, 6, and 8, respectively, or a variant, fragment or portion of anyone of SEQ ID Nos: 2, 4, 6 and 8, and wherein the protein of the invention encompasses amino acid substitutions, additions and deletions that do not alter the function of the cannabinoid or cannabinoid analog biosynthesis enzyme.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art.

The invention contemplates genetically engineering "non-cannabinoid or cannabinoid analog producing cells" with a nucleic acid sequence encoding an enzyme involved in the production of cannabinoids or cannabinoid analogs. Non-cannabinoid or cannabinoid analog producing cells refer to a cell from any organism that does not produce a cannabinoid or cannabinoid analog. Illustrative cells include but are not limited to plant cells, as well as insect, mammalian, yeast, fungal, algal, or bacterial cells.

"Fungal cell" refers to any fungal cell that can be transformed with a gene encoding a cannabinoid or cannabinoid analog biosynthesis enzyme and is capable of expressing in recoverable amounts the enzyme or its products. Illustrative fungal cells include yeast cells such as *Saccharomyces cerivisae* and *Pichia pastoris*. Cells of filamentous fungi such as *Aspergillus* and *Trichoderma* may also be used.

Cannabinoid acid synthase gene sequences may be obtained from a publicly available database. In a preferred aspect of the invention, one or more copies of a cannabinoid acid synthase gene are generated in vivo and the method comprises integrating one or more copies of the cannabinoid acid synthase gene into the genome of a eukaryotic host, such as *Pichia pastoris*, to scale up protein expression. Preferably, the cannabinoid acid synthase gene is codon optimized with an alpha secretion sequence to target protein secretion or tagged with six tandem histidine (SEQ ID NO: 9) residues at the 3' end to facilitate purification. This process comprises linearizing the cannabinoid acid synthase gene by digestion with one or more restriction enzymes; extracting the cannabinoid acid synthase gene by gel extraction; ligating the cannabinoid acid synthase gene into a *Pichia pastoris* plasmid; and electroporating the plasmid into bacterial cells to generate one or more cannabinoid acid synthase gene copy colonies.

Thus, in one embodiment, one or more copies of alpha-CBDA synthase and alpha-THCA synthase sequences, for example, are generated by modification as described above, insertion into pPink-HC vector (Invitrogen®) and transformation into *E. coli* cells. The transformed cells may be stored as agar stabs for future use. Prior to transformation of yeast cells, the vector containing the cannabinoid acid synthase gene of interest (GOI) is isolated from the agar stabs containing the transformed *E. coli* cells, linearized using PmeI or SpeI restriction enzymes and the linearized plasmids thus obtained are electroporated into *Pichia pastoris* pepB deficient mutant cells using PichiaPink™ Yeast Expression Systems (Invitrogen®). Linearization with the restriction enzyme PmeI directs the insert into the AOX1 promoter region of the *Pichia* genome, whereas linearization with the restriction enzyme SpeI directs the insert into the TRP gene.

The transformed yeast cells may be grown on adenine-deficient selective plates and the colonies thus formed may be screened to identify positive transformants. Screening methods include, but are not limited to, color screening methodology. Typically, cells having 6-10 copies of the gene of interest are desired for obtaining large amounts of recombinant protein, for example, about 1.0 g to about 2.0 g of protein per liter of culture.

In one embodiment, individual white colonies of yeast cells carrying the THCA synthase gene or the CBDA synthase gene, for example, are separately cultured in flasks using BMGY medium, followed by induction by growth in BMMY medium, to induce the expression of THCA synthase or CBDA synthase as further described below. Briefly, the medium containing the enzyme in each culture is separated from the cells, reacted with a known amount of substrate and the product is analyzed. Cultures of transformants showing greater than 20% conversion are used for the commercial synthesis of cannabinoids or cannabinoid analogs pursuant to methods of the invention.

The cannabinoid acid synthase enzymes, THCA synthase and CBDA synthase, obtained using the PichiaPink™ Yeast Expression system described above, can be used for the manufacture of cannabinoids or cannabinoid analogs. The cannabinoid or cannabinoid analogs thus obtained are isolated, purified and used as therapeutics. In a further embodiment, the cannabinoids or cannabinoid analogs thus obtained undergo a decarboxylation step.

Cannabinoid synthases according to the invention include, but are not limited to, cannabidiolic acid (CBDA) synthase and tetrahydrocannabinolic acid (THCA) synthase.

In one embodiment, the invention provides a method for producing a cannabinoid or a cannabinoid analog by selecting a Formula I compound and a cannabinoid acid synthase as a catalyst for transforming the Formula I compound to a cannabinoid or a cannabinoid analog.

Formula I

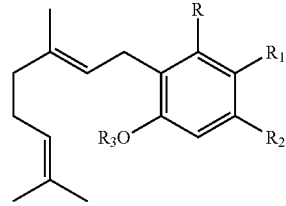

In Formula I, R can be selected from hydroxyl (—OH), halogen, thiol (—SH), or a —$NR_aR_b$ group. Substituent groups $R_1$ and $R_2$ are each independently selected from the group consisting of —H, —$C(O)R_a$, —$OR_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene. Alternatively, $R_1$ and $R_2$ together with the carbon atoms to which they are bonded form a $C_5$-$C_{10}$ cyclic ring. For compounds according to Formula I, $R_3$ is selected from the group consisting of H, —C(O)$R_a$ and $C_1$-$C_{10}$ linear or branched alkyl and $R_a$ and $R_b$ are each independently —H, —OH, ($C_1$-$C_{10}$) linear or branched alkyl, —SH, —NH$_2$, or a $C_3$-$C_{10}$ cycloalkyl.

$R_2$ can be a linear alkylene or a branched alkylene. Exemplary of linear alkylenes include without limitation CH$_3$, $C_2H_5$, $C_3H_7$, $C_4H_9$, $C_5H_{11}$, $C_6H_{13}$, $C_7H_{15}$ and $C_8H_{17}$. Illustrative of branched alkylenes are groups selected from, iso-propyl, sec-butyl, iso-butyl, neopentyl, 2-methyl hexyl, or 2,3-dimethyl hexyl groups. In some embodiments, $R_2$ can be an optionally substituted linear or branched alkylene in which one or more hydrogen atoms is replaced without limitation with a group selected from chlorine, fluorine, bromine, nitro, amino, hydroxyl, phenyl, or benzyl group.

In one embodiment, $R_1$ and $R_2$ together with the ring carbon atoms to which they are bonded form a $C_5$-$C_{10}$ cyclic ring. For such Formula I compounds one or more carbon atoms of the ring can be substituted with a heteroatom selected from oxygen, sulfur or nitrogen.

In another embodiment, $R_2$ is a $C_2$-$C_{10}$ alkenylene and is selected from the group consisting of

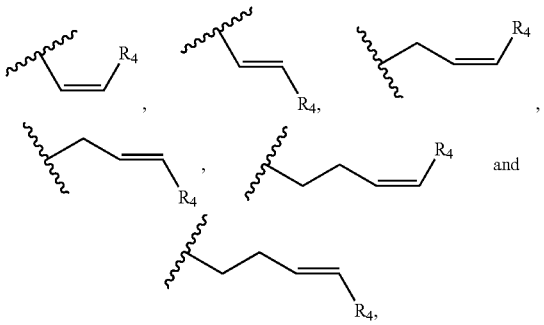

with $R_4$ being a linear or branched alkylene as described above. When $R_2$ is a $C_2$-$C_{10}$ linear or branched alkynylene, $R_2$ can be

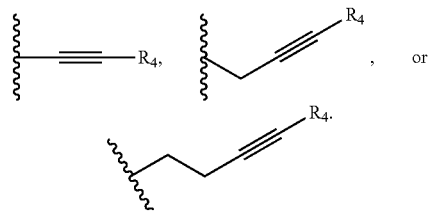

Alternatively, $R_2$ in Formula I is

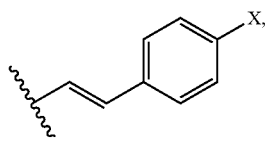

substituent X is a group selected from
—OH, —SH, or N$R_aR_b$ and groups $R_a$ and $R_b$. are as defined above.

In one embodiment, the cannabinoids and/or cannabinoid analogs synthesized according to the invention have a carboxylic acid (—COOH) group as the $R_1$ substituent and may undergo an optional decarboxylation step prior to their use as pharmaceutical or nutraceutical agents. Examples of cannabinoids or cannabinoid analogs having a carboxylic acid group include, but are not limited to, compounds obtained by reacting a compound of Formula I in which R is —OH, $R_1$ is —COOH, $R_2$ is $C_5H_{11}$ and $R_3$ is —H with a cannabinoid acid synthase obtained as described above.

The synthesis, isolation and purification of cannabinoids or cannabinoid analogs can be improved by immobilization of a cannabinoid acid synthase to a solid support, or by encapsulation of the synthase within a liposome. In one aspect, the enzyme is immobilized to a solid support. Without being bound to any theory, the inventors of the present application have unexpectedly discovered that immobilization facilitates use and recovery of the enzyme catalyst, purification of the desired product, and preservation of the enantiomeric excess (ee) of the final product, and provides an overall improvement in the yield of the product. Furthermore, immobilization permits recycling and reuse of the immobilized enzyme which significantly reduces the costs associated with the manufacture of pharmaceutical grade cannabinoids or cannabinoid analogs. Typically, the enantiomeric purity of the cannabinoids and/or cannabinoid analogs produced according to the invention is from about 90% ee to about 100% ee, for instance, a cannabinoid or a cannabinoid analog produced using the inventive methodology can have an enantiomeric purity of about 91% ee, about 92% ee, about 93% ee, about 94% ee, about 95% ee, about 96% ee, about 97% ee, about 98% ee and about 99% ee.

Typically, the enzyme to be immobilized can be absorbed onto a solid support, adsorbed onto a support, covalently linked to a support or can be immobilized onto a solid support through ionic interactions. In one embodiment, the cannabinoid acid synthase is covalently linked to a solid support. Suitable strategies for linking an enzyme to a solid support are well known in the biochemical art and include covalent linkages between an appropriately functionalized support and a side chain of an amino acid group or through covalent linkages using appropriately functionalized linkers or spacers to separate the support from the enzyme. The term "linker" refers to any group that separates the support from the enzyme. Accordingly, a linker is a group that is covalently tethered at one end to a group on the surface of the support and is attached to the enzyme at the other end. Illustrative linkers include ($C_1$-$C_{10}$)alkylene linker polymers of ethylene glycol such as a —(OCH$_2$—CH$_2$)$_n$—O— group, where n is an integer from 0 to 10, —($C_1$-$C_{10}$)alkylene-NH—, —($C_1$-$C_{10}$)alkylenesiloxy, or a —($C_1$-$C_{10}$)alkylene-C(O)—.

Supports suitable for immobilizing enzymes include, but are not limited to, Amberlite resins, Duolite resins, acrylic resins such as Eupergit® C, DEAE-Sephadex and gels made using polyvinyl alcohol.

Cannabinoids exert different physiological properties and are known to lessen pain, stimulate appetite and have been tested as candidate therapeutics for treating a variety of disease conditions such as allergies, inflammation, infection, epilepsy, depression, migraine, bipolar disorders, anxiety disorder, and glaucoma. The physiological effects exerted by cannabinoids is affected by their ability to stimulate or deactivate the cannabinoid receptors, for instance the CB1, CB2 and CB3 receptors. Accordingly, the present invention provides the means to modulate cannabinoid receptor activity and their pharmaceutical properties by modifying the cannabinoid and/or cannabinoid analog binding interactions and the orientation of a ligand within the cannabinoid receptors active site by determining the nature and orientation of substituent groups attached to the cannabinoids and/or cannabinoid analogs produced according to the invention.

Thus, in one embodiment the invention provides a method for the manufacture of cannabinoids and cannabinoid analogs that have structurally distinct and diverse substituent groups attached to a central core and thus exhibit different pharmaceutically beneficial properties. Structural diversity is accomplished by contacting an appropriately substituted Formula III compound with a Formula IV compound in the presence of an enzyme, such as GPP olivetolate geranyltransferase (a polyketide synthase), to produce a compound of Formula II. Scheme 1 below structurally illustrates the protocol for synthesizing a Formula II compound pursuant to this embodiment.

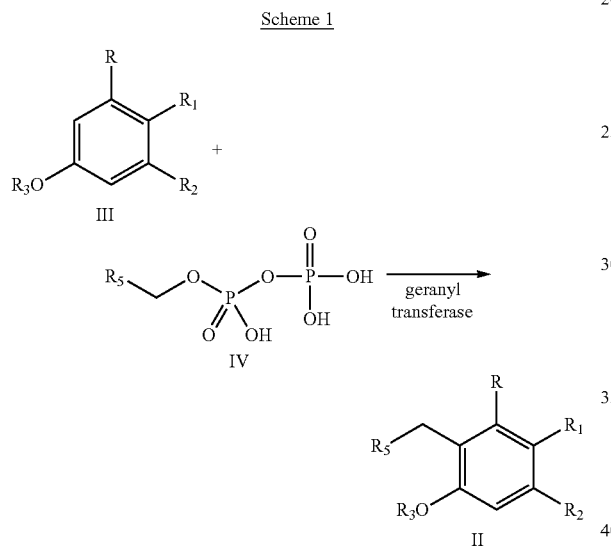

Different compounds of Formula II that serve as substrates for the manufacture of cannabinoids and/or cannabinoid analogs according to the invention may be obtained by varying the nature and type of substituent groups at R, $R_1$, $R_2$, $R_3$ and $R_5$, in the compounds of Formulas III and IV. According to this embodiment, therefore, different cannabinoids and/or cannabinoid analogs may be obtained by reacting a compound of Formula II with a cannabinoid acid synthase, for example, THCA synthase or CBDA synthase obtained as described above, followed by isolation and decarboxylation of the obtained product to give a cannabinoid or a cannabinoid analog.

In Formula III, R can be selected from hydroxyl (—OH), halogen, thiol (—SH), or a —$NR_aR_b$ group. Substituents $R_1$ and $R_2$ are each independently selected from the group consisting of —H, —C(O)$R_a$, —O$R_a$, an optionally substituted linear or branched ($C_1$-$C_{10}$)alkylene, an optionally substituted linear or branched ($C_2$-$C_{10}$)alkenylene, an optionally substituted linear or branched ($C_2$-$C_{10}$)alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene.

In certain embodiments $R_1$ and $R_2$ together with the carbon atoms to which they are bonded form a $C_5$-$C_{10}$ cyclic ring and $R_3$ is selected from the group consisting of H, —C(O)$R_a$ and $C_1$-$C_{10}$ linear or branched alkyl.

$R_5$ in Formula IV can be a linear or branched ($C_1$-$C_{10}$) alkylene, a linear or branched ($C_2$-$C_{10}$)alkenylene, a linear or branched ($C_2$-$C_{10}$)alkynylene, —C(O)— ($C_1$-$C_{10}$)alkylene, —C(O)—($C_2$-$C_{10}$)alkenylene and —C(O)— ($C_2$-$C_{10}$) alkynylene. For Formulae II, III and IV compounds any alkylene, alkenylene, alkynylene, aryl, arylalkylene, or cycloalkyl group can be further substituted with one or more groups selected from the group consisting of —OH, halogen, —$NR_bR_c$, —C(O)$R_a$, —C(O)$NR_bR_c$, ($C_1$-$C_{10}$)alkyl, —CN, ($C_1$-$C_4$)alkoxy, ($C_1$-$C_4$)haloalkyl, and ($C_1$-$C_4$)hydroxyalkyl with $R_a$, $R_b$ and $R_c$ each independently being selected from —H, —OH, or ($C_1$-$C_{10}$) linear or branched alkyl, —SH, —$NH_2$, or a $C_3$-$C_{10}$ cycloalkyl.

According to one embodiment, $R_5$ in Formula IV can be a ($C_2$-$C_{10}$)alkenylene selected from

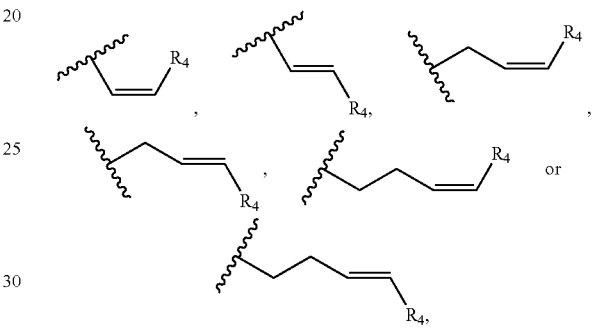

with $R_4$ being a linear alkylene selected from the group consisting of $CH_3$, $C_2H_5$, $C_3H_7$, $C_4H_9$, $C_5H_{11}$, $C_6H_{13}$, $C_7H_{15}$ and $C_8H_{17}$. For certain Formula IV compounds $R_5$ is

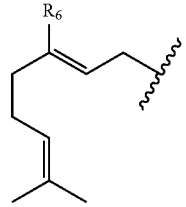

and group $R_6$ is selected from ($C_1$-$C_{10}$)alkylene, ($C_2$-$C_{10}$) alkenylene, —OH, —SH, $NO_2$, F, Cl, Br, —$NH_2$, or a —$NHR_a$ where $R_a$ is as defined above.

A recombinant cannabinoid acid synthase obtained by overexpressing a protein encoded by a recombinant cannabinoid acid synthase gene as described above is reacted with a substrate according to Formula I or with a substrate according to Formula II as described above in a reaction mixture comprising a solvent and an amphiphilic compound to produce one or more cannabinoids or cannabinoid analogs. The cannabinoids or cannabinoid analogs thus formed are isolated from the reaction mixture and optionally decarboxylated. Preferably, the recombinant cannabinoid acid synthase is a recombinant CBDA synthase or a recombinant THCA synthase obtained by the method described above. In a preferred aspect of the invention, the solvent in the reaction mixture is a non-aqueous solvent, such as dimethyl sulfoxide (DMSO), dimethyl formamide (DMF), or isopropoyl alcohol. The concentration of the solvent in the reaction mixture may vary between 10% and 30% (v/v). The inventors of the present application have unexpectedly discovered that the concentration of the non-aqueous solvent in the reaction mixture affects the rate of the reaction as well as the ratio between the different cannabinoid products. Thus, the table below shows that in a reaction driven by the THCA synthase, the presence of DMSO in a concentration of 20% (v/v) in the reaction mixture increases the rate of the reaction by 2.5-fold and causes the reaction to produce THCA and CBCA in a ratio of 5:1, whereas the presence of DMSO in a concentration of 10% (v/v) in the reaction mixture produces THCA and CBCA in a ratio of 10:1. Accordingly, in a preferred aspect of the invention, the non-aqueous solvent in the reaction mixture is DMSO and the concentration of DMSO in the reaction mixture is most preferably 20% (v/v).

TABLE 1

Effect of DMSO Concentration on Reaction Rate and Products

| DMSO | Rate of Reaction | THCA:CBCA |
|------|------------------|-----------|
| 0%   | 1X               |           |
| 10%  | 1.2X             | 10:1      |
| 20%  | 2.5X             | 5:1       |
| 25%  | —                | 1:1       |
| 30%  | 0.3X             |           |

In an additional preferred embodiment of the invention, the reaction mixture also comprises an amphiphilic compound. Preferably, the amphiphilic compound is a surfactant or a cyclodextrin. Surfactants may include, but are not limited to, cationic surfactants, ionic surfactants and anionic surfactants. Most preferably, the reaction mixture contains a cyclodextrin.

Cyclodextrins are natural cyclic oligosaccharides consisting of six or more 1-4 linked α-anhydro-glucose moieties, which may be produced from starch through an enzymatic reaction. Cyclodextrins are classified according to the number of glucose units as α-cyclodextrin (six units), β-cyclodextrin (seven units) and γ-cyclodextrin (eight units). The structure of the cyclodextrin is shown below:

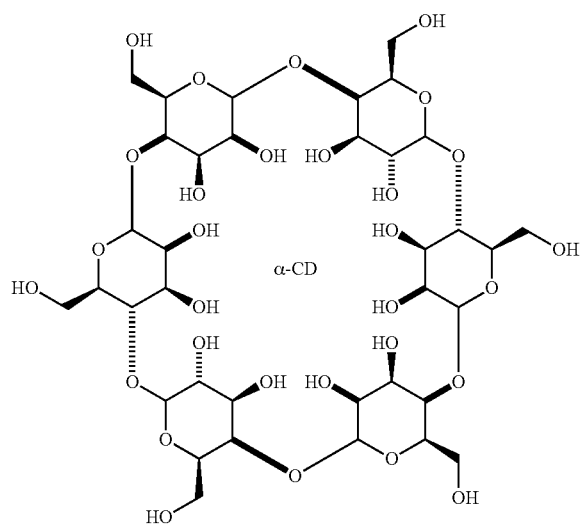

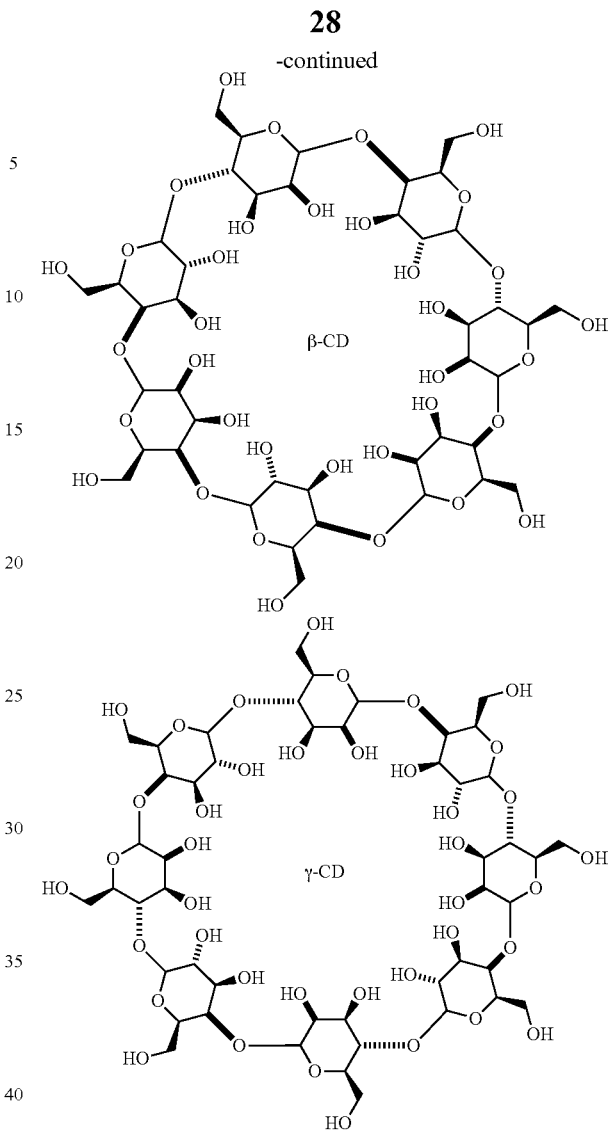

The secondary hydroxyl groups on the exterior side of the cyclodextrin molecule are hydrophilic, whereas the primary hydroxyl groups form the hydrophobic central cavity. Without being bound to any theory, it is believed that the hydrophobic central cavity in cyclodextrin incorporates the substrate in the reaction mixture as a guest molecule and the complex thus formed protects and stabilizes the substrate, although no covalent or ionic bonds are formed.

The inventors of the present application have unexpectedly discovered that the concentration of cyclodextrin in the reaction mixture affects the conversion rate of the substrate into the products as well as the ratio between the different products of the reaction, as shown in the table below. shows the effect of cyclodextrin concentration in the reaction mixture on CBDA synthase reaction at pH 4.85.

As shown in the table below, increasing the concentration of cyclodextrin from 0 mg/ml to 28 mg/ml in the CBDA synthase enzyme reaction increases the conversion rate of CBGA to CBDA and CBCA, with the highest conversion rates seen when cyclodextrin concentrations were 8 mg/ml and 12 mg/ml (20% higher conversion rate comparing to no cyclodextrin added to the reaction).

Addition of cyclodextrin also slightly changes the ratio of CBDA:CBCA at pH 5. The highest CBDA:CBCA ratio (CBDA:CBCA 1.41:1) was observed when cyclodextrin concentration was 20 mg/ml and the lowest CBDA:CBCA ratio (CBDA:CBCA 1.04:1) was observed when cyclodextrin concentration was 16 mg/ml.

TABLE 2

Effect of Cyclodextrin on CBDA Synthase Reaction Conversion Rate and Product Ratio

| Cyclodextrin concentration | Conversion rate | CBDA:CBCA ratio | FIG. |
|---|---|---|---|
| 0 mg/ml | 40% | 1.13:1 | 11 |
| 2 mg/ml | 57% | 1.24:1 | 12 |
| 4 mg/ml | N/A | N/A | N/A |
| 8 mg/ml | 61% | 1.28:1 | 13 |
| 12 mg/ml | 60% | 1.33:1 | 14 |
| 16 mg/ml | 50% | 1.04:1 | 15 |
| 20 mg/ml | 53% | 1.41:1 | 16 |
| 28 mg/ml | 45% | 1.24:1 | 17 |

The cyclodextrin may be α-cyclodextrin, β-cyclodextrin or γ-cyclodextrin. In some embodiments, the cyclodextrin is sulfobuthylether β-cyclodextrin sodium salt or randomly methylated β-cyclodextrin. When present in the reaction mixture, the cyclodextrin is in a concentration of from about 0.001 to about 30 mg/ml. Preferably, the concentration of cyclodextrin in the reaction mixture is between 2 and 28 mg/ml. In a most preferred embodiment, the concentration of cyclodextrin in the reaction mixture is 8 mg/ml.

As shown in the table below and in FIGS. 11-17, with no cyclodextrin, increasing the amount of DMSO from 10% to 20% increased the conversion of CBGA from 13.5% to 45.8% overnight, and changed the ratio of THCA:CBCA from 3.33:1 to 2.24:1. Including cyclodextrin in the reaction with 10% DMSO, increased the conversion of CBGA to 89.7% and gave a ratio of 4.2:1 THCA:CBCA. Increasing the concentration of cyclodextrin to 40% or 60% gave the same results.

| Condition | CBGA | THCA | CBCA | THCA:CBCA | FIG. ID |
|---|---|---|---|---|---|
| 10% DMSO, no cyclodextrin | 86.51% | 10.40% | 3.0900% | 3.37:1 | 1 |
| 20% DMSO, no cyclodextrin | 54.18% | 32.39% | 13.43% | 2.41:1 | 2 |
| 10% DMSO, 20% cyclodextrin | 10.33% | 72.37% | 17.300% | 4.20:1 | 3 |
| 10% DMSO, 40% cyclodextrin | 11.50% | 72.08% | 16.42% | 4.39:1 | 4 |
| 10% DMSO, 60% cyclodextrin | 10.36% | 73.98% | 15.65% | 4.73:1 | 5 |

The cannabinoids or cannabinoid analogs produced according to the methods of the invention aremay be single enantiomers with an enantiomeric purity of at least 95%, and preferably of at least 99%.

The inventors of the present application have also unexpectedly discovered that the pH of the reaction mixture affects the ratio between the different cannabinoid products obtained. Accordingly, in a preferred embodiment, the pH of the reaction mixture is modified to obtain the cannabinoid products and/or cannabinoid analog products in the desired ratio.

Thus, when reacted with a compound of Formula I according to the invention, THCA synthase may produce tetrahydrocannabinol (THCA), cannabichromene (CBCA), THCA and CBCA, or analogs thereof in different ratios, according to the pH of the reaction. Preferably, the reaction is performed at a pH in a range between 3.8 and 7.2, and the method produces THCA, CBCA, or THCA and CBCA in a ratio as shown in the following table at each specified pH:

TABLE 3

Effect of pH on THCA Synthase Reaction Products

| pH | THCA | CBCA |
|---|---|---|
| 4 | 1 | 0 |
| 5 | 2.33 | 1 |
| 6 | 1 | 5.67 |
| 7 | 0 | 1 |

In summary, changing the pH of the THCA synthase enzyme reaction affects the products. At pH 4 THCA is the only product. At pH 5 the ratio of THCA:CBCA is 2.33:1. At pH 6 the ratio is reversed and the product mix is THCA:CBCA 1:5.67. At pH 7 CBCA is the only product. Under these conditions, 98% of the compound of Formula I is converted into one or more cannabinoids or cannabinoid analogs within two hours.

Similarly, when reacted wit a compound of Formula I, CBDA synthase may produce cannabidiol (CBDA), cannabichromene acid (CBCA), CBDA and CBCA, or analogs thereof in different ratios, according to the pH of the reaction. Preferably, the reaction is performed at a pH in a range between 3.8 and 7.2, and the method produces CBDA, CBCA, or CBDA and CBCA in a ratio as shown in the following table at each specified pH:

TABLE 4

Effect of pH on CBDA Synthase Reaction Products

| pH | CBDA | CBCA |
|---|---|---|
| 4.2 | 2.5 | 1 |
| 5 | 1.13 | 1 |
| 5.2 | 1 | 1.17 |
| 5.4 | 1 | 2.45 |
| 5.8 | 1 | 6.14 |
| 6.2 | 1 | 28.13 |
| 6.8 | 0 | 0 |

In summary, changing the pH of the CBDA synthase enzyme reaction affects the products. At pH 4.2 the CBDA:CBCA ratio is 2.5:1. At pH 5 the ratio of CBDA:CBCA is 1.13:1. At pH 6.8 there is no product forming from CBDA synthase enzyme reaction. Under these conditions, 70% of the compound of Formula I is converted into one or more cannabinoids or cannabinoid analogs within two hours.

The invention also provides a method of producing one or more cannabinoids or cannabinoid analogs according to Formula II

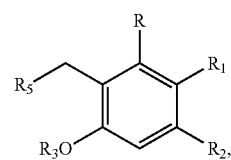

wherein the method comprises the steps of: (a) reacting a compound according to Formula III with a compound according to Formula IV;

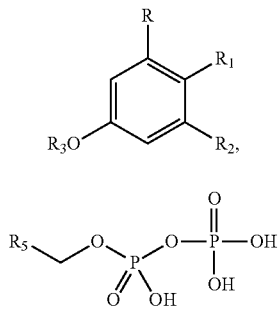

III

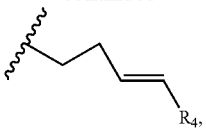

IV in the presence of an enzyme that catalyzes the reaction of the Formula III and Formula IV compounds to form a Formula II compound; (b) reacting the compound of Formula II with a cannabinoid acid synthase in a reaction mixture comprising a solvent and an amphiphilic compound as described above to produce one or more cannabinoids or cannabinoid analogs; (c) isolating from the reaction mixture one or more cannabinoids or cannabinoid analogs produced in step (b); and (e) optionally decarboxylating the one or more cannabinoids or cannabinoid analogs isolated in step (c). R in Formula III may be selected from —OH, halogen, —SH, or a —NR$_a$R$_b$ group; R$_1$ and R$_2$ are each independently selected from the group consisting of —H, —C(O)R$_a$, —OR$_a$, an optionally substituted linear or branched (C$_1$-C$_{10}$)alkylene, an optionally substituted linear or branched (C$_2$-C$_{10}$)alkenylene, an optionally substituted linear or branched (C$_2$-C$_{10}$)alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring; R$_3$ is selected from the group consisting of H, —C(O)R$_a$ and C$_1$-C$_{10}$ linear or branched alkyl. R$_5$ in Formula IV may be selected from the group consisting of a linear or branched (C$_1$-C$_{10}$)alkylene, a linear or branched (C$_2$-C$_{10}$)alkenylene, a linear or branched (C$_2$-C$_{10}$)alkynylene, —C(O)—(C$_1$-C$_{10}$)alkylene, —C(O)—(C$_2$-C$_{10}$)alkenylene and —C(O)—(C$_2$-C$_{10}$)alkynylene; wherein any alkylene, alkenylene, alkynylene, aryl, arylalkylene, or cycloalkyl group is further substituted with one or more groups selected from the group consisting of —OH, halogen, —NR$_b$R$_c$, —C(O)R$_a$, —C(O)NR$_b$R$_c$, (C$_1$-C$_{10}$) alkyl, —CN, (C$_1$-C$_4$)alkoxy, (C$_1$-C$_4$)haloalkyl, and (C$_1$-C$_4$) hydroxyalkyl; and R$_a$, R$_b$ and R$_c$ are each independently —H, —OH, —SH, —NH$_2$, (C$_1$-C$_{10}$) linear or branched alkyl, or a C$_3$-C$_{10}$ cycloalkyl.

In one embodiment, R$_5$ is a (C$_2$-C$_{10}$)alkenylene selected from the group consisting of

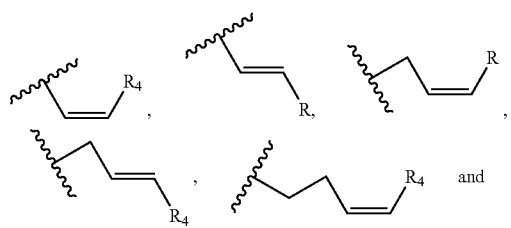

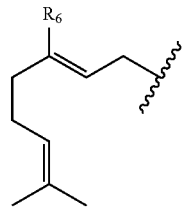

and R$_4$ is a linear alkylene selected from the group consisting of CH$_3$, C$_2$H$_5$, C$_3$H$_7$, C$_4$H$_9$, C$_5$H$_{11}$, C$_6$H$_{13}$, C$_7$H$_{15}$ and C$_8$H$_{17}$. In a preferred aspect of the invention, R$_5$ is

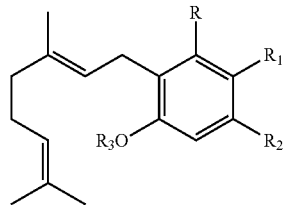

and R$_6$ is selected from (C$_1$-C$_{10}$)alkylene, (C$_2$-C$_{10}$)alkenylene, —OH, —SH, NO$_2$, F, Cl, Br, —NH$_2$, or —NHR$_a$.

In yet another embodiment, the invention provides a method for producing a tetrahydrocannabinol, cannabichromene, or both tetrahydrocannabinol and cannabichromene, or their analogs, wherein the method comprises the steps of: (a) selecting a compound according to Formula I;

Formula I (b) reacting the compound of Formula I with a tetrahydrocannabinolic acid (THCA) synthase in a reaction mixture comprising a solvent and an amphiphilic compound as described above; (c) modifying at least one property of the reaction mixture, such as the pH of the reaction, the nature and/or concentration of the non-aqueous solvent and/or the concentration of an amphiphilic compound, such as cyclodextrin, to obtain a tetrahydrocannabinol, a cannabichromene, or both tetrahydrocannabinol and cannabichromene, or their analogs as products as described above; (d) isolating tetrahydrocannabinol, cannabichromene, or both tetrahydrocannabinol and cannabichromene, or their analogs from the reaction mixture; and (e) decarboxylating the tetrahydrocannabinol, cannabichromene, or both tetrahydrocannabinol and cannabichromene, or their analogs. R in Formula I may be selected from —OH, halogen, —SH, or a —NR$_a$R$_b$ group; R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a $C_5$-$C_{10}$ cyclic ring; $R_3$ is selected from the group consisting of H, —C(O)$R_a$ and $C_1$-$C_{10}$ linear or branched alkyl; and $R_a$ and $R_b$ are each independently —H, —OH, —SH, —NH$_2$, ($C_1$-$C_{10}$) linear or branched alkyl, or a $C_3$-$C_{10}$ cycloalkyl.

In a different embodiment, the invention also provides a method for producing a cannabidiol, cannabichromene, or both cannabidiol and cannabichromene, or their analogs comprising the steps of: (a) selecting a compound according to Formula I;

Formula I

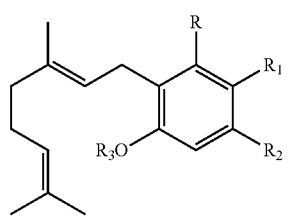

(b) reacting the compound of Formula I with a cannabinodiolic acid (CBDA) synthase in a reaction mixture comprising a solvent and an amphiphilic compound as described above; (c) modifying at least one property of the reaction mixture, such as the pH of the reaction, the nature and/or concentration of the non-aqueous solvent and/or the concentration of an amphiphilic compound, such as cyclodextrin, to obtain a cannabidiol, a cannabichromene, or both cannabidiol and cannabichromene, or their analogs as products; (d) isolating cannabidiol, cannabichromene, or both cannabidiol and cannabichromene, or their analogs from the reaction mixture; and (e) decarboxylating the cannabidiol, cannabichromene, or both cannabidiol and cannabichromene, or their analogs. R in Formula I may be selected from —OH, halogen, —SH, or a —NR$_a$R$_b$ group; $R_1$ and $R_2$ are each independently selected from the group consisting of —H, —C(O)$R_a$, —OR$_a$, an optionally substituted $C_1$-$C_{10}$ linear or branched alkylene, an optionally substituted $C_2$-$C_{10}$ linear or branched alkenylene, an optionally substituted $C_2$-$C_{10}$ linear or branched alkynylene, an optionally substituted $C_3$-$C_{10}$ aryl, an optionally substituted $C_3$-$C_{10}$ cycloalkyl, ($C_3$-$C_{10}$)aryl-($C_1$-$C_{10}$)alkylene, ($C_3$-$C_{10}$)aryl-($C_2$-$C_{10}$)alkenylene, and ($C_3$-$C_{10}$)aryl-($C_1$-$C_{10}$)alkynylene, or $R_1$ and $R_2$ together with the carbon atoms to which they are bonded form a $C_5$-$C_{10}$ cyclic ring; $R_3$ is selected from the group consisting of H, —C(O)$R_a$ and $C_1$-$C_{10}$ linear or branched alkyl; and $R_a$ and $R_b$ are each independently —H, —OH, —SH, —NH$_2$, ($C_1$-$C_{10}$) linear or branched alkyl, or a $C_3$-$C_{10}$ cycloalkyl. Thus, the present inventors have devised methods that produce different cannabinoids and/or cannabinoid analogs in the desired ratio and in a controlled manner, by varying the pH of the reaction, the nature and/or concentration of the non-aqueous solvent and/or the concentration of an amphiphilic compound, such as cyclodextrin, in the reaction mixture.

Apparatus and Methods for Producing Cannabinoids or Cannabinoid Analogs

Figure 7:
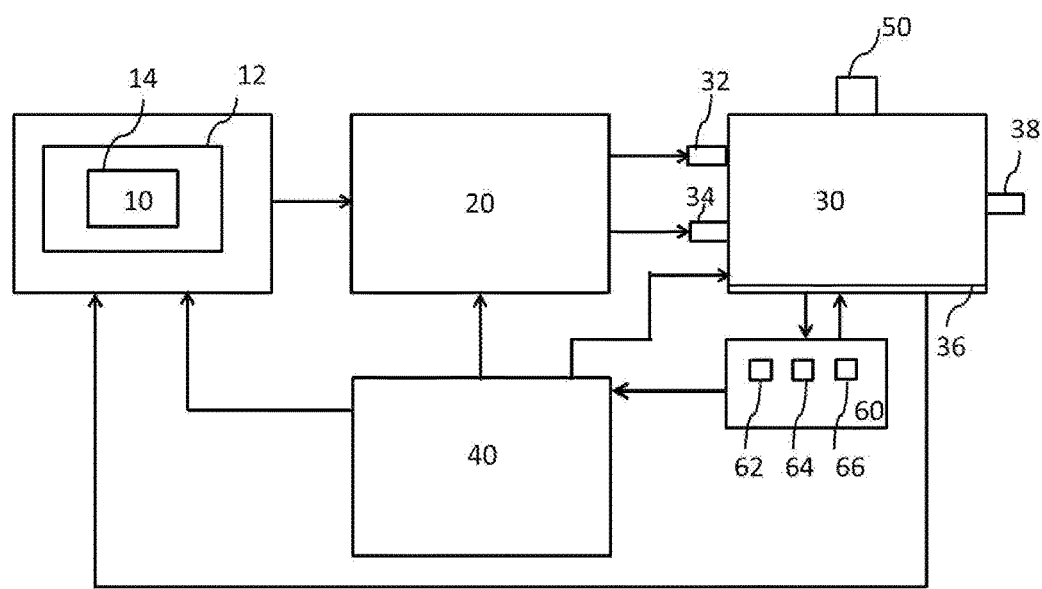
FIG. 7 is a block diagram of a system for producing cannabinoids and/or cannabinoid analogs.

An apparatus or system is provided for producing one or more cannabinoids or cannabinoid analogs according to the methods of the invention. The apparatus may comprise a fermentor, a filter, a bioreactor, and a control mechanism. FIG. 7 depicts an apparatus 100 configured to produce at least one cannabinoid and/or at least one cannabinoid analog according to an embodiment. As shown in FIG. 7, the apparatus 100 includes a fermentor 10, a filter 20, a bioreactor 30, and a control mechanism (controller) 40. The fermentor 10 holds cell culture medium 12 and a plurality of cells 14. The cells 14 produce and secrete a cannabinoid acid synthase. The cells 14 grown in the fermentor 10 for the manufacture of a cannabinoid acid synthase can be yeast, prokaryotic or eukaryotic cells that have been genetically modified to include a nucleic acid sequence or a gene that encodes a cannabinoid acid synthase protein. In certain embodiments, the nucleic acid sequence that encodes a cannabinoid acid synthase protein is modified to include a yeast alpha secretion sequence at its 5' end and to incorporate a 6-residue histidine tag (SEQ ID NO: 9) at its 3' end. The addition of the yeast alpha secretion sequence permits secretion of the cannabinoid acid synthase protein into the medium 12 used for eukaryotic cell growth. Following production of cannabinoid acid synthase in the fermentor 10, the supernatant comprising the medium 12 and cells 14 (and cannabinoid synthase), is transported along a pathway to the filter 20.

The filter 20 may filter the supernatant to at least partially separate the cells 14 from the medium 12 containing the expressed enzyme. Typically, the filter 20 separates at least 80% of the total cells 14 from the medium. In some embodiments, the filter 20 separates at least 85%, at least 90%, at least 91%, at least 92%, at least 93%, at least 94%, at least 95%, at least 96%, at least 97%, at least 98%, at least 99%, or 100% of the total cells 14 from the medium 12. Following filtration, the cells 14 are transported back to the fermentor 10. In one embodiment, the filter 20 can be a filtration and purification system that includes multiple filters and reservoirs to purify the cannabinoid synthase.

After passing through the filter 20, the cannabinoid acid synthase flows into the bioreactor 30 and enters the bioreactor 30 through an inlet 32. The bioreactor 30 also includes an inlet 34 for reactants, such as the substrate CBGA or other substrates according to the Formula I compound described above.

In some embodiments, the bioreactor 30 can be a column bioreactor having a support 36. The support 36 may be a solid support that is impregnated with divalent metal ions or a support whose surface is functionalized with divalent metal ions. Typically, sepharose, agarose or other biopolymers are used as supports for binding divalent metal ions such as nickel, cobalt, magnesium and manganese. Such supports have a strong affinity for the histidine tag that is present on the expressed cannabinoid acid synthase and can be used to sequester the synthase and separate it from other non-essential proteins and debris that may interfere or impede cannabinoid synthesis.

The bioreactor 30 used for synthesizing cannabinoids is configured for batch and continuous synthetic processes to permit commercial production of pharmaceutically useful cannabinoids. In one embodiment, the bioreactor 30 is configured for batch synthesis in which the composition of the medium, concentration of the enzyme and substrate are fixed at the beginning of the process and not allowed to change during catalysis. Synthesis is terminated when the concentration of the desired product in the medium of the bioreactor 30 reaches a predetermined value or the concentration of substrate falls below a predetermined level, such as to a level where there is no detectable catalytic conversion of substrate to product.

In one embodiment, therefore, the His-tagged cannabinoid acid synthase is sequestered onto a nickel containing resin support within the bioreactor 30 prior to the introduction of a known amount of substrate, for example, cannabigerolic acid (CBGA), or a compound of Formula I or Formula II into the bioreactor 30. In an alternate embodiment, CBGA or a compound of Formula I or Formula II can be present within the bioreactor 30 having a nickel resin support prior to the introduction of the medium containing a cannabinoid acid synthase into the bioreactor 30.

The progress of the reaction within the bioreactor 30 can be monitored periodically or continuously. For instance, an optical monitoring system 50 may be utilized to detect the concentration of product in the medium within the bioreactor as a function of time. Alternatively, the decrease in the concentration of substrate can be monitored to signal termination of synthesis. The cannabinoid product thus produced can be readily recovered from the medium using standard solvent extraction or chromatographic purification methods. The monitoring system 50 may be part of or may interact with a control mechanism 40 (a controller) described further below.

An alternative to the batch process mode is the continuous process mode in which a defined amount of substrate and medium are continuously added to the bioreactor 30 while an equal amount of medium containing the cannabinoid product is simultaneously removed from the bioreactor 30 to maintain a constant rate for formation of product. The medium can enter the bioreactor 30 through the inlet 32 and exit the bioreactor through an outlet 38.

The conditions of the bioreactor can be controlled using a control mechanism 40. The control mechanism 40 may be coupled to the bioreactor 30 or, alternatively, may interact with the bioreactor 30 wirelessly or remotely. The control mechanism 40 may also be used to control the conditions of the fermentor 10, such the oxygen level, agitation, pH, and feed rate. The control mechanism 40 may also control the flow of materials (e.g. by controlling at least one pump) into and out of the fermentor 10, filter 20, and bioreactor 30. In some embodiments, the control mechanism 40 is configured to control the conditions of at least one of the fermentor 10, the filter 20 and the bioreactor 30 based on information obtained from the optical monitoring system 50.

The control mechanism 40 may include a processing circuit having a processor and memory device. The processor and memory are configured to complete or facilitate the various processes and functions described in the present application, such as controlling the pH, temperature, and pressure of the bioreactor 30, or altering the flow rate of medium into or out of the bioreactor 30. In some embodiments, for facilitating the control of pH, temperature, pressure and flow rate, the control mechanism 40 may be configured to communicate with at least one sensor in a sensor suite 60. The sensor suite 60 may include a pH sensor 62, a temperature sensor 64, and a pressure sensor 66. The control mechanism 40 may include a proportional-integral-derivative (PID) controller for feedback-based control. The control mechanism 40 may be further configured to regulate the flow rate of materials into and out of the fermentor 10, the filter 20 and the bioreactor 30 via pulse width modulation (PWM) techniques.

Figure 10:
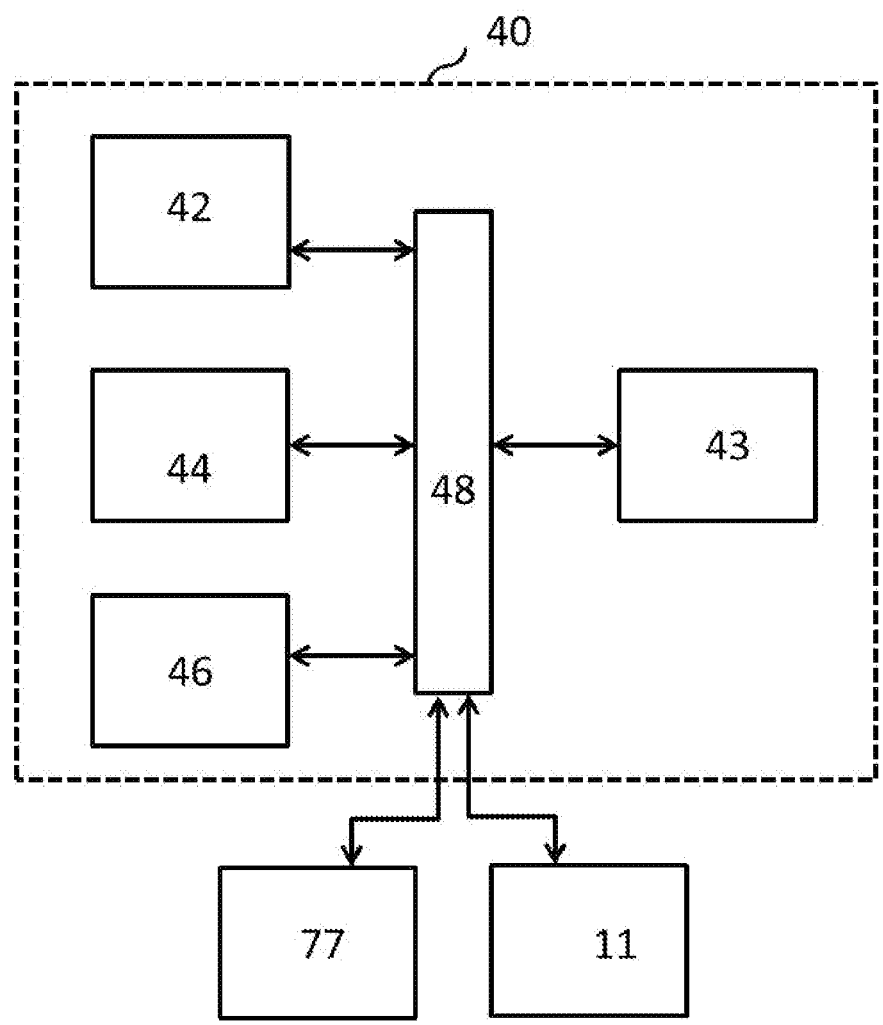
FIG. 10 is a block diagram of a controller.
Figure 11:
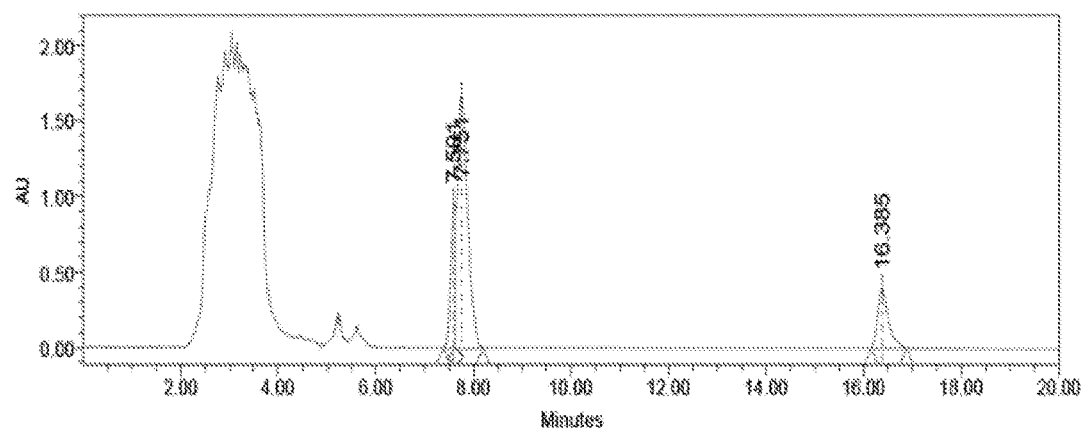
FIG. 11 illustrates the effect of 0 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8. Peaks (Left to right): CBDA (17.99%), CBGA (65.72%), CBCA (16.30%).
Figure 12:
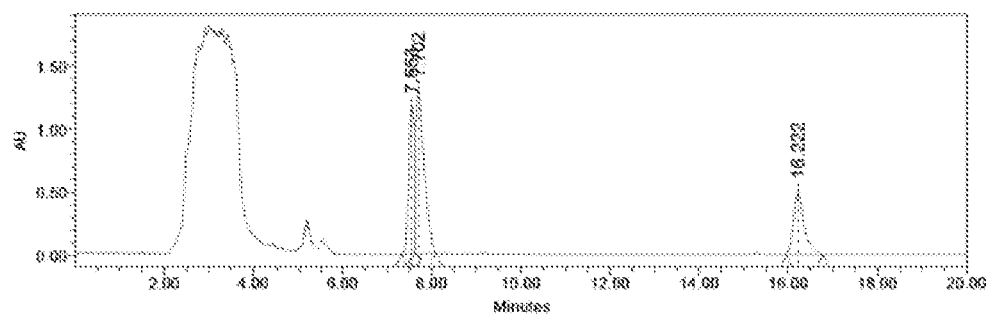
FIG. 12 illustrates the effect of 2 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8 containing 2 mg/ml cyclodextrin. Peaks (Left to right): CBDA (29.53%), CBGA (47.40%), CBCA (23.08%).
Figure 13:
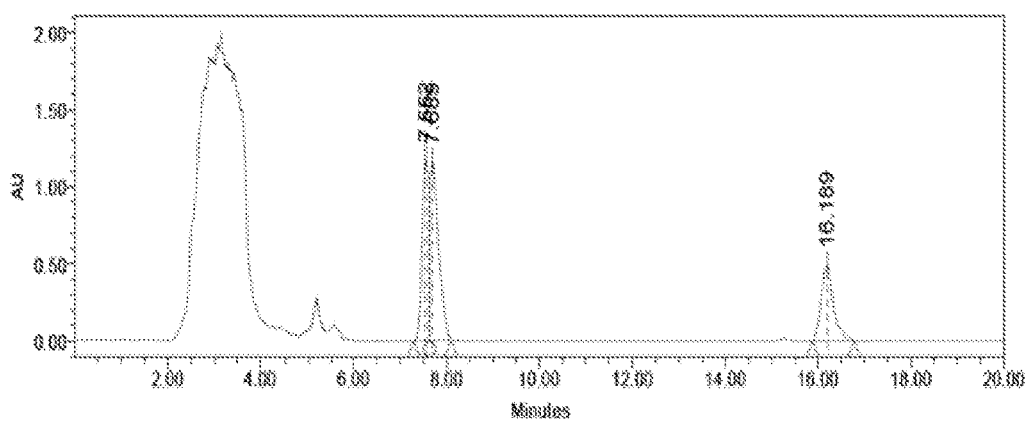
FIG. 13 illustrates the effect of 8 mg/ml cyclodextrin on CBDA synthase reaction conversion rate and product ratio. 50 µl of 10× concentrated fermentation supernatant were reacted with 8.25 µl of 5 mg/ml CBGA in 175 µl of citrate buffer pH 4.8 containing 8 mg/ml cyclodextrin. Peaks (Left to right): CBDA (33%), CBGA (41.98%), CBCA (25.02%).
Figure 14:
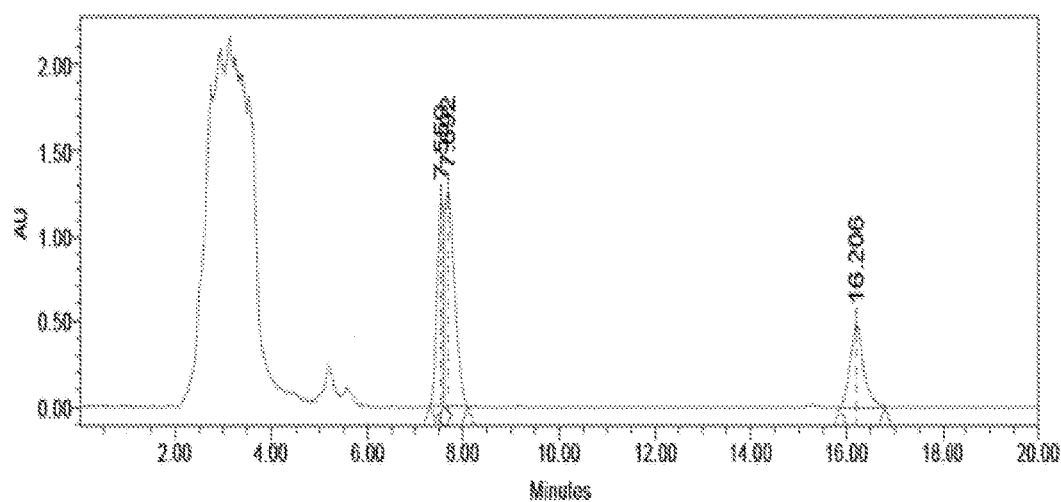
FIG. 14 illustrates the effect of 12 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8 containing 12 mg/ml cyclodextrin. Peaks (Left to right): CBDA (30.63%), CBGA (45.22%), CBCA (24.15%).
Figure 15:
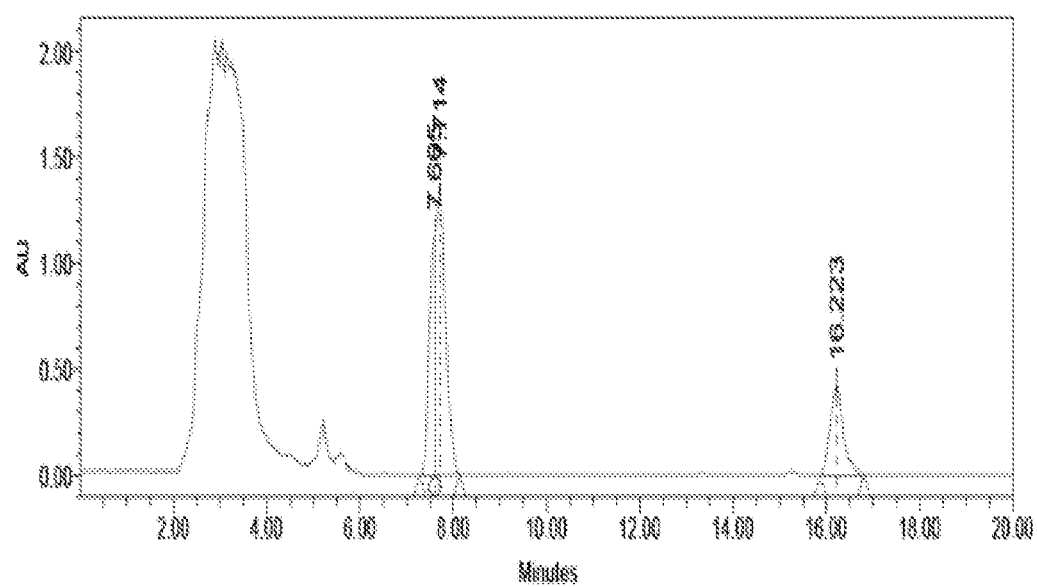
FIG. 15 illustrates the effect of 16 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8 containing 16 mg/ml cyclodextrin. Peaks (Left to right): CBDA (28.54%), CBGA (49.63%), CBCA (21.84%).
Figure 16:
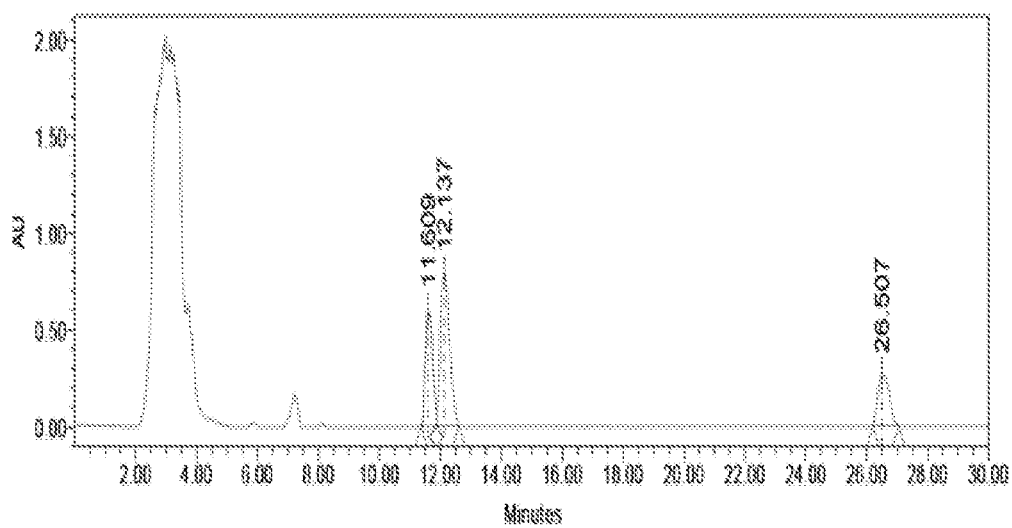
FIG. 16 illustrates the effect of 20 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8 containing 20 mg/ml cyclodextrin. Peaks (Left to right): CBDA (29.05%), CBGA (50.04%), CBCA (20.91%).
Figure 17:
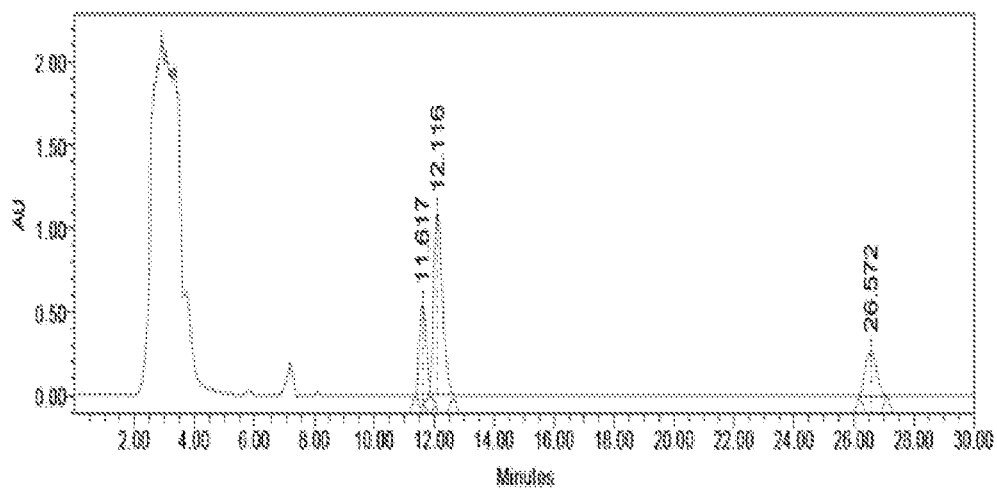
FIG. 17 illustrates the effect of 28 mg/ml cyclodextrin on CBDA synthase reaction conversion rate and product ratio. 50 µl of 10× concentrated fermentation supernatant were reacted with 25 µl of 5 mg/ml CBGA in 175 µl of citrate buffer pH 4.8 containing 28 mg/ml cyclodextrin. Peaks (Left to right): CBDA (22.09%), CBGA (59.60%), CBCA (18.32%).

FIG. 10 depicts the control mechanism 40. The control mechanism 40 includes a processor 43 coupled to a communication bus 48. The control mechanism 40 further includes a main memory 42, such as a random access memory (RAM) or other dynamic storage device, coupled to the bus 48 for storing information, and configured to store instructions to be executed by the processor 43. The main memory 42 is further configured to store temporary variables and intermediate information during execution of instructions by the processor 43. The control mechanism 40 may additionally include a read only memory (ROM) 44 or other static storage device connected to the bus 48 for storing information and instructions. Additionally, a storage device 46, such as a solid state device, magnetic disk or optical disk, may be coupled to the bus 48 for persistently storing information and instructions.

Furthermore, the control mechanism 40 may be coupled (via the bus 48) to a display 77, such as a liquid crystal display, or active matrix display, for displaying information to a user. In some embodiments, an input device 11, such as a keyboard, may also be coupled to the bus 48 for communicating information, and to convey commands to the processor 43. In some embodiments, the input device 11 has a touch screen display.

Figure 8:
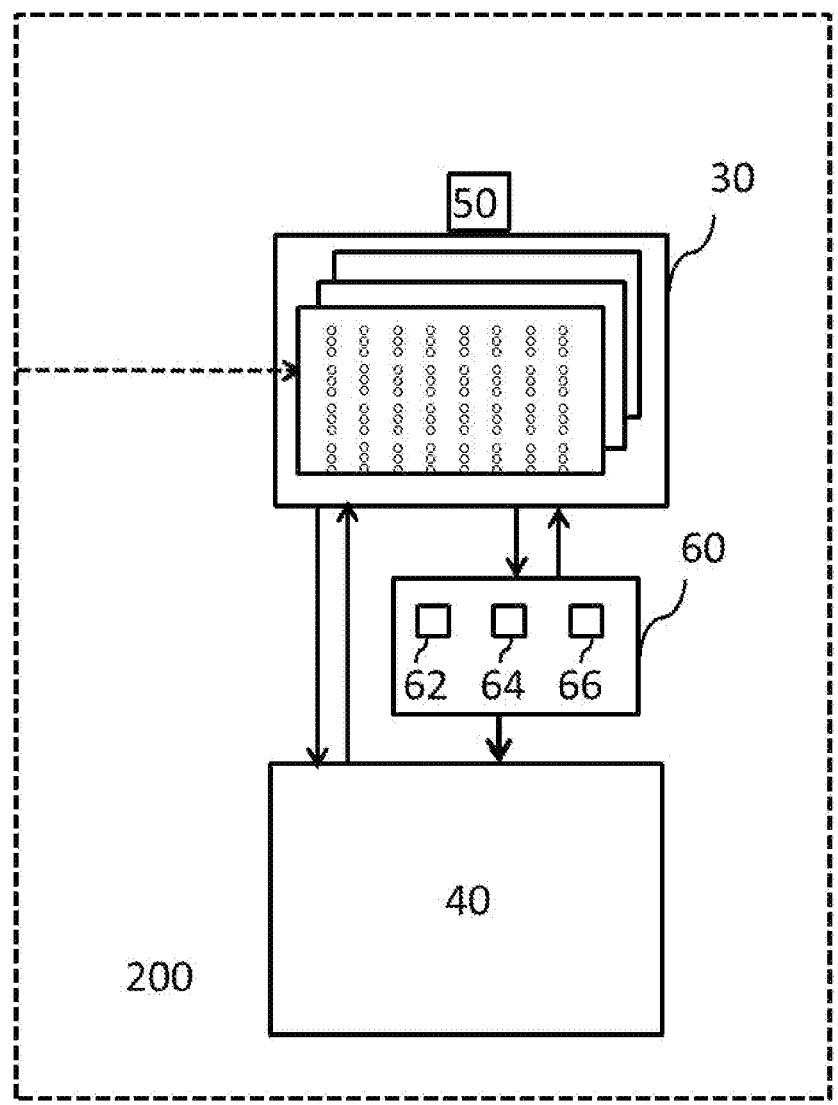
FIG. 8 is a block diagram of a system for producing cannabinoids and/or cannabinoid analogs.

In some embodiments, the bioreactor 30 is not a column reactor. Instead, as shown in FIG. 8, the bioreactor 30 comprises a plurality of microtiter plates and is provided in a system 200. The system 200, like the system 100, includes a controller 40 configured to control the bioreactor 30. The controller 40 may control the environmental conditions of the bioreactor 30 and the supply of materials to the bioreactor 30, and may also control operations performed on the plurality of microtiter plates.

Figure 9:
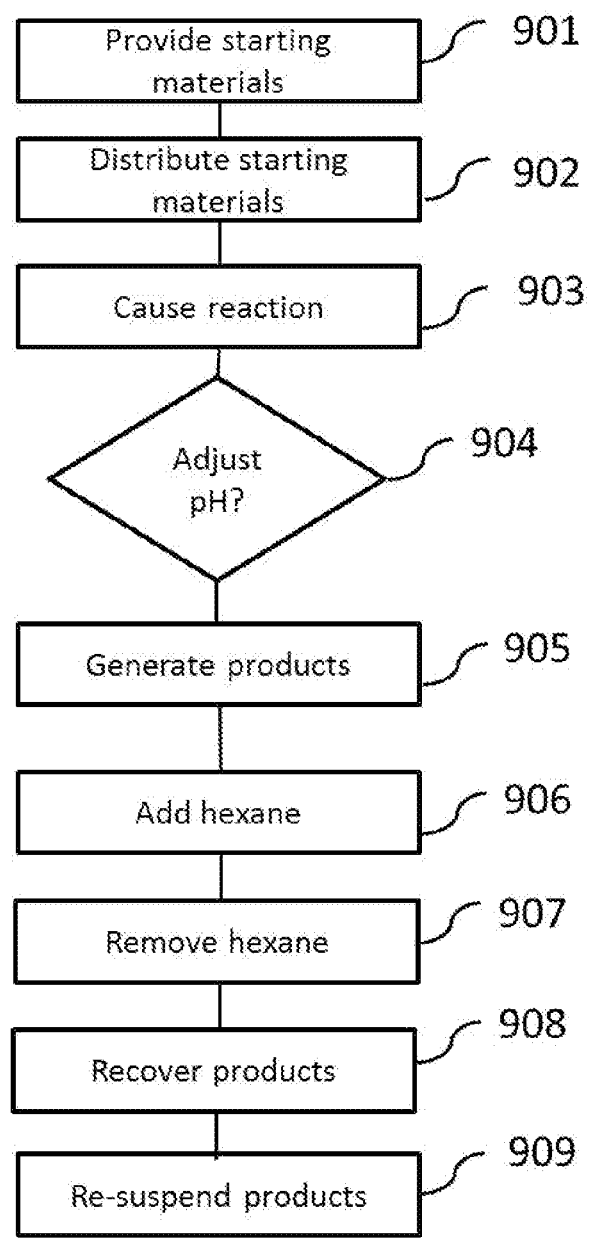
FIG. 9 is a flow diagram illustrating a method for producing cannabinoids.

In some embodiments, each of the microtiter plates of system 200 has 96 wells. In other embodiments, at least one microtiter plate has 384 wells, 1,536 wells, 3456 wells, or 9600 wells. In embodiments with 96-well microtier plates, an enzyme reaction may take place in each of the 96 wells. The reaction in each well make take place in a volume of 0.5 ml or in a volume exceeding 0.5 mL. The apparatus described above are configured to produce cannabinoid acids or cannabinoid acid analogs, specifically, THCA and CBCA or CBDA and CBCA, by implementing the techniques described below in reference to FIG. 9. FIG. 9 illustrates an automated method (900) for producing cannabinoids or cannabinoid analogs according to an embodiment. The method includes providing cannabinoid CBG, DMSO, and a cannabinoid biosynthetic enzyme in each of the wells (901). The cannabinoid biosynthetic enzyme may be, for example, THCA synthase. The cannabinoid biosynthetic enzyme is produced by the fermentor 10 by growing yeast transformed with a gene encoding THCA synthase, as described above. The cannabinoid CBG, on the other hand, is chemically synthesized. The cannabinoid CBG, the DMSO and cannabinoid biosynthetic enzyme may be considered to be the 'starting materials' introduced into the bioreactor to ultimately yield at least one cannabinoid or cannabinoid analog. The cannabinoid CBG, DMSO, and cannabinoid biosynthetic enzyme may be provided in each of the wells via automatic pipetting. In other words, an apparatus such as the systems 100, 200 may comprise mechanized componentry that may be controlled, for example, by the control mechanism 40, so as to deliver an appropriate amount of at least one of the cannabinoid CBG, DMSO, and cannabinoid biosynthetic enzyme to each well of the microtiter plates. In some implementations, operations shown in FIG. 9 may be performed iteratively by virtue of such automation. For example, an automated dispensing system or automated delivery system may be configured as a supply mechanism and used to deliver at least one of CBG, DMSO and THCA synthase and a solvent. In some implementations, the systems 100, 200 may be configured with a programmable sample changer configured to automate sample preparation and transfer. The programmable sample changer may be, for example, the Gilson 223 Sample Changer produced by Gilson, Inc. of Middleton, Wis., USA, and may be operable with peristaltic and/or syringe pumps.

The method further includes reacting the cannabinoid CBG and the cannabinoid biosynthetic enzyme such as THCA synthase in the DMSO once these materials are distributed in the wells (902). The method further includes, in some implementations, determining a ratio of THCA to CBCA or a ratio of CBDA to CBCA to be produced by the reaction (903). In some implementations, the control mechanism 40 determines a quantity of THCA and a quantity of CBCA to be produced, or a quantity of CBDA and a quantity of CBCA to be produced. Next, the method includes determining whether the pH of the reaction mixture requires adjusting in order to yield the predetermined ratio of THCA to CBCA or the predetermined ratio of CBDA to CBCA (904). Specifically, the pH may be adjusted by altering the composition of the reaction mixture to obtain a desired ratio of THCA:CBCA or a desired ratio of CBDA:CBCA. The reaction culminates in the production of THCA and CBCA or CBDA and CBCA (905).

The method further includes automatically pipetting a solvent into each well of the microtiter plate (906). The addition of the solvent results in cessation of the reaction. The method additionally includes, following the introduction of the solvent into the wells and cessation of the reaction, recovering cannabinoids or cannabinoid analogs in the solvent layer.

Once the reaction has ceased, the resulting solvent layer is removed (907), and the cannabinoids or cannabinoid analogs are recoverable. More specifically, the cannabinoids or cannabinoid analogs are recoverable from a solvent fraction present in each of the wells via vacuum evaporation or ethanol extraction (908). In some embodiments, a rotary evaporator is used to remove the solvent. The rotary evaporator may be an automated rotary evaporator such as the fully automated POWERVAP® rotary evaporator produced by Genser Scientific Instruments of Rothenburg ob der Tauber, Germany. Upon removal of the solvent, the cannabinoids or cannabinoid analogs are left in the bottoms of the wells. The method further includes re-suspending the cannabinoids or cannabinoid analogs (909). The cannabinoids or cannabinoid analogs may be re-suspended in ethanol, liposomes, or lipid micelles.

The process illustrated in FIG. 9 permits recovery of cannabinoids or cannabinoid analogs that may be readily formulated into pharmaceuticals and marijuana-infused products including beverages, confectionery, and cosmetics, among other examples. The cannabinoids or cannabinoid analogs may be readily purified via HPLC for pharmaceutical applications.

In at least one implementation, 0.5 mg of buffered CBG, buffered THCA synthase or buffered CBDA synthase with or without stabilizer, and DMSO are automatically pipetted into each of a plurality of wells of a microtiter plate. The DMSO that is added may have a final concentration of 20%, in some implementations. The ensuing reaction in each of the plurality of wells generally yields approximately 0.5 mg of cannabinoids when incubated for 2 hours, 4 hours, 12 hours, and 24 hours. Thus, for a microtiter plate including 96 wells, the system 100 produces about 48 mg of cannabinoids. It follows that the amount of cannabinoids produced 'scales up' when a plurality of microtiter plates are used. For example, if 21 microtiter plates are used, each having 96 wells, then 1008 mg (about 1 gram of cannabinoids) may be produced according to the techniques described above. Using 315 microtiter plates produces approximately 150 grams of cannabinoids. In some implementations, volumes greater than 0.5 mg may be used for the reaction mixture.

In some embodiments, the processor of the controller can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described above. The memory device may be or include volatile memory or non-volatile memory. The memory device may include database components, object code components, script components, or any other type of information structure for supporting the various activities and information structures described in the present application. According to one embodiment, the memory device is communicably connected to the processor via the processing circuit and includes computer code for executing (e.g., by the processing circuit and/or processor) one or more processes described herein.

The present disclosure contemplates methods, apparatus and program products on any machine-readable media for accomplishing various operations, such as controlling the conditions of the bioreactor. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The control mechanism may further include additional devices, such as a keyboard and display, to allow a user to interact with the control mechanism to control the conditions of the bioreactor. For example, the display may include a screen to allow a user to monitor changes in pH, temperature, pressure, and flow rate of the bioreactor, or to monitor any other condition of the system for producing cannabinoids or cannabinoid analogs. The present invention is further described by the following examples which are not meant to limit the scope of the claims.

EXAMPLES

A. Molecular Cloning, Screening and Expression of Protein from High Yield Yeast Transformants
1. Restriction Digestion.
THCA α plasmid DNA and CBDA α plasmid DNA were linearized by digesting each plasmid with Pme I or Spe I restriction enzymes at 37° C. for two hours. Linearized plasmids were verified on 0.8% agarose gel by electrophoresis. Qiagen Gel Extraction kit was used to extract the linearized plasmid from the agarose gel and the plasmids were frozen at −20° C. until use.

2. Preparation of Electrocompetent Yeast Cells.

Electrocompetent PichiaPink (pPink) cells were made by inoculating 10 mL of YPD media with a glycerol stock of a genetically engineered Ade2, pep4 knockout pPink yeast strain 2. These cells were grown overnight in a 125 ml baffled flask at 28° C., using a shaker spinning at 270 rpm until the $OD_{600}$ of the culture reached a value of 1.3 units indicating log phase growth. This culture was then added to 100 ml of YPD media and allowed to incubate overnight under the same conditions. The $OD_{600}$ was checked hourly and after a 12 hour incubation period reached a value of 1.3 units.

After reaching log phase growth the cells were transferred to a 500 ml centrifuge tube and spun down for 5 minutes at 4° C. and 2500 rpm. The YPD broth was decanted and 250 ml of sterile ice-cold water was added and the cells re-suspended. The cells were then centrifuged at 4° C., 2500 rpm for another 5 minutes, re-suspended with an additional 250 ml of water to ensure removal of all YPD media and centrifuged under the same conditions again. The water was then decanted and 50 ml of sterile ice-cold water was added and the cells re-suspended and centrifuged under the same conditions. The water was then decanted and 10 ml of sterile, ice-cold 1M sorbitol was added and the cells re-suspended. The suspension was then transferred to a sterile 15 ml conical tube and centrifuged under the same conditions as before. The 1M sorbitol was then decanted, 300 μl of sterile ice-cold 1M sorbitol was added and the cells were re-suspended and placed on ice for use.

3. Electroporation

The previously frozen linearized plasmid DNA was thawed on ice and 80 μl of the electrocompetent pPink cells were added to the tube. This volume was then transferred to a 0.2 cm electroporation cuvette and incubated on ice for 5 minutes. The cuvette was then pulsed at 1640 V, 200Ω, and 25 μF for a total pulse time of approximately 4 minutes. Immediately after pulsing, 1 ml of YPDS media was added to the cuvette and mixed by pipetting. The cuvette was then placed in a 28° C. incubator, without shaking, for 2 hours, after which 300 μl was spread onto fresh PAD plates. The PAD plates were then placed into the 28° C. incubator for approximately 7-10 days and inspected each day for cell growth.

4. Screening

White colonies are indicative of positive expression of the gene of interest, whereas red colonies indicate no expression. All white colonies were selected and re-streaked onto fresh PAD plates and allowed to grow for 3-5 days until individual colonies appeared. A single colony was then used to inoculate 10 ml of BMGY in a 125 ml baffled flask and placed into an incubator overnight shaking at 28° C. and 270 rpm. When the $OD_{600}$ reached 1.2-1.5 (after 1:10 dilution in water) the inoculum was transferred to a 50 ml conical tube and centrifuged at 2500 rpm for 5 minutes. The BMGY was decanted and 1 ml of BMMY was added. The tubes were then covered with air porous tape to allow for sterile air exchange and placed into the shaking incubator at 28° C. and 270 rpm.

After 24 hours 100 μl of the sample were removed and 100 μl of 40% methanol were added. The removed portion was then centrifuged at 12,000 rpm for 5 minutes and the supernatant and pellet were saved as T=1 (day 1) samples. This procedure was then repeated after 48 hours (T=2). After 72 hours (T=3) the remaining sample was harvested as the final time point. The T=3 supernatant was then spun through an Amicon 30 kD protein filter and run on an SDS-PAGE for visualization of protein.

5. Enzymatic Conversion

Samples that had greater than 20% conversion of CBGA to CBDA over 4-24 hours were then scaled up. Briefly, enzymatic conversion reaction was as follows: 25 μl of cell free supernatant from the T=3 samples was incubated for 2 hours at 30° C., with 25 μl of a 1 mg/ml CBGA stock in DMSO in 200 μl of pH 4.8, 100 mM citrate buffer. Reaction yielded a final concentration of CBGA of 0.1 mg/ml at pH 5.0.

For Scale-Up, a single colony was used to inoculate 10 ml of BMGY in a 125 ml baffled flask which was incubated overnight at 28° C. and 270 rpm. The $OD_{600}$ was measured after 24 hours, and once it reached 1.2 the 10 ml suspension was then used to inoculate 90 ml of BMGY in a 1 L baffled flask. The suspension was then allowed to incubate overnight at 28° C. and 270 rpm. When the $OD_{600}$ reached 1.2-1.5 the inoculum was then transferred to a 500 ml centrifuge bottle and pelleted at 2500 rpm for 5 minutes.

The BMGY was decanted and the cell pellet washed with 10 ml of BMMY. After 2 washings the pellet was re-suspended with 10 ml of BMMY, transferred to a 500 ml baffled flask and allowed to incubate overnight at 28° C. and 270 rpm. After 24 hours 1 ml of the sample was removed (T=1) and 1 ml of 40% methanol was added. This was repeated after 48 and after 72 hours the full sample volume was harvested, separated and analyzed.

Table 5 below shows the results of small scale screening samples with greater than 20% conversion of CBGA to THCA that were selected for scale-up.

TABLE 5

Small Scale Screening Samples with Greater than 20% Conversion of CBGA to THCA

| Sample ID | % Conversion of CBGA to THCA in reaction containing 0.1 mg/ml CBGA. |
| --- | --- |
| Spe THC #3 | 20.6 |
| Spe THC #4 | 28.7 |
| Spe THC #22 | 20.6 |
| Spe THC #23 | 18.7 |
| Pme THC #5 | 32.5 |
| Pme THC(2) #1 | 29.1 |
| Pme THC(2) #2A | 27.2 |
| Pme THC(2) #25 | 31.6 |
| Pme THC(2) #36 | 27.7 |
| Pme THC(2) #41 | 32.5 |
| Pme THC(2) #42 | 27.6 |
| Pme THC(2) #46 | 40.7 |
| Pme THC(2) #51 | 26.8 |
| Pme THC(3) #1 | 55.2 |
| Pme THC(3) #11 | 35.0 |
| Pme THC(3) #17 | 69.9 |
| Pme THC(3) #19 | 36.8 |
| Pme THC(3) #20 | 34.3 |

6. Cloning Strategy for Generating Multi-Copy GOI Inserts In Vitro.

An alternate yeast expression system was used to obtain transformed cells having one or more copies of the gene of interest. The multi-copy *Pichia* Expression Kit from Invitrogen was used to construct new plasmids that could generate multi-copy gene inserts in vitro or in vivo.

In Vitro Generation of Multi-Copy Inserts

To generate multi-copy GOI inserts in vitro, the pAO815 vector was used to clone the gene of interest. α-CBDA synthase and α-THCA synthase were cut with EcoR I and Bam HI from pPink-HC plasmid by incubating 100 ng of the pPink-HC vector containing the α-CBDA synthase gene or the α-THCA synthase gene with 1 µl of EcoR I buffer, 1 µl of each restriction enzyme (10 units/µl) and 1 µl of BSA in 20 µl total reaction volume at 37° C. for 2 hr. 100 ng of pAO815 vector was also digested with Eco R I and Bam HI enzymes following the same protocol.

After digestion, the GOI and vectors mixture were run on a 0.8% agarose gel at 95 V for 1 hr. Bands of correct size were excised and extracted from the gel with Invitrogen gel extraction kit. The linearized vector and gene inserts were ligated using T4 DNA ligase protocol from NEB®. Upon ligation, the circular vector containing the gene of interest was transformed into E. coli Top 10 F− cells to harvest plasmid by electroporation at 1500 V, 200Ω and 25 µF for 4 milliseconds. The transformed cells were then mixed with 250 µl of SOC medium (provided with One Shot® Top 10 Electrocomp™ E. coli from Invitrogen) and plated on a LB-Amp100 plate at 37° C. overnight. The next morning, positive colonies were identified with colony PCR protocol with 5' AOX1 and 3'AOX1 primers. Positive colonies containing the gene of interest were grown in liquid LB-Amp100 media overnight at 37° C. The next day plasmid mini-preps were done with Invitrogen's fast prep kit and the concentration of the plasmid was analyzed on 0.8% agarose gel before further amplification.

The recombinant pAO815 plasmid containing the alpha-THCA synthase and alpha-CBDA synthase genes was divided into 2 batches, one batch was used as a vector in which was inserted a second copy of the gene of interest and one batch was used for extracting the alpha-THCA synthase or alpha-CBDA synthase genes. The vector batch was first digested with Bam HI following NEB's single digest protocol. The second batch was digested with Bgl II and Bam HI restriction enzymes. The linearized vector and genes were purified on a 0.8% agarose gel and extracted. The vector and genes were then ligated following NEB's T4 DNA ligase protocol and then transformed into E. coli Top10 F− cells by electroporation as described above. The cells were incubated at 37° C. overnight and then screened for the correct gene insert by PCR. Gene sequences were confirmed by sequencing. The multi-copy plasmids were linearized at the His4 sequence region by restriction enzyme digestion and transformed into competent Pichia pastoris strain G115 (his4, Mut+) cells. The transformed cells were grown on His− plates for screening. Screening was done on His− plates to confirm integration of the plasmid at the His site of the Pichia Pastoris genome. Positive colonies were chosen for methanol induction of protein, time points protein SDS-gel and enzyme assay.

In Vivo Generation of Multi-Copy Inserts

To generate multi-copy GOI inserts in vivo, the pPIC-3.5K vector was used as the backbone to carry and insert one or more copies of the α-CBDA synthase gene or the α-THCA synthase gene into the Pichia pastoris GS115 strain genome. α-CBDA synthase and α-THCA synthase genes were excised out with Pme I and Bam HI from pPink-HC plasmid, separated from the pPink-HC backbone on a 0.8% agarose gel at 95 V for 1 hr and extracted from the gel with Qiagen or Invitrogen gel extraction kit. pPIC-3.5K plasmid was digested by PmeI and BamHi from NEB, run on 0.8% agarose gel and extracted from the gel with Qiagen or Invitrogen gel extraction kit.

The linearized vector and gene inserts were ligated together using Invitrogen T4 DNA ligase protocol from NEB®. Ligated circular recombinant plasmids were electroporated into E. coli Top 10 F− strain and the cells were plated on LB-Amp-100 plates. The plates were incubated were incubated overnight at 37° C. for colonies to form. Colony PCR was applied to verify successful transformation and colonies bearing pPIC-3.5K-alpha-THCA synthase or pPIC-3.5K-alpha-CBDA synthase were re-streaked on new LB-Amp-100 plates to generate more plasmids.

pPIC-3.5K-alpha-THCA synthase and pPIC-3.5K-alpha-CBDA synthase were inserted into GS115 strain by electroporation as described above. The transformed GS115 cells were then plated on YPD-geneticin plates with 0.25 mg/mml-3 mg/ml geneticin to select for one or more THCA synthase gene and CBDA synthase gene copy colonies. Colonies grown on 3 mg/ml YPD-geneticin plates were selected for THCA synthase and CBDA synthase production screening.

Results

Figure 3:
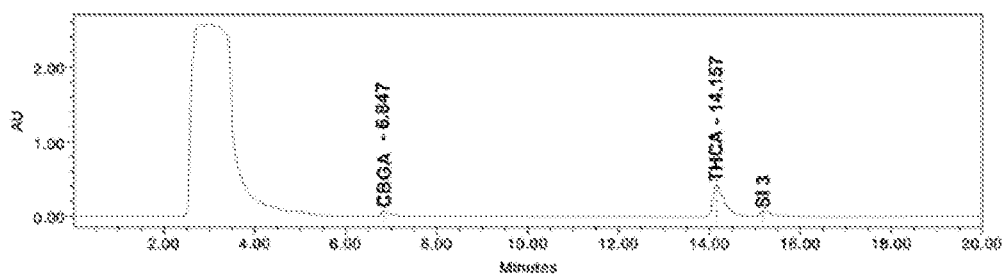
FIG. 3 illustrates the effect of 10% DMSO and 20% cyclodextrin on THCA synthase activity. 100 µl THCA synthase in crude fermentation supernatant (10× concentrated) were reacted with 50 µl 2 mg/ml CBGA in 350 µl citrate buffer at pH 4.85 containing 2 mg cyclodextrin. Peaks (from left to right): #1 CBGA (10.33%), #2 THCA (72.37%), #3 CBCA (17.3%).
Figure 4:
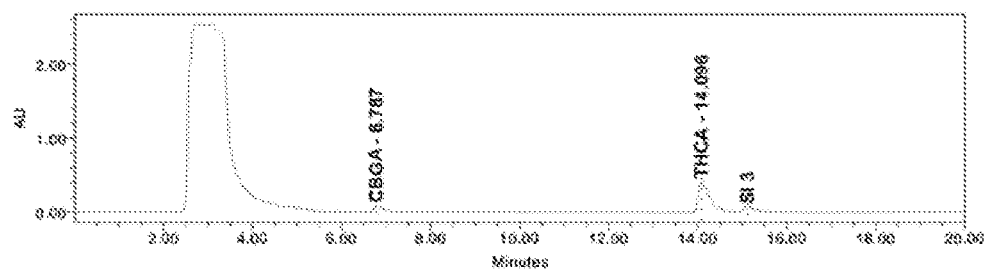
FIG. 4 illustrates the effect of 10% DMSO and 40% cyclodextrin on THCA synthase. 150 µl THCA synthase in crude fermentation supernatant (10× concentrated) were reacted with 75 µl 2 mg/ml CBGA in 525 µl citrate buffer at pH 4.85 containing 3 mg cyclodextrin. Peaks (from left to right): #1 CBGA (11.50%), #2 THCA (72.08%), #3 CBCA (16.42%).
Figure 5:
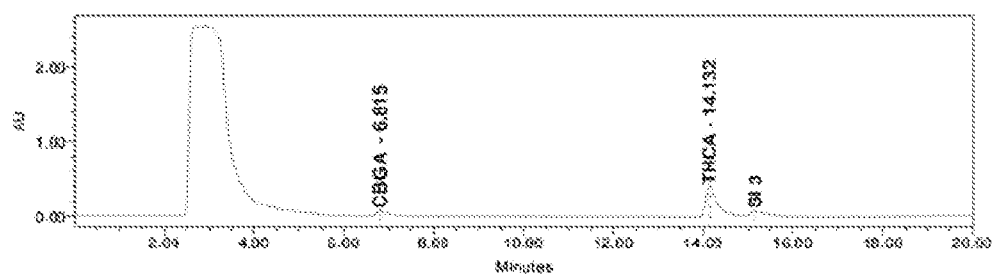
FIG. 5 illustrates the effect of 10% DMSO and 60% cyclodextrin on THCA synthase activity. 200 µl THCA synthase in crude fermentation supernatant (10× concentrated) were reacted with 100 µl 2 mg/ml CBGA in 700 µl citrate buffer at pH 4.85 containing 4 mg cyclodextrin. Peaks (from left to right): #1 CBGA (10.36%), #2 THCA (73.98%), #3 CBCA (15.65%).

The conversion rate from CBGA to THCA and CBCA was greater than 90% in two hours using crude fermentation supernatant (FIGS. 3 and 5).

Figure 6:
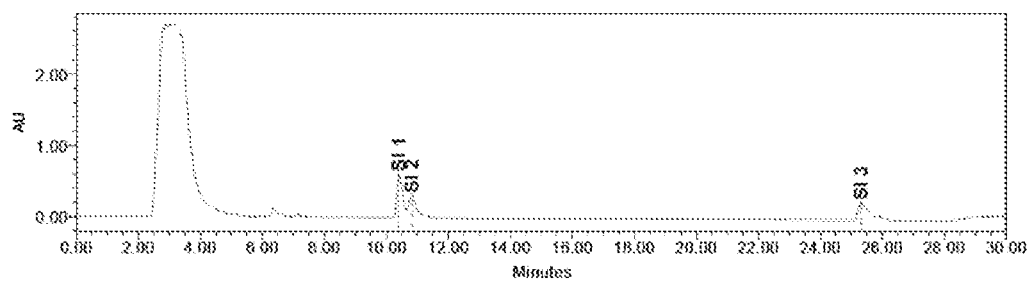
FIG. 6 illustrates the effect of 10% DMSO and 20 mg/ml cyclodextrin on CBDA synthase activity. 200 µl CBDA synthase in crude fermentation supernatant (10× concentrated) were reacted with 100 µl 4 mg/ml CBGA in 700 µl citrate buffer at pH 4.85 containing 4 mg cyclodextrin. Peaks (from left to right): #1 CBDA (40.63%), #2 CBGA (28.43%), #3 CBCA (30.95%).

The conversion rate from CBGA to CBDA and CBCA was greater than 70% overnight using crude fermentation supernantant. (FIG. 6).

7. Enzyme Purification

The cannabinoid acid synthase enzymes thus obtained were purified by size exclusion chromatography (SEC) using a 2.2 cm inner diameter column and 5 ml supernatant in a column volume to crude enzyme supernatant ratio of 20:1. Briefly, 10 g of dry sephadex beads were measured and added to a Pyrex glass container. 100 ml of 50 mM Phosphate buffer pH 7.4 were added to Bio-GEL P-100 beads with excess amount and let sit for more than 12 hours. (P-100 beads swollen 12× when completely hydrated). Using a vacuum pump, the hydrated P-100 beads and another 1 L pH 7.4 50 mM Phosphate buffer were de-gassed to cause the beads to settle in the excess buffer. The buffer was poured off, and 100 mL de-gassed Phosphate buffer were poured into the beads, such that the beads settled again. These steps were repeated two more times. The hydrated P-100 was then poured into a glass column until 2-5 cm of the gel bed was formed, then more gel was poured to the desired height and let it settle. The column thus formed was stored at 4° C. 5 mL of either THCA or CBDA synthase crude supernatant was run through the column at 4° C. and the fractions were collected at 5 mL/fraction for 25 fractions. All fractions were saved, stored at 4° C. and analyzed for enzyme activity and by SDS-PAGE gel to examine purification efficiency and resolution.

B. Cannabinoid and Cannabinoid Analog Enzymatic Production

1. Enzymatic Assay Conditions

The Standard CBDA synthase enzyme/THCA synthase enzyme reaction assay conditions were as follows: enzyme reaction was conducted in a 1.5 ml Eppendorf snap cap tube. 25 µl substrate, such as CBGA, dissolved in DMSO at 1.0 mg/ml in 200 µl of 100 mM citrate buffer pH 4.85 was incubated with 25 µl enzyme solution at 30° C. for 2 hours. The reaction was terminated by the addition of 250 µl MeOH and analyzed by HPLC.

Enzyme activity was tested under a variety of conditions as follows:

1. Different solvents and conditions were tested to enhance substrate solubility and delivery, including but not limited to DMSO, DMF, IPA, cyclodextrin (CD), SDS, Triton-X.

2. Assays were run at pH's 4, 5, 6, 7, and 8.

3. Enzyme assays were run in either Sodium phosphate buffer or Citrate buffer with or without SDS or Triton-X 4. Enzyme assays were run under a variety of ionic strengths 5. Results of incubation times between 2 hrs to 4 days were compared.

Results

Table 6 below shows that DMSO, DMF, IPA and cyclodextrin facilitated solubilization of cannabinoids. Cyclodextrin solubilized up to 20-25 g/L of CBGA for conversion. Enzymatic rate was enhanced when 20% DMSO (v/v) was added to the reaction mixture and THCA synthase produced both THCA and CBCA in the reaction (Table 7).

TABLE 6

Effects of solvents on THCA Synthase Activity

| Reaction Condition Studies | Parameters | % CBGA conversion | THCA:CBCA |
|---|---|---|---|
| 100 mM Solvents | 100 mM Cit 50 ug Enzyme in DMF | 84 | 1.066:1 |
| | 100 mM Cit 50 ug Enzyme in DMSO | 85 | 7.96:1 |
| | 100 mM Cit 50 ug Enzyme in CD | 81 | 12.34:1 |
| | 400 mM cit 50 ug Enzyme in IPA | 61 | 11.9:1 |
| | 100 mM NaP 50 ug Enzyme in 20 ul CD | 79 | 1.11:1 |
| | 100 mM NaP 50 ug Enzyme in 20 ul SDS | 72 | 1.22:1 |
| | 100 mM Cit 50 ug Enzyme + SDS in CD | 8 | 10.45:1 |

TABLE 7

Effects of DMSO Concentration on THCA Synthase Rate and Product Ratio

| DMSO | FASTER | THCA:CBCA |
|---|---|---|
| 0% | 1 X | |
| 10% | 1.2 X | 10:1 |
| 20% | 2.5 X | 5:1 |
| 25% | — | 1:1 |
| 30% | 0.3 X | |

The effect of pH on THCA Synthase activity is shown in Tables 8 and 9 below.

TABLE 8

Effects of pH on THCA Synthase Activity

| pH | THCA | CBCA |
|---|---|---|
| 4 | 1 | 0 |
| 5 | 2.33 | 1 |
| 6 | 1 | 5.67 |
| 7 | 0 | 1 |

In summary, changing the pH of the THCA synthase enzyme reaction affects the products. At pH 4 THCA is the only product. At pH 5 the ratio of THCA:CBCA is 2.33:1. At pH 6 the ratio is reversed and the product mix is THCA:CBCA 1:5.67. At pH 7 CBCA is the only product.

TABLE 9

Effects of pH and Cyclodextrin on THCA Synthase Activity

| Reaction Condition | Parameters | % CBGA conversion | THCA CBCA |
|---|---|---|---|
| pH exchange | 400 mM Cit pH 5.0, 50 µg Enzyme in CD | 59 | 14.9:1 |
| | 400 mM Cit pH 6.5, 50 µg Enzyme in CD | 42 | 1.1:1 |
| | 400 mM NaPi pH 5.0, 50 µg Enzyme in CD | 59 | 17.37:1 |
| | 400 mM NaPi pH 6.5 50 µg enzyme 20 µg in CD | 65 | 1.11:1 |

The effect of pH on CBDA synthase activity is shown in Table 10 below.

TABLE 10

Effects of pH on CBDA Synthase Activity

| pH | CBDA | CBCA |
|---|---|---|
| 4.2 | 2.5 | 1 |
| 5 | 1.13 | 1 |
| 5.2 | 1 | 1.17 |
| 5.4 | 1 | 2.45 |
| 5.8 | 1 | 6.14 |
| 6.2 | 1 | 28.13 |
| 6.8 | 0 | 0 |

In summary, changing the pH of the CBDA synthase enzyme reaction affects the products. At pH 4.2 CBDA:CBCA ratio is 2.5:1. At pH 5 the ratio of CBDA:CBCA is 1.13:1. At pH 6.8 there is no product forming from CBDA synthase enzyme reaction.

These results clearly show that it is possible to control the ratio of THCA:CBCA produced by the THCA synthase by controlling the pH of the enzymatic reaction. Enzyme assays were run in either Sodium phosphate buffer or Citrate buffer with or without SDS or Triton-X.

The effect of different concentrations of cyclodextrin on cannabinoid acid synthase activity was evaluated. The results for the CBDA synthase at pH 4.85 are shown in Table 11 below.

TABLE 10

Effect of Cyclodextrin on CBDA Synthase Reaction Conversion Rate and Product Ratio

| Cyclodextrin concentration | Conversion rate | CBDA:CBCA ratio |
|---|---|---|
| 0 mg/ml | 40% | 1.13:1 |
| 2 mg/ml | 57% | 1.24:1 |
| 4 mg/ml | N/A | N/A |
| 8 mg/ml | 61% | 1.27:1 |
| 12 mg/ml | 60% | 1.33:1 |
| 16 mg/ml | 50% | 1.04:1 |
| 20 mg/ml | 53% | 1.0:1 |
| 28 mg/ml | 45% | 1.24:1 |

These results clearly show that the concentration of cyclodextrin in the reaction mixture affects the enzymatic conversion rate of the substrate into the products as well as the ratio between the different products of the reaction.

These experiments also showed that the optimal cyclodextrin (CD):CBGA ratio in the enzyme reaction mix was 11:1 (mass:mass) or 4:1 (molar ratio) for CBDA synthase, and that the optimal cyclodextrin (CD):CBGA ratio in the enzyme reaction mix was 28:1 (mass:mass) or 7.3:1 (molar ratio) for THCA synthase CD:CBGA. The presence of cyclodextrin in the reaction mix in such concentration resulted in 98% conversion in 2 hours (data not shown).

B. Cannabinoid Extraction and Purification

Cannabinoids and cannabinoid analogs obtained from the enzymatic reactions with the cannabinoid acid synthase as described above were extracted by solvent extraction as follows:

Solvent was added to the reaction mix at a ratio of 1:3 (v/v), the mixture was vigorously vortexed at room temperature for 2 minutes and centrifuged at 3200 g for 10 minutes. The solvent fraction was separated and stored in a glass vial. These steps were repeated and all extractions were combined and analyzed by HPLC.

C. Production of Cannabinoid Acid Synthase Enzymes by Fermentation

Cannabinoid acid synthase enzymes were produced by fermentation following Invitrogen 'Pichia Fermentation Process Guidelines'. Some modifications were as follows:

A. Inoculum Flask Preparation

From a frozen glycerol stock of Pichia strain GS115 (Mut+, Arg+, His-), a YPD plate was inoculated. After 48 hours a single colony on YPD was used to inoculate 300 ml of BMGY, in a 2 L baffled flask. The culture was grown at 28° C., 270 rpm, until $OD_{600}$ reached 2-6 (approximately 15 hours).

B. Fermentor Preparation/Batch Glycerol

After sterilization and cooling of the 3.5 L of Basal Salts Medium in the Glass vessel of the BioFlo 3000 Fermentor, the temperature was set to no less than 27° C. and no more than 30° C. Aeration and Agitation were set to the PID mode (dissolved Oxygen dependent). pH was continually adjusted to 6.5 with 30% NH4OH. The Fermentor was inoculated with 300 ml of the culture generated above. 200 ml of 20% casamino acids prepared in sterile 100 mM, pH 6.5 Phosphate Buffer, were added. The dissolved oxygen was adjusted to be maintained above 20%. After the glycerol from the BMGY medium was completely consumed (approximately 24 hours), a 10 ml sample was taken at the end of this first fermentation stage and analyzed for cell growth (OD600) and wet cell weight. The pellet was frozen at −80° C. for later analysis of protein. The sampling was repeated at end of each stage.

C. Glycerol Fed-Batch Phase

50% w/v glycerol with 12 ml PTM trace salts per liter of glycerol solution was added to increase cell biomass. Feed rate was set to 18.15 ml/hr./liter initial fermentation volume. Glycerol feed was continued until wet cell weight reached 180-220 g/liter and DO spike was used to monitor the end point of glycerol fed batch phase.

D. Methanol Fed-Batch Phase

Methanol induction was initiated after all glycerol was consumed to induce the AOX1 promoter and express the cannabinoid synthases. 100% methanol with 12 ml PTM trace salts per liter of methanol was added. Feed rate was initially set at 3.6 ml/hr./liter initial fermentation volume. Agitation, aeration and oxygen feed were adjusted for the next two hours to maintain the DO above 20%. A steady DO reading inferred a full adaptation to methanol at which point methanol feed was doubled to 7.3 ml/hr./liter. After 2 hours methanol feed was further increased to 10.9 ml/hr./liter initial fermentation volume. After about 2 hours or at the first sign of foaming, 20-50 μl Sterile Pure Anti-Foam 204, Sigma were added so as to keep the headspace of the fermentor clear and prevent the foam from interfering with the agitation and various feeds. Additional 20-50 μl aliquots were added as needed approximately once a day or every other day of the entire run of fermentation. Once 10.9 ml/hr./liter was established, enzyme activity was measured and monitored every 8 hours thereafter. Fermentation was stopped 5 days after initial inoculation or upon reaching a plateau in protein concentration.

E. Harvesting Cells and Supernatant

At harvest time, the final fermentation volume was almost double the initial volume. The cell density was increased to ~400 g/liter wet cells. The 7 liter of culture was collected into 500 ml centrifuge bottles and centrifuged at 10,000 RPM for 15 min to separate cells from the supernatant. The supernatant was concentrated 10× using Tangential Flow Filtration. A sample of supernatant was loaded onto a polyacrylamide gel for protein analysis. THCA synthase was around 80 KDa. 30 Kda TFF filter was used to concentrate the fermentation supernatant 10×. A portion of the TFF concentrated supernatant was loaded onto a nickel column for purification of the enzyme. A portion of the original fermentation supernatant was fractioned by ammonium sulfate precipitation (45%-75%).

F. Standard Enzyme Activity Assay

In 200 μl of 100 mM pH 4.8 Citrate buffer; 25 μl Substrate (CBGA) dissolved in DMSO at 1 mg/mL concentration; and 25 μl enzyme (supernatant) were added in a 1.5 mL Eppendorf snap cap tube. The tube was incubated at 30° C. for 2 hours and the reaction was terminated by adding 250 μl MeOH. Activity of the enzymes was analyzed by HPLC.

E. Concentration/Purification of Cannabinoid acid synthase Enzymes from Fermentation After fermentation the cells were separated from the supernatant by centrifugation at 10,000 RPM×15 min. The enzyme was then concentrated and purified as follows: the supernatant was concentrated 10× using Tangential Flow Filtration and then fractionated using ammonium sulfate precipitation; the protein fraction salting out between 45%-75% (NH4)2SO4 contained the synthase. The TFF filtered supernatant was loaded onto a nickel column for purification of the enzyme.

F. Chemical Synthesis of Cannabinoid Substrates

A. Synthesis of Geraniol (3,7-Dimethylocta-2,6-dien-1-ol,)

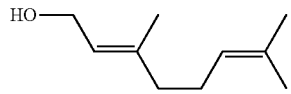

Geraniol was obtained by distillation of palmarosa oil. Palmarosa oil (New Directions Aromatics) was distilled under reduced pressure and the fractions that distil between 139-145° C. and under a reduced pressure of 25 mm Hg were pooled to obtain pure geraniol.

B. Synthesis of Olivetol

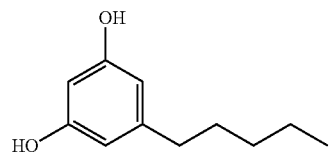

Olivetol was synthesized using a published procedure (Focella, A, et al., J Org. Chem., Vol. 42, No. 21, (1977), p. 3456-3457).

1. Methyl 6-N-Pentyl-2-hydroxy-4-oxo-cyclohex-2-ene-1-carboxylate

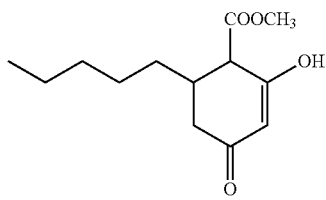 [SMILES: CCCCCC1CC(=O)C=C(O)C1C(=O)OC]

To a stirring solution of sodium methoxide (32.4 g, 0.60 mol) and dimethyl malonate (90 g, 0.68 mol) in 230 mL of anhydrous methanol was added portion wise 75 g (0.48 mol) of 90% 3-nonen-2-one. The reaction mixture was then refluxed for 3 h under $N_2$ and allowed to cool to room temperature. The solvent was distilled under reduced pressure and the residue dissolved in 350 mL of water. The slurry of white crystals and the almost clear solution was extracted thrice with 80 mL of chloroform. The aqueous layer was acidified to pH 4 with concentrated HCl and the white precipitate that formed was allowed to stand overnight prior to filtration. The crystals were dried at 50° C. under high vacuum for 5 hours to yield 106.5 g (0.4416 mol) (92%) of methyl 6-n-Pentyl-2-hydroxy-4-oxo-cyclohex-2-ene-1-carboxylate (mp 96-98 C). The product was recrystallized using a mixture of petroleum ether:ethyl acetate (9:1), and gave 94 g of pure methyl 6-n-Pentyl-2-hydroxy-4-oxo-cyclohex-2-ene-1-carboxylate (melting point of 98-100 C).

2. 1-N-Pentyl-3, 5-dihydroxybenzene (Olivetol)

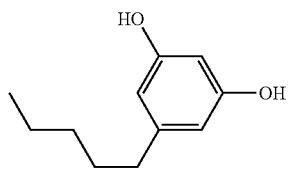

To a stirring ice-cooled solution of methyl 6-N-pentyl-2-hydroxy-4-oxo-cyclohex-2-ene-1-carboxylate (58.4 g, 0.24 mol) dissolved in 115 mL dimethylformamide was added dropwise 37.9 g (0.23 mol) of bromine dissolved in 60 mL of dimethylformamide. At the end of the addition (ca. 90 min) the reaction mixture was slowly heated to 80° C. during which time the evolution of carbon dioxide became quite vigorous.

The reaction was maintained at this temperature until gas evolution had ceased following which the reaction was further heated to 160° C. and held at this temperature for approximately 10 hours. After heating, the reaction was allowed to cool and the solvent DMF was removed under reduced pressure. The residue thus obtained was treated with water (80 mL) and extracted twice with 250 mL of ether. The combined ether layers were washed with water, then washed with 2×80 mL of a 10% solution of sodium bisulfite, 2×80 mL of a 10% solution of acetic acid, and then again with water.

After drying over anhydrous sodium sulfate the solvent was removed under reduced pressure to give 46.8 g of a viscous oil. The oil was distilled under reduced pressure to give 30.3 g (0.168 mol) (69.3%) of olivetol as product. HPLC analysis indicated 97.5% purity.

C. Synthesis of CBG

CBG was synthesized following the protocol disclosed by Taura et al., (1996), *The Journal of Biological Chemistry*, Vol. 271, No. 21, p. 17411-17416.

1. Synthesis of 2-[(2E)-3, 7-dimethylocta-2, 6-dienyl]-5-pentyl-benzene-1,3-diol (Cannabigerol (CBG))

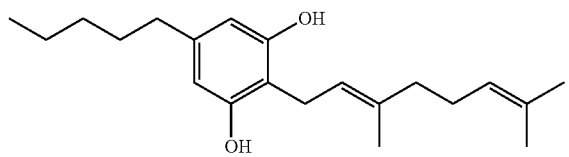 [SMILES: CCCCCc1cc(O)c(C/C=C(\C)CCC=C(C)C)c(O)c1]

Geraniol (3 g, 0.0194 mol) and olivetol (2 g, 0.0111 mol) were dissolved in 400 mL of chloroform containing 80 mg of p-toluenesulfonic acid as catalyst and the reaction mixture was stirred at room temperature for 12 h in the dark. After 12 hours, the reaction mixture was washed with saturated sodium bicarbonate (400 mL) and then with $H_2O$ (400 mL). The chloroform layer was concentrated at 40 C under reduced pressure, and the residue obtained was chromatographed on a 2.0 cm×25 cm silica gel column using benzene (1000 mL) as the eluent to give 1.4 g (0.00442 mol)(39.9%) CBG as product.

Alternatively crude CBG was purified as follows. To a 250 mL beaker was added 7.25 g crude CBG and 50 mL benzene. The flask was swirled to dissolve the CBG and 50 g silica gel was added, along with a stir bar. The solution was stirred overnight, and then poured into a 44 cm×2.75 cm column. The column was eluted with 300 mL benzene. The eluent, approximately 70 mL fractions were assayed for CBG. Fractions 1, 2, and 3 (~230 mL) that contained CBG were combined and the solvent removed under pressure to give 6.464 g residue containing >80% CBG, having a purity suitable for use in the next synthetic step.

In one embodiment, crude CBG was purified by mixing 7.25 g crude CBG residue with a slurry of silica gel (50 mL), in a 250 ml Beaker. This mixture was slowly agitated for 1 hour and then vacuum filtered using a fine mesh filter paper. The filter cake was washed with 250 ml benzene until a clear filtrate was obtained. The solvent from the filtrate was removed under reduced pressure to give 6.567 g of a residue having >80% CBG.

A. Synthesis of Methylmagnesium Carbonate (MMC)

Methylmagnesium Carbonate (MMC) was synthesized following the protocol disclosed by Balasubrahmanyam et al., (1973), *Organic Synthesis, Collective Volume V*, John Wiley & Sons, Inc., p. 439-444.

A dry 2 liter, three necked flask was fitted with a mechanical stirrer, a condenser, and a 1 liter, pressure-equalizing addition funnel, the top of which was fitted with a gas inlet tube. A clean, dry magnesium ribbon (40.0 g, 1.65 mol) was placed in the flask and the system was flushed with nitrogen prior to the addition of anhydrous methanol (600 mL). The evolution of hydrogen gas was controlled by cooling the reaction mixture externally. When hydrogen evolution had ceased, a slow stream of nitrogen was passed through the system and the condenser was replaced by a total condensation-partial take-off distillation head. The nitrogen flow was stopped and the bulk of the methanol distilled from the solution under reduced pressure. Distillation was stopped when stirring of the pasty suspension of magnesium methoxide was no longer practical. The system was again flushed using nitrogen and the outlet from the distillation head was attached to a small trap containing mineral oil so that the volume of gas escaping from the reaction system could be estimated.

Anhydrous dimethylformamide (DMF)(700 mL) was added to the reaction flask, and the resulting suspension was stirred vigorously while a stream of anhydrous carbon dioxide was passed into the reaction vessel through the gas inlet tube attached to the addition funnel. The dissolution of carbon dioxide was accompanied by an exothermic reaction with the suspended magnesium methoxide. When no more $CO_2$ is absorbed, the colorless solution was heated under a slow stream of $CO_2$ gas until the temperature of the liquid distilling reached 140° C., indicating that residual methanol had been removed from the reaction mixture. The reaction mixture was flushed using a slow stream of nitrogen to aid in cooling the mixture to room temperature under an inert atmosphere. This yielded a solution having 536 mg MMC/mL of DMF.[8]

B. Synthesis of CBGA 6-carboxylic acid-2-[(2E)-3,7-dimethylocta-2,6-dienyl]-5-pentyl-benzene-1,3-diol, Cannabigerolic Acid (CBGA) was prepared as follows. To a 10 mL conical flask was added 1 mL of a DMF solution of MMC. To this solution was added 2-[(2E)-3,7-dimethylocta-2,6-dienyl]-5-pentyl-benzene-1,3-diol (120 mg, 0.379 mmol). The flask was heated at 120° C. for 1 hour, following which the reaction mixture was dissolved in 100 mL of chloroform:methanol (2:1) solution. The pH of this solution was adjusted with dilute HCl to pH 2.0, and then partitioned using 50 mL $H_2O$.

The organic layer was dried over sodium sulfate and the solvent was removed by evaporation. HPLC analysis of the crude reaction showed ~40% conversion of CBG to CBGA.

Alternatively, 3.16 g (10 mmols) of CBG (or any other neutral cannabinoid), 8.63 g (100 mmols) magnesium methylate and 44 g (1 mol) of dry ice were sealed in a pressure compatible vessel. The vessel is heated to 50° C., and the temperature held at this value for three hours. Following heating, the vessel is cooled to room temperature and slowly vented. The reaction mixture was dissolved in 100 mL of a chloroform:methanol (2:1) solvent. The pH of this solution was adjusted with dilute HCl to pH 2.0 and this solution was then partitioned using 50 mL of $H_2O$. The organic layer was dried over sodium sulfate and the solvent was removed by evaporation. HPLC analysis of crude reaction mixture showed ~85% conversion of CBG to CBGA using this protocol.

Crude CBGA was purified by chromatography using a 2.0 cm×25 cm silica gel column. The product was eluted using a mixture of n-hexane:ethyl acetate (2:1) (1000 mL), to obtain 45 mg (0.125 mmol)(37.5%) of the desired product.

Alternatively, ultra high purity CBGA was obtained by chromatographing the crude using LH-20 lipophilic resin as the medium. 400 g of LH-20 Sephadex resin was first swollen using 2 L of DCM:chloroform (4:1) solvent. The swollen resin was gravity packed in a 44×2.75 cm column. The column was loaded with 2.1 g of crude CBGA dissolved in a minimum amount of DCM:chloroform (4:1) solvent and eluted with 1.7 L of the same solvent. 100 mL fractions were collected. The unreacted CBG was eluted as a yellow/orange solution using this solvent system. After the passage of about 1.7 L of this solvent, no more yellow/orange fraction were observed and the eluting solvent was changed to 100% acetone to elute the bound CBGA.

The fractions containing CBGA were pooled and the solvent was removed to obtain 0.52 g CBGA (~90% recovery). Increasing the volume of DCM:chloroform (4:1) solvent passed through the column prior to eluting with acetone, yielded CBGA having purity greater than 99.5%.

C. Synthesis of CBGV

CBGV was synthesized as follows.

A. Methyl 6-N-Propyl-2-hydroxy-4-oxo-cyclohex-2-ene-1-carboxylate

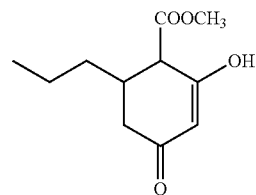

Briefly, 3-hepten-2-one (30.1 g, 0.25 mol) was added dropwise to a dry methanolic (125 mL dry MeOH), solution of diethyl malonate (52.016 g, 0.323 mol) and sodium methoxide (16.206 g, 0.3 mol). The crude product weighed 46.315 g upon drying at 45° C. overnight in a vacuum oven. The crude product was dissolved in petroleum ether (300 mL). After stirring, any undissolved material was filtered from the solution prior to the addition of ethyl acetate (30 mL), to precipitate CBGV. The precipitate was filtered and dried overnight at 44° C. in a vacuum oven. A total of 33.569 g (0.157 mol) (52.3%) of the desired product was recovered.

B. 1-N-Propyl-3, 5-dihydroxybenzene

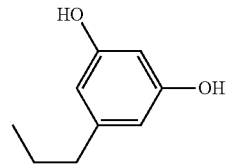

A procedure similar to the one described above for the synthesis of olivetol was used to manufacture the titled compound, except that methyl 6-N-propyl-2-hydroxy-4-oxo-cyclohex-2-ene-1-carboxylate was used as the starting material. Briefly, to a stirring ice cold DMF solution of methyl 6-N-propyl-2-hydroxy-4-oxo-cyclohex-2-ene-1-carboxylate was added a DMF solution of bromine. Following the addition of bromine the reaction mixture was heated to 80° C. Heating was accompanied by the generation and release of carbon dioxide gas. After gas evolution has ceased, the temperature of the reaction was increased to 160° C. and heating was continued for 10 hours. The reaction was then cooled and DMF was removed under reduced pressure. The crude mixture was diluted with water and subjected to solvent extraction using diethyl ether. The titled compound was obtained by removing the ether and distilling the oil that remains.

C. 2-[(2E)-3,7-dimethylocta-2,6-dienyl]-5-propyl-benzene-1,3-diol, (CBGV)

The synthesis of CBGV proceeded by adding p-toluene-sulfonic acid to a chloroform solution of geraniol and 1-N-Propyl-3,5-dihydroxybenzene. After stirring the reaction at room temperature in the dark for 12 hours, water was added to partition the crude product into the chloroform layer. The chloroform layer was then washed with saturated sodium bicarbonate, dried and the organic solvent removed prior to purification as described above for the synthesis of CBG.

D. 6-carboxylic acid-2-[(2E)-3,7-dimethylocta-2,6-dienyl]-5-propyl-benzene-1,3-diol (CBGVA)

6-carboxylic acid-2-[(2E)-3,7-dimethylocta-2,6-dienyl]-5-propyl-benzene-1,3-diol, cannabigerolic Acid (CBGVA) was prepared as follows. Methyl magnesium carbonate (MMC) was prepared as described above. To a DMF solution of MMC in a flask was added 2-[(2E)-3,7-dimethylocta-2,6-dienyl]-5-propyl-benzene-1,3-diol. The flask was heated at 120° C. for 1 hour, following which the reaction mixture was dissolved in a 2:1 mixture of chloroform:methanol. The pH of this solution was adjusted with dilute HCl to pH 2.0, and the reaction mixture was extracted using $H_2O$. The organic layer was dried over sodium sulfate and the solvent was removed by evaporation.

G. Large Scale Enzymatic Production of Cannabinoids 100 ml of a 10 mM sodium phosphate buffer (pH 5.0) were placed in a glass reaction vessel equipped with oxygen gas sparger and a stirrer. To this solution 35 g/l of either 2-hydroxypropyl-3-cyclodextrin (HPβCD; Kleptose® HPB), a sulfobutylether β-cyclodextrin sodium salt (SBEPβCD; Captisol®), or a randomly methylated β-cyclodextrin (RMβCD) were added. The CD was added in small 5 g portions to ensure full dissolution.

2.5 g of a cannabinoid acid synthase substrate, for example, CBGA or CBGV-A or a Formula I, II or V compound, were added to the buffered cyclodextrin solution. The molar ratio of CD to substrate was about 4:1. 60 mg of purified synthase were added to the solution and the reaction mixture was incubated at 30° C. for 8 hours. Progress of the reaction was periodically monitored by HPLC, and using an enzymatic assay to detect and quantify the evolution of hydrogen peroxide.

After 8 hours, greater than 90% of a CBGA substrate was converted to THCA and CBCA. The ratio of THCA to CBCA was approximately 10:1 at an acidic pH of 5.0. The ratio of the CBC isomers was 5:1.

The aqueous solution was diluted 10:1 with 95% EtOH. This causes cyclodextrin to precipitate out leaving the cannabinoids in solution. The cyclodextrin was vacuum filtered, washed with 1 L of 90% EtOH, and dried to permit its reuse in a future reaction. Concentration of the ethanolic solution containing the cannabinoids followed suspension of the residue in DCM:chlorofrom (4:1) solvent yields ~25 g crude orange-yellow residue.

H. Large Scale Purification of Cannabinoids

Purification of cannabinoids synthesized using a method of this technology was accomplished chromatographically using LH-20 lipophilic resin. Briefly, 4000 g of the resin was swollen using 20 L of DCM:chloroform (4:1). The swollen resin was gravity packed in a 44×27.5 cm column. The volume of the swollen resin is ~1350 mL. The column was loaded with 25 g crude residue dissolved in a minimum amount of the solvent and then washed with 4 L DCM:chloroform (4:1) solvent to elute CBG. No cannabinoid acids were eluted from the column during this elution.

Gradient elution with a 1:1 to 0:1 DCM:acetone solvent was used to elute the cannabinoid acids. Each step of the gradient used one column volume (4 L) of solvent. CBCA eluted first, followed by CBGA, and then THCA. The purity of each cannabinoid was >99.5%.

The pure cannabinoids can further be processed to their neutral or "active" form by heating the acid forms at 90° C. under vacuum. Decarboxylation was quantitative to give the neutral cannabinoid. If necessary, recrystallization can be performed to obtain pharmaceutical grade cannabinoids.

Those of skill in the art will recognize that numerous modifications and changes may be made to the exemplary designs and embodiments described herein and that the invention is not limited to such embodiments.

What is claimed is:

1. A system for producing cannabinoids wherein the system comprises:
   (i) a bioreactor comprising cells stably transformed with one or more cannabinoid genes;
   (ii) a reaction mixture comprising a compound according to Formula I:

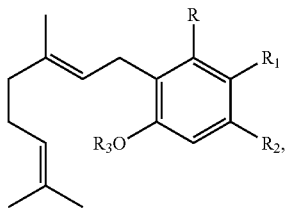

Formula I wherein
   R is selected from —OH, halogen, —SH, or a —NR$_a$R$_b$ group;
   R$_1$ and R$_2$ are each independently selected from the group consisting of —H, —C(O)R$_a$, —OR$_a$, an optionally substituted C$_1$-C$_{10}$ linear or branched alkylene, an optionally substituted C$_2$-C$_{10}$ linear or branched alkenylene, an optionally substituted C$_2$-C$_{10}$ linear or branched alkynylene, an optionally substituted C$_3$-C$_{10}$ aryl, an optionally substituted C$_3$-C$_{10}$ cycloalkyl, (C$_3$-C$_{10}$)aryl-(C$_1$-C$_{10}$)alkylene, (C$_3$-C$_{10}$)aryl-(C$_2$-C$_{10}$)alkenylene, and (C$_3$-C$_{10}$)aryl-(C$_1$-C$_{10}$)alkynylene, or R$_1$ and R$_2$ together with the carbon atoms to which they are bonded form a C$_5$-C$_{10}$ cyclic ring;
   R$_3$ is selected from the group consisting of H, —C(O)R$_a$ and C$_1$-C$_{10}$ linear or branched alkyl; and
   R$_a$ and R$_b$ are each independently —H, —OH, —SH, —NH$_2$, (C$_1$-C$_{10}$) linear or branched alkyl, or a C$_3$-C$_{10}$ cycloalkyl; and (iii) a controller configured to modify one or more reaction conditions to modulate the ratio of the cannabinoid products, wherein the condition to be modified is pH or solvent.

2. The system of claim 1, wherein the cells are selected from the group consisting of fungal, animal, algal, and bacterial.

3. The system of claim 2, wherein the fungal cells are yeast cells.

4. The system of claim 1, wherein the cannabinoid biosynthetic gene is the tetrahydrocannabinolic acid (THCA) synthase gene.

5. The system of claim 1, wherein the cannabinoid biosynthetic gene is the cannabidiolic acid (CBDA) synthase gene.

6. The system of claim 1, wherein cannabigerolic acid (CBGA) is a reagent in the reaction mixture.

7. The system of claim 1, wherein R is —OH and R$_1$ is —H or —COOH.

8. The system of claim 1, wherein R$_2$ is a C$_1$-C$_{10}$ linear or branched alkyl wherein said C$_1$-C$_{10}$ linear or branched alkyl is selected from the group consisting of CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, iso-propyl, sec-butyl, iso-butyl, neopentyl, 2-methyl hexyl, and 2,3-dimethyl hexyl.

9. The system of claim 1, wherein R$_2$ is selected from the group consisting of CH$_3$, C$_2$H$_5$, C$_3$H$_7$, C$_4$H$_9$, C$_6$H$_{13}$, C$_7$H$_{15}$ and C$_8$H$_{17}$.

10. The system of claim 1, wherein R$_2$ is C$_3$H$_7$.

11. The system of claim 1, wherein R$_2$ is C$_5$H$_{10}$.

12. The system of claim 1, wherein;
    R is —OH
    R$_1$ is —H or —COOH;
    R$_2$ is a C$_1$-C$_{10}$ linear or branched alkyl wherein said C$_1$-C$_{10}$ linear or branched alkyl is selected from the group consisting of CH$_3$, C$_2$H$_5$, C$_3$H$_7$, C$_4$H$_9$, C$_6$H$_{13}$, C$_7$H$_{15}$, C$_8$H$_{17}$, iso-propyl, sec-butyl, iso-butyl, neopentyl, 2-methyl hexyl, and 2,3-dimethyl hexyl;
    R$_3$ is H.

* * * * *

SEQUENCE LISTING

```
<160> NUMBER OF SEQ ID NOS: 9

<210> SEQ ID NO 1
<211> LENGTH: 1638
<212> TYPE: DNA
<213> ORGANISM: Cannabis sativa

<400> SEQUENCE: 1
atgaattgct cagcattttc cttttggttt gtttgcaaaa taatattttt ctttctctca      60
ttccatatcc aaatttcaat agctaatcct cgagaaaact tccttaaatg cttctcaaaa     120
catattccca acaatgtagc aaatccaaaa ctcgtataca ctcaacacga ccaattgtat     180
atgtctatcc tgaattcgac aatacaaaat cttagattca tctctgatac aaccccaaaa     240
ccactcgtta ttgtcactcc ttcaaataac tcccatatcc aagcaactat tttatgctct     300
aagaaagttg gcttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga agtttattat     480
tggatcaatg agaagaatga gaatcttagt tttcctggtg ggtattgccc tactgttggc     540
gtaggtggac actttagtgg aggaggctat ggagcattga tgcgaaatta tggccttgcg     600
```

```
gctgataata tcattgatgc acacttagtc aatgttgatg gaaaagttct agatcgaaaa    660
tccatgggag aagatctgtt ttgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcgtg agttgggtat taaaaaaact   1020
gattgcaaag aattgagctg gattgataca accatcttct acagtggtgt tgtaaattac   1080
aacactgcta atttaaaaa ggaaattttg cttgatagat cagctgggaa gaagacggct   1140
ttctcaatta agttagacta tgttaagaaa ccaattccag aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacgact ccttatgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta agttgatcc caataatttt tttagaaacg aacaaagtat cccacctctt   1620
ccaccgcatc atcattaa                                                  1638
```

<210> SEQ ID NO 2
<211> LENGTH: 545
<212> TYPE: PRT
<213> ORGANISM: Cannabis sativa

<400> SEQUENCE: 2

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190
```

Leu Met Arg Asn Tyr Gly Leu Ala Ala Asp Asn Ile Asp Ala His
    195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
                260                 265                 270

Phe Asn Lys Trp Gln Asn Ile Ala Tyr Lys Tyr Asp Lys Asp Leu Val
            275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Arg Glu Leu Gly
                325                 330                 335

Ile Lys Lys Thr Asp Cys Lys Glu Leu Ser Trp Ile Asp Thr Thr Ile
                340                 345                 350

Phe Tyr Ser Gly Val Val Asn Tyr Asn Thr Ala Asn Phe Lys Lys Glu
            355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415

Tyr Pro Tyr Gly Gly Ile Met Glu Glu Ile Ser Glu Ser Ala Ile Pro
                420                 425                 430

Phe Pro His Arg Ala Gly Ile Met Tyr Glu Leu Trp Tyr Thr Ala Ser
            435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
                500                 505                 510

Lys Asn Phe Asn Arg Leu Val Lys Val Lys Thr Lys Val Asp Pro Asn
            515                 520                 525

Asn Phe Phe Arg Asn Glu Gln Ser Ile Pro Pro Leu Pro Pro His His
    530                 535                 540

His
545

<210> SEQ ID NO 3
<211> LENGTH: 1830
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgagattcc catccatctt cactgctgtt tgttcgctg cttcttccgc tttggctgct      60
ccagttaaca ctactactga ggacgagact gctcagattc cagctgaagc tgttattggt    120
tactccgact tggaaggtga cttcgacgtt gctgttttgc cattctccaa ctccactaac    180
aacggtttgt tgttcatcaa cactacaatc gcttccattg ctgctaaaga gagggagtt    240
tccttggaga agagagaggc tgaagctaac ccaagagaaa acttcttgaa gtgttttcc     300
aagcacatcc aaacaacgt tgctaaccct aagttggttt acactcagca cgaccagttg    360
tacatgtcct tgttgaactc cacaatccag aacttgagat tcatctccga cactactcca    420
aagccattgg ttatcgttac tccatccaac aactcccaca tccaggctac tatcttgtgt    480
tccaagaagg ttggattgca gatcagaaca agatccggtg gtcatgacgc tgaaggtatg    540
tcctacattt cccaggttcc attcgttgtt gttgacttga aaacatgca ctccatcaag    600
atcgacgttc actcccaaac tgcttgggtt gaagctggtg ctactttggg tgaagtttac    660
tactggatca acgagaagaa cgagaacttg tccttcccag gtggttactg tccaactgtt    720
ggtgttggtg tcacttttc tggtggtggt tacggtgctt tgatgagaaa ctacggattg    780
gctgctgaca acatcatcga cgctcacttg gttaacgttg acggtaaggt tttggacaga    840
aagtccatgg gtgaggactt gttctgggct attagaggtg gtggtggtga aacttcggt     900
attattgctg cttggaagat caagttggtt gctgttccat ccaagtccac tatcttctcc    960
gttaagaaaa acatggaaat ccacggtttg gttaagttgt taacaagtg gcagaacatt    1020
gcttacaagt acgacaagga cttggttttg atgactcact tcatcactaa gaacatcact    1080
gacaaccacg gtaagaacaa gactactgtt cacggttact ctcttccat cttccacggt     1140
ggtgttgatt ccttggttga tttgatgaac aagtctttcc cagagttggg tatcaagaaa    1200
actgactgta aagagttctc ctggatcgac acaacaatct tctactccgg tgttgttaac    1260
ttcaacactg ctaactttaa gaaagagatc ttgttggaca gatccgctgg taaaaagact    1320
gctttctcca ttaagttgga ctacgttaag aagccaatcc agagactgc tatggttaag    1380
attttggaga gttgtacga gaggacgtt ggtgctggta tgtacgtttt gtacccatac    1440
ggtggtatca tggaagaaat ctccgagtcc gctattccat tcccacacag agctggtatt    1500
atgtacgagt tgtggtacac tgcttcttgg gagaagcaag aggacaacga aaagcacatc    1560
aactgggtta gatccgttta caacttcact actccttacg tttcccagaa cccaagattg    1620
gcttacttga actacagaga cttggacttg gtaagacta accacgcttc cccaaacaat    1680
tacacacagg ctagaatctg gggtgaaaag tacttcggaa agaactttaa cagattggtt    1740
aaggttaaga ctaaggttga ccctaacaac ttcttcagaa acgagcagtc catcccacca    1800
ttgccaccac atcatcatca ccatcactaa                                    1830
```

<210> SEQ ID NO 4
<211> LENGTH: 609
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Asn Pro Arg Glu Asn Phe Leu
                85                  90                  95

Lys Cys Phe Ser Lys His Ile Pro Asn Asn Val Ala Asn Pro Lys Leu
            100                 105                 110

Val Tyr Thr Gln His Asp Gln Leu Tyr Met Ser Leu Leu Asn Ser Thr
        115                 120                 125

Ile Gln Asn Leu Arg Phe Ile Ser Asp Thr Thr Pro Lys Pro Leu Val
    130                 135                 140

Ile Val Thr Pro Ser Asn Asn Ser His Ile Gln Ala Thr Ile Leu Cys
145                 150                 155                 160

Ser Lys Lys Val Gly Leu Gln Ile Arg Thr Arg Ser Gly Gly His Asp
                165                 170                 175

Ala Glu Gly Met Ser Tyr Ile Ser Gln Val Pro Phe Val Val Val Asp
            180                 185                 190

Leu Arg Asn Met His Ser Ile Lys Ile Asp Val His Ser Gln Thr Ala
        195                 200                 205

Trp Val Glu Ala Gly Ala Thr Leu Gly Glu Val Tyr Tyr Trp Ile Asn
210                 215                 220

Glu Lys Asn Glu Asn Leu Ser Phe Pro Gly Gly Tyr Cys Pro Thr Val
225                 230                 235                 240

Gly Val Gly Gly His Phe Ser Gly Gly Gly Tyr Gly Ala Leu Met Arg
                245                 250                 255

Asn Tyr Gly Leu Ala Ala Asp Asn Ile Ile Asp Ala His Leu Val Asn
            260                 265                 270

Val Asp Gly Lys Val Leu Asp Arg Lys Ser Met Gly Glu Asp Leu Phe
        275                 280                 285

Trp Ala Ile Arg Gly Gly Gly Gly Glu Asn Phe Gly Ile Ile Ala Ala
    290                 295                 300

Trp Lys Ile Lys Leu Val Ala Val Pro Ser Lys Ser Thr Ile Phe Ser
305                 310                 315                 320

Val Lys Lys Asn Met Glu Ile His Gly Leu Val Lys Leu Phe Asn Lys
                325                 330                 335

Trp Gln Asn Ile Ala Tyr Lys Tyr Asp Lys Asp Leu Val Leu Met Thr
            340                 345                 350

His Phe Ile Thr Lys Asn Ile Thr Asp Asn His Gly Lys Asn Lys Thr
        355                 360                 365

Thr Val His Gly Tyr Phe Ser Ser Ile Phe His Gly Gly Val Asp Ser
    370                 375                 380

Leu Val Asp Leu Met Asn Lys Ser Phe Pro Glu Leu Gly Ile Lys Lys
385                 390                 395                 400

Thr Asp Cys Lys Glu Phe Ser Trp Ile Asp Thr Thr Ile Phe Tyr Ser
                405                 410                 415
```

-continued

```
Gly Val Val Asn Phe Asn Thr Ala Asn Phe Lys Lys Glu Ile Leu Leu
                420                 425                 430

Asp Arg Ser Ala Gly Lys Lys Thr Ala Phe Ser Ile Lys Leu Asp Tyr
            435                 440                 445

Val Lys Lys Pro Ile Pro Glu Thr Ala Met Val Lys Ile Leu Glu Lys
450                 455                 460

Leu Tyr Glu Glu Asp Val Gly Ala Gly Met Tyr Val Leu Tyr Pro Tyr
465                 470                 475                 480

Gly Gly Ile Met Glu Glu Ile Ser Glu Ser Ala Ile Pro Phe Pro His
                485                 490                 495

Arg Ala Gly Ile Met Tyr Glu Leu Trp Tyr Thr Ala Ser Trp Glu Lys
                500                 505                 510

Gln Glu Asp Asn Glu Lys His Ile Asn Trp Val Arg Ser Val Tyr Asn
            515                 520                 525

Phe Thr Thr Pro Tyr Val Ser Gln Asn Pro Arg Leu Ala Tyr Leu Asn
530                 535                 540

Tyr Arg Asp Leu Asp Leu Gly Lys Thr Asn His Ala Ser Pro Asn Asn
545                 550                 555                 560

Tyr Thr Gln Ala Arg Ile Trp Gly Glu Lys Tyr Phe Gly Lys Asn Phe
                565                 570                 575

Asn Arg Leu Val Lys Val Lys Thr Lys Val Asp Pro Asn Asn Phe Phe
            580                 585                 590

Arg Asn Glu Gln Ser Ile Pro Pro Leu Pro Pro His His His His His
        595                 600                 605

His
```

<210> SEQ ID NO 5
<211> LENGTH: 1635
<212> TYPE: DNA
<213> ORGANISM: Cannabis sativa

<400> SEQUENCE: 5

```
atgaagtgct caacattctc cttttggttt gtttgcaaga taatattttt cttttctca       60
ttcaatatcc aaacttccat tgctaatcct cgagaaaact tccttaaatg cttctcgcaa     120
tatattccca ataatgcaac aaatctaaaa ctcgtataca ctcaaaacaa cccattgtat     180
atgtctgtcc taaattcgac aatacacaat cttagattca cctctgacac aaccccaaaa     240
ccacttgtta tcgtcactcc ttcacatgtc tctcatatcc aaggcactat tctatgctcc     300
aagaaagttg gcttgcagat tcgaactcga agtggtggtc atgattctga gggcatgtcc     360
tacatatctc aagtcccatt tgttatagta gacttgagaa acatgcgttc aatcaaaata     420
gatgttcata gccaaactgc atgggttgaa gccggagcta cccttggaga agtttattat     480
tgggttaatg agaaaaatga gaatcttagt ttggcggctg gtattgccc tactgtttgc     540
gcaggtggac actttggtgg aggaggctat ggaccattga tgagaaacta tggcctcgcg     600
gctgataata tcattgatgc acacttagtc aacgttcatg aaaagtgct agatcgaaaa      660
tctatggggg aagatctctt tgggcttta cgtggtggtg gagcagaaag cttcggaatc      720
attgtagcat ggaaaattag actggttgct gtcccaaagt ctactatgtt tagtgttaaa     780
aagatcatgg agatacatga gcttgtcaag ttagttaaca atggcaaaa tattgcttac      840
aagtatgaca agatttatt actcatgact cacttcataa ctaggaacat tacagataat      900
caagggaaga ataagacagc aatacacact tacttctctt cagttttcct tggtggagtg     960
gatagtctag tcgacttgat gaacaagagt tttcctgagt tgggtattaa aaaaacggat    1020
```

```
tgcagacaat tgagctggat tgatactatc atcttctata gtggtgttgt aaattacgac   1080
actgataatt ttaacaagga aatttttgctt gatagatccg ctgggcagaa cggtgctttc   1140
aagattaagt tagactacgt taagaaacca attccagaat ctgtatttgt ccaaattttg   1200
gaaaaattat atgaagaaga tataggagct gggatgtatg cgttgtaccc ttacggtggt   1260
ataatggatg agatttcaga atcagcaatt ccattccctc atcgagctgg aatcttgtat   1320
gagttatggt acatatgtag ttgggagaag caagaagata cgaaaagca tctaaactgg   1380 attagaaata tttataactt catgactcct tatgtgtcca aaaatccaag attggcatat   1440
ctcaattata gagaccttga tataggaata aatgatccca gaatcccaaa taattacaca   1500
caagcacgta tttggggtga aagtatttt ggtaaaaatt ttgacaggct agtaaaagtg   1560
aaaaccctgg ttgatcccaa taactttttt agaaacgaac aaagcatccc acctcttcca   1620
cggcatcgtc attaa                                                    1635
```

<210> SEQ ID NO 6
<211> LENGTH: 544
<212> TYPE: PRT
<213> ORGANISM: Cannabis sativa

<400> SEQUENCE: 6

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255
```

```
Phe Ser Val Lys Lys Ile Met Glu Ile His Glu Leu Val Lys Leu Val
            260                 265                 270
Asn Lys Trp Gln Asn Ile Ala Tyr Lys Tyr Asp Lys Asp Leu Leu Leu
        275                 280                 285
Met Thr His Phe Ile Thr Arg Asn Ile Thr Asp Asn Gln Gly Lys Asn
    290                 295                 300
Lys Thr Ala Ile His Thr Tyr Phe Ser Ser Val Phe Leu Gly Gly Val
305                 310                 315                 320
Asp Ser Leu Val Asp Leu Met Asn Lys Ser Phe Pro Glu Leu Gly Ile
                325                 330                 335
Lys Lys Thr Asp Cys Arg Gln Leu Ser Trp Ile Asp Thr Ile Ile Phe
            340                 345                 350
Tyr Ser Gly Val Val Asn Tyr Asp Thr Asp Asn Phe Asn Lys Glu Ile
        355                 360                 365
Leu Leu Asp Arg Ser Ala Gly Gln Asn Gly Ala Phe Lys Ile Lys Leu
    370                 375                 380
Asp Tyr Val Lys Lys Pro Ile Pro Glu Ser Val Phe Val Gln Ile Leu
385                 390                 395                 400
Glu Lys Leu Tyr Glu Glu Asp Ile Gly Ala Gly Met Tyr Ala Leu Tyr
                405                 410                 415
Pro Tyr Gly Gly Ile Met Asp Glu Ile Ser Glu Ser Ala Ile Pro Phe
            420                 425                 430
Pro His Arg Ala Gly Ile Leu Tyr Glu Leu Trp Tyr Ile Cys Ser Trp
        435                 440                 445
Glu Lys Gln Glu Asp Asn Glu Lys His Leu Asn Trp Ile Arg Asn Ile
    450                 455                 460
Tyr Asn Phe Met Thr Pro Tyr Val Ser Lys Asn Pro Arg Leu Ala Tyr
465                 470                 475                 480
Leu Asn Tyr Arg Asp Leu Asp Ile Gly Ile Asn Asp Pro Lys Asn Pro
                485                 490                 495
Asn Asn Tyr Thr Gln Ala Arg Ile Trp Gly Lys Tyr Phe Gly Lys
            500                 505                 510
Asn Phe Asp Arg Leu Val Lys Val Lys Thr Leu Val Asp Pro Asn Asn
        515                 520                 525
Phe Phe Arg Asn Glu Gln Ser Ile Pro Pro Leu Pro Arg His Arg His
    530                 535                 540

<210> SEQ ID NO 7
<211> LENGTH: 1833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgagattcc catccatctt cactgctgtt tgttcgctg cttcttccgc tttggctgct      60
ccagttaaca ctactactga ggacgagact gctcagattc agctgaagc tgttattggt     120 tactccgact ggaaggtga cttcgacgtt gctgttttgc cattctccaa ctccactaac     180
aacggtttgt tgttcatcaa cactacaatc gcttccattg ctgctaaaga agagggagtt    240
tccttggaga agagagaggc tgaagctaac ccaagagaaa acttcttgaa gtgttttcc    300 cagtacatcc caaacaacgc tacaaacttg aagttggttt acactcagaa caacccattg    360
tacatgtccg ttttgaactc cacaatccac aacttgagat tcacttccga cactactcca    420
```

```
aagccattgg ttatcgttac tccatcccac gtttcccaca tccagggtac tattttgtgt      480
tccaagaagg ttggattgca gatcagaaca agatccggtg gtcacgactc tgaaggtatg      540
tcctacattt cccaggttcc tttcgttatc gttgacttga gaaacatgag atccatcaag      600
atcgacgttc actcccagac tgcttgggtt gaagctggtg ctactttggg tgaagtttac      660
tactgggtta acgagaagaa cgagaacttg tccttggctg ctggttactg tccaactgtt      720
tgtgctggtg tcatttcgg tggtggtggt tatggtccat tgatgagaaa ctacggtttg       780
gctgctgaca acatcatcga cgctcacttg gttaacgttc acggtaaggt tttggacaga      840
aagtccatgg gtgaggactt gttctgggct tgagaggtg gtggtgctga atccttcggt       900
attatcgttg cttggaagat cagattggtt gctgttccaa agtccactat gttctccgtt      960
aagaaaatca tggaaatcca cgaattggtt aagttggtta acaagtggca gaacattgct     1020
tacaagtacg acaaggattt gttgttgatg actcacttca tcactagaaa catcactgac     1080
aaccagggta agaacaagac tgctatccac acttacttct cttccgtttt cttgggtggt     1140
gttgactcct tggttgattt gatgaacaag tccttcccag agttgggtat caagaaaact     1200
gactgtagac agttgtcctg gatcgacact atcatcttct actccggtgt tgttaactac     1260
gacacagaca acttcaacaa agagatcttg ttggacagat ccgctggaca gaacggtgct     1320
ttcaagatca agttggacta cgttaagaag ccaatcccag agtccgtttt cgttcagatt     1380
ttggagaagt tgtacgaaga ggacatcggt gctggtatgt acgctttgta cccatacggt     1440
ggtatcatgg acgaaatttc cgagtccgct attccattcc cacacagagc tggtatcttg     1500
tacgagttgt ggtacatctg ttcttgggag aagcaagagg acaacgagaa gcacttgaac     1560
tggatcagaa acatctacaa cttcatgact ccatacgttt ccaagaaccc aagattggct     1620
tacttgaact acagagactt ggacatcgga atcaacgacc caagaaccc taacaactac      1680 actcaggcta gaatctgggg tgaaaagtac ttcggtaaga acttcgacag attggttaag     1740
gttaagactt tggttgaccc aaacaatttc ttcagaaacg agcagtccat ccctccattg     1800
ccaagacata gacatcatca ccatcaccac taa                                  1833
```

<210> SEQ ID NO 8
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Asn Pro Arg Glu Asn Phe Leu
                85                  90                  95

Lys Cys Phe Ser Gln Tyr Ile Pro Asn Asn Ala Thr Asn Leu Lys Leu
            100                 105                 110

```
Val Tyr Thr Gln Asn Asn Pro Leu Tyr Met Ser Val Leu Asn Ser Thr
            115                 120                 125

Ile His Asn Leu Arg Phe Thr Ser Asp Thr Thr Pro Lys Pro Leu Val
    130                 135                 140

Ile Val Thr Pro Ser His Val Ser His Ile Gln Gly Thr Ile Leu Cys
145                 150                 155                 160

Ser Lys Lys Val Gly Leu Gln Ile Arg Thr Arg Ser Gly Gly His Asp
                165                 170                 175

Ser Glu Gly Met Ser Tyr Ile Ser Gln Val Pro Phe Val Ile Val Asp
            180                 185                 190

Leu Arg Asn Met Arg Ser Ile Lys Ile Asp Val His Ser Gln Thr Ala
        195                 200                 205

Trp Val Glu Ala Gly Ala Thr Leu Gly Glu Val Tyr Tyr Trp Val Asn
    210                 215                 220

Glu Lys Asn Glu Asn Leu Ser Leu Ala Ala Gly Tyr Cys Pro Thr Val
225                 230                 235                 240

Cys Ala Gly Gly His Phe Gly Gly Gly Tyr Gly Pro Leu Met Arg
                245                 250                 255

Asn Tyr Gly Leu Ala Ala Asp Asn Ile Ile Asp Ala His Leu Val Asn
            260                 265                 270

Val His Gly Lys Val Leu Asp Arg Lys Ser Met Gly Glu Asp Leu Phe
    275                 280                 285

Trp Ala Leu Arg Gly Gly Gly Ala Glu Ser Phe Gly Ile Ile Val Ala
    290                 295                 300

Trp Lys Ile Arg Leu Val Ala Val Pro Lys Ser Thr Met Phe Ser Val
305                 310                 315                 320

Lys Lys Ile Met Glu Ile His Glu Leu Val Lys Leu Val Asn Lys Trp
                325                 330                 335

Gln Asn Ile Ala Tyr Lys Tyr Asp Lys Asp Leu Leu Leu Met Thr His
            340                 345                 350

Phe Ile Thr Arg Asn Ile Thr Asp Asn Gln Gly Lys Asn Lys Thr Ala
        355                 360                 365

Ile His Thr Tyr Phe Ser Ser Val Phe Leu Gly Gly Val Asp Ser Leu
    370                 375                 380

Val Asp Leu Met Asn Lys Ser Phe Pro Glu Leu Gly Ile Lys Lys Thr
385                 390                 395                 400

Asp Cys Arg Gln Leu Ser Trp Ile Asp Thr Ile Ile Phe Tyr Ser Gly
                405                 410                 415

Val Val Asn Tyr Asp Thr Asp Asn Phe Asn Lys Glu Ile Leu Leu Asp
            420                 425                 430

Arg Ser Ala Gly Gln Asn Gly Ala Phe Lys Ile Lys Leu Asp Tyr Val
        435                 440                 445

Lys Lys Pro Ile Pro Glu Ser Val Phe Val Gln Ile Leu Glu Lys Leu
    450                 455                 460

Tyr Glu Glu Asp Ile Gly Ala Gly Met Tyr Ala Leu Tyr Pro Tyr Gly
465                 470                 475                 480

Gly Ile Met Asp Glu Ile Ser Glu Ser Ala Ile Pro Phe Pro His Arg
                485                 490                 495

Ala Gly Ile Leu Tyr Glu Leu Trp Tyr Ile Cys Ser Trp Glu Lys Gln
            500                 505                 510

Glu Asp Asn Glu Lys His Leu Asn Trp Ile Arg Asn Ile Tyr Asn Phe
        515                 520                 525
```

```
Met Thr Pro Tyr Val Ser Lys Asn Pro Arg Leu Ala Tyr Leu Asn Tyr
            530                 535                 540

Arg Asp Leu Asp Ile Gly Ile Asn Asp Pro Lys Asn Pro Asn Asn Tyr
545                 550                 555                 560

Thr Gln Ala Arg Ile Trp Gly Glu Lys Tyr Phe Gly Lys Asn Phe Asp
                565                 570                 575

Arg Leu Val Lys Val Lys Thr Leu Val Asp Pro Asn Asn Phe Phe Arg
                580                 585                 590

Asn Glu Gln Ser Ile Pro Pro Leu Pro Arg His Arg His His His
            595                 600                 605

His His
    610

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5
```